United States Patent
Sidhu et al.

(10) Patent No.: US 11,124,575 B2
(45) Date of Patent: Sep. 21, 2021

(54) EGFR-BINDING AGENTS AND USES THEREOF

(71) Applicants: University of Saskatchewan, Saskatoon (CA); The Governing Council of the University of Toronto, Toronto (CA)

(72) Inventors: Sachdev Sidhu, Toronto (CA); Shane Miersch, Toronto (CA); Clarence Ronald Geyer, Saskatoon (CA)

(73) Assignees: University of Saskatchewan, Saskatoon (CA); The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 16/487,673

(22) PCT Filed: Feb. 22, 2018

(86) PCT No.: PCT/CA2018/050202
§ 371 (c)(1),
(2) Date: Aug. 21, 2019

(87) PCT Pub. No.: WO2018/152634
PCT Pub. Date: Aug. 30, 2018

(65) Prior Publication Data
US 2020/0087405 A1    Mar. 19, 2020

Related U.S. Application Data

(60) Provisional application No. 62/462,175, filed on Feb. 22, 2017.

(51) Int. Cl.
C07K 16/28     (2006.01)
A61K 47/68     (2017.01)
(Continued)

(52) U.S. Cl.
CPC ...... *C07K 16/2863* (2013.01); *A61K 47/6849* (2017.08); *A61K 49/0032* (2013.01);
(Continued)

(58) Field of Classification Search
None
See application file for complete search history.

(56) References Cited

U.S. PATENT DOCUMENTS 7,887,805 B2 *  2/2011  Pedersen .......... A61K 39/39558
                                                      424/143.1
9,226,964 B2 *  1/2016  Bukhalid ................ A61P 11/00
(Continued)

FOREIGN PATENT DOCUMENTS

AU    2013200209 A1    2/2013
WO    2013134881 A1    9/2013
(Continued)

OTHER PUBLICATIONS

Cochran et al., Domain-level antibody epitope mapping through yeast surface display of epidermal growth factor receptor fragmentsJ. Immunological Methods, 287:147-158, 2004.*
(Continued)

*Primary Examiner* — Claire Kaufman
(74) *Attorney, Agent, or Firm* — Melanie Szweras; Ainslie Parsons; Bereskin & Parr LLP/S.E.N.C.R.L., s.r.l.

(57) ABSTRACT

An Epidermal Growth Factor Receptor (EGFR, HER1, ErbB1)-binding agent has a heavy chain and a light chain, wherein the dimerization loop from EGFR's Domain II is grafted within complementarity determining region 3 (CDR3) of the heavy chain, and the binding agent is affinity matured. The graft directs the binding agent to bind EGFR at its dimerization region, to thereby inhibit EGFR dimerization and activation. In another embodiment, an EGFR-binding agent is panned out of Library F, a Fab library. The
(Continued)

binding agents are for detecting and/or quantifying EGFR expression, for targeting EGFR-expressing cells, and for decreasing levels of EGFR in EGFR-expressing cells.

16 Claims, 40 Drawing Sheets

Specification includes a Sequence Listing.

(51) Int. Cl.
*A61K 49/00* (2006.01)
*G01N 33/68* (2006.01)

(52) U.S. Cl.
CPC ..... *A61K 49/0058* (2013.01); *G01N 33/6872* (2013.01); *C07K 2317/21* (2013.01); *C07K 2317/55* (2013.01); *C07K 2317/565* (2013.01); *C07K 2317/76* (2013.01); *G01N 2333/71* (2013.01)

(56) References Cited

U.S. PATENT DOCUMENTS

| | | | |
|---|---|---|---|
| 2012/0071419 A1 | 3/2012 | Choi et al. | |
| 2017/0058035 A1* | 3/2017 | Logtenberg | A61P 35/04 |

FOREIGN PATENT DOCUMENTS

| | | |
|---|---|---|
| WO | 2015130172 A1 | 9/2015 |
| WO | 2015173249 A1 | 11/2015 |

OTHER PUBLICATIONS

Gan et al., Targetingof a conformationally exposed, tumor-specific epitope of EGFR as a strategy for cancer therapy, Canc. Res. 72 (12):2924-30, 2012.*

Zhu et al., B-cell epitope peptide vaccination targeting dimer interface of epidermal growth factor receptor (EGFR), Immunol. Lett. 153(1-2):33-40, Jun. 1, 2013.*

Johns, T.G. et al., "Identification of the Epitope for the Epidermal Growth Factor Receptor-specific Monoclonal Antibody 806 Reveals That It Preferentially Recognizes an Untethered Form of the Receptor." J Biol. Chem., Jul. 16, 2004, vol. 279, No. 29, pp. 30375-30384, ISSN 0021-9258.

Choi, Y.S. et al., "Computational Design of Binding Proteins to EGFR Domain II", published online Apr. 7, 2014, PLoS One, vol. 9(4), e92513 (online). ISSN 1932-6203.

Miersch, S. et al., "Structure-Directed and Tailored Diversity Synthetic Antibody Libraries Yield Novel Anti-EGFR Antagonists", ACS Chem Biol., Apr. 4, 2017, vol. 12, pp. 1381-1389. ISSN 1554-8929. (Whole document).

International Preliminary Report on Patentability, received in connection to underlying international patent application No. PCT/CA2018/050202, dated Sep. 6, 2019.

Miersch, S: "Targeting Epitopes: Structure-directed approaches to the selection of antibodies from combinatorial libraries", PowerPoint presentation at the Ottawa Heart Research Institute, Apr. 26, 2012.

Sanchez-Heras Elena et al. "The fibroblast growth factor receptor acid box is essential for interactions with N-cadherin and all of the major isoforms of neural cell adhesion molecule." Journal of Biological Chemistry, American Society for Biochemistry and Molecular Biology, US, vol. 281, No. 46, Nov. 1, 2006 (Nov. 1, 2006), pp. 35208-35216, ISSN: 0021-9258.

Xu John L et al. "Diversity in the CDR3 region of VH is sufficient for most antibody specificities." Immunity, Cell Press, Amsterdam, NL, vol. 13, No. 1, Jul. 1, 2000 (Jul. 1, 2000), pp. 37-45, ISSN: 1074-7613.

Partial Supplementary European Search Report dated Aug. 12, 2020 in related EP Patent Application No. 18757454.6 (17 pages).

Extended European Search Report dated Mar. 12, 2021 in related EP Patent Application No. 18757454.6 (13 pages).

* cited by examiner

Figure 17 con't
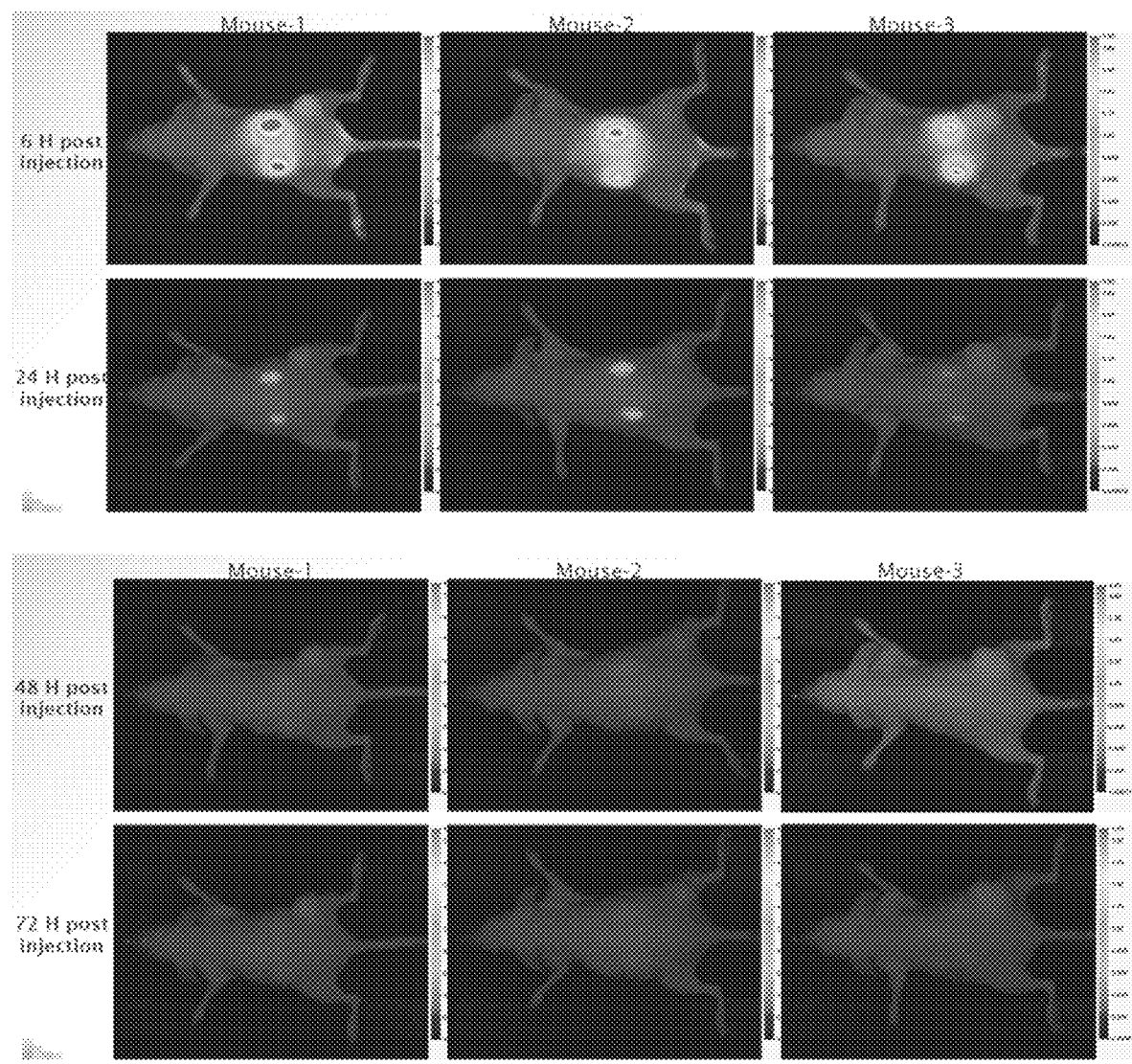

Figure 18 con't
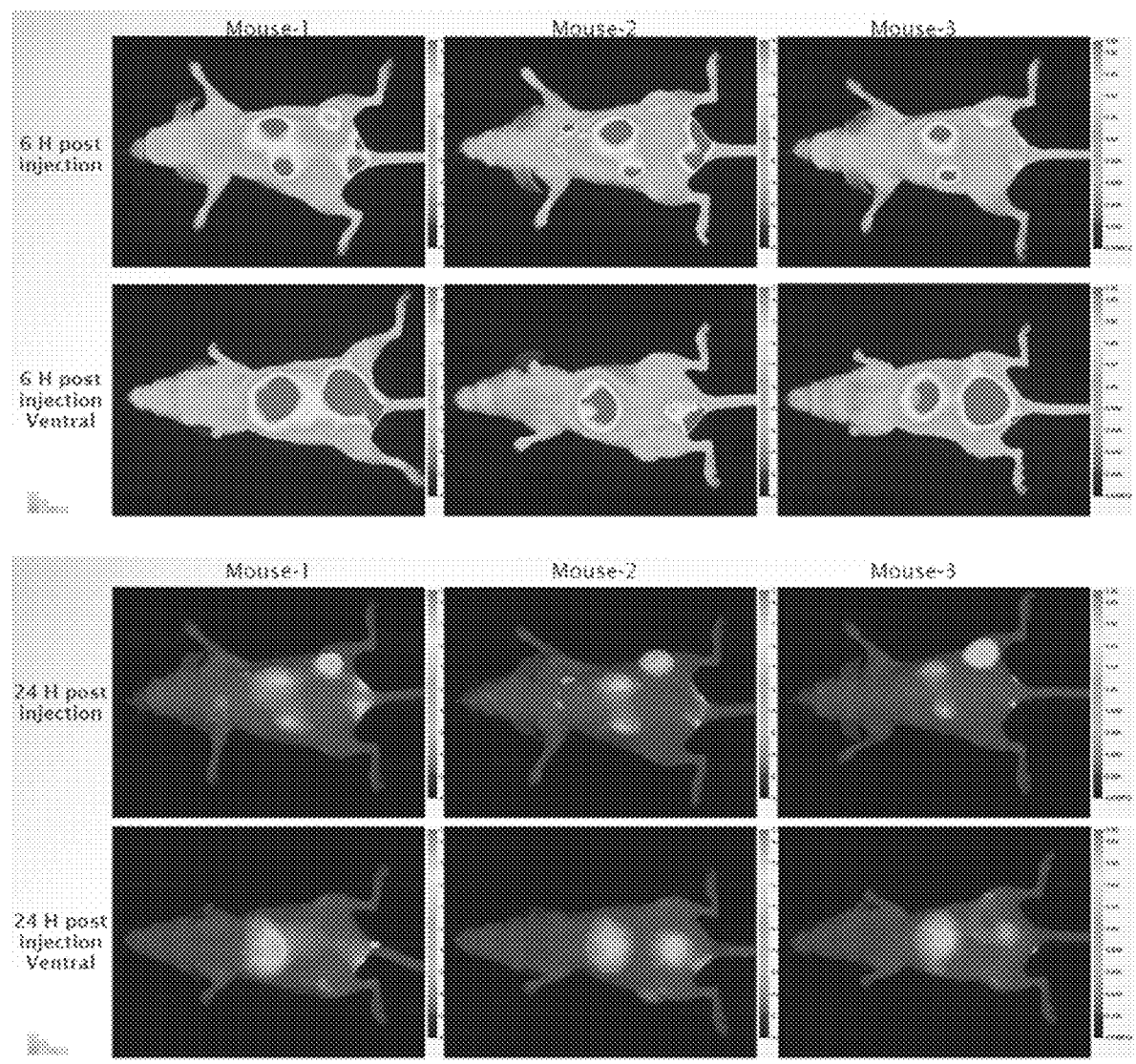

Figure 18 con't
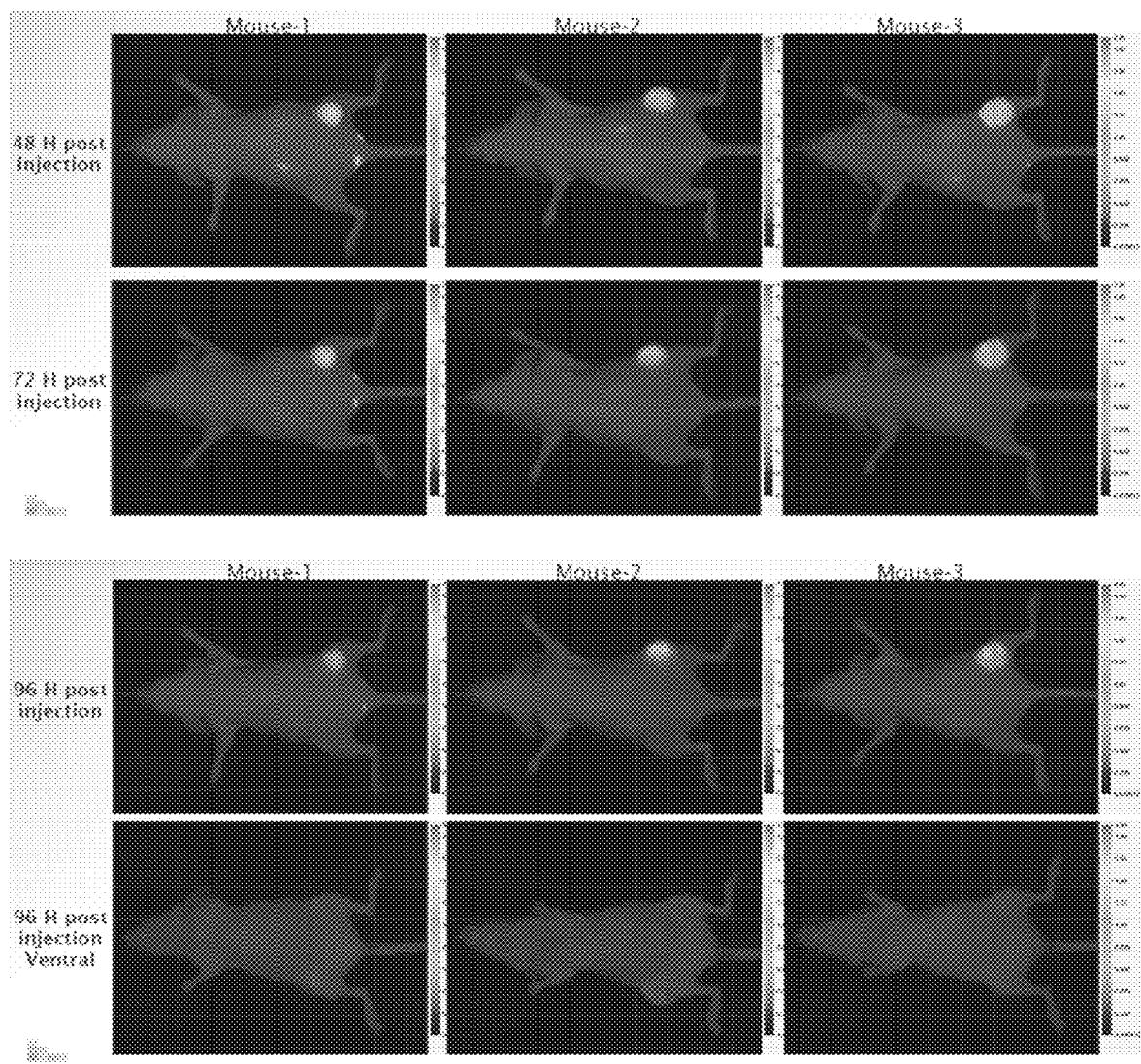

Figure 20 con't
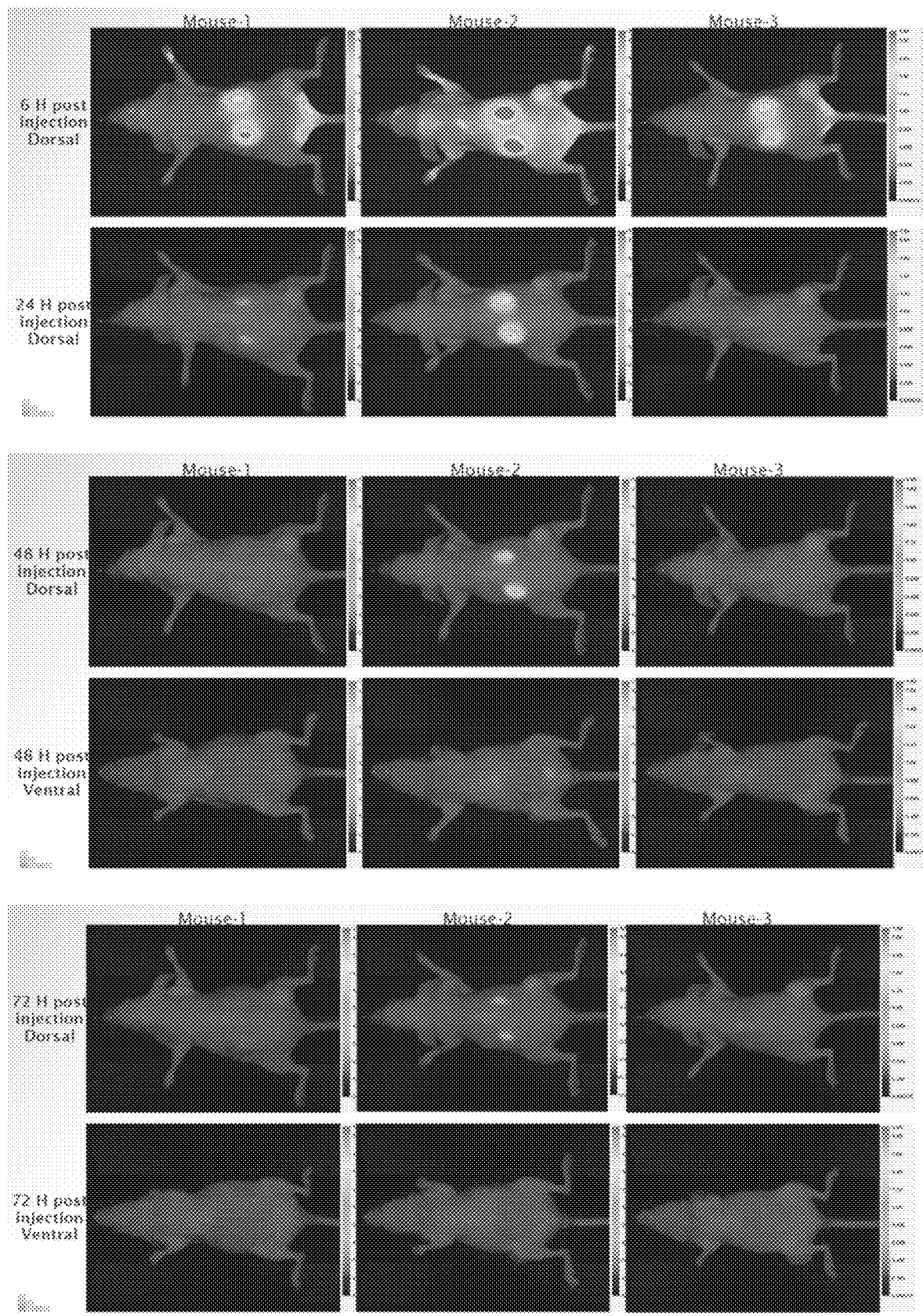

Figure 22 con't
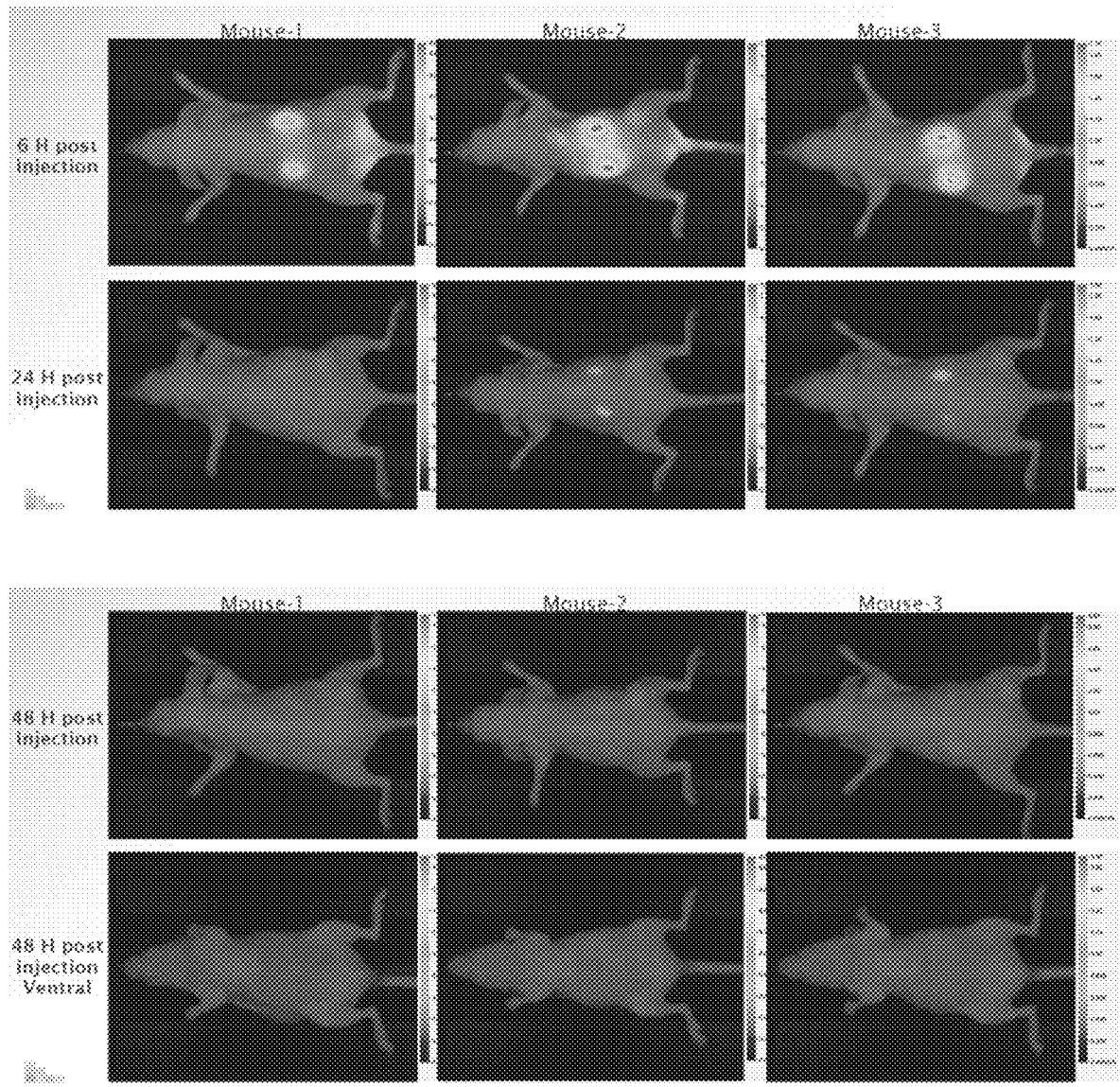

Figure 23 con't
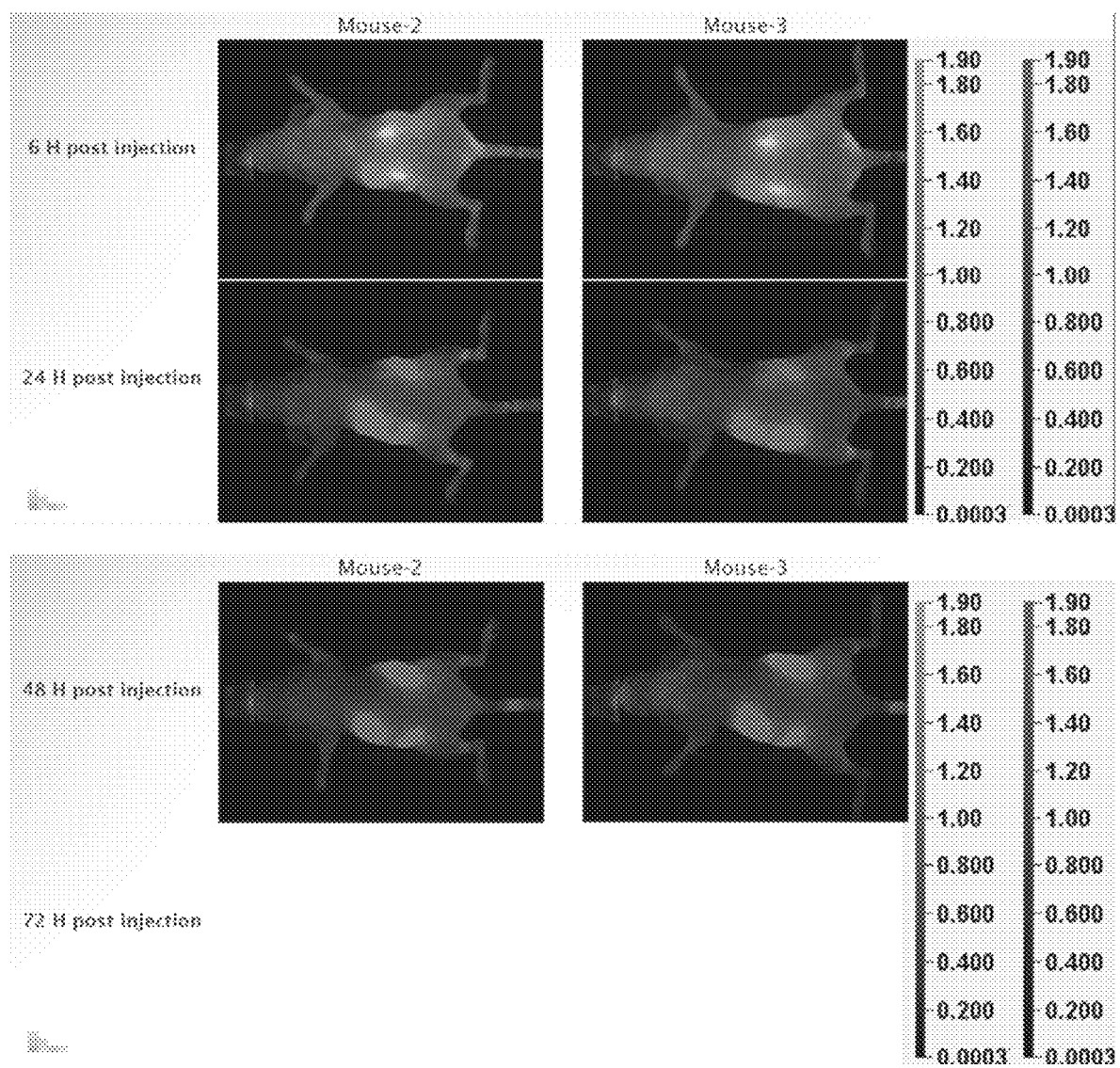

Figure 24 con't
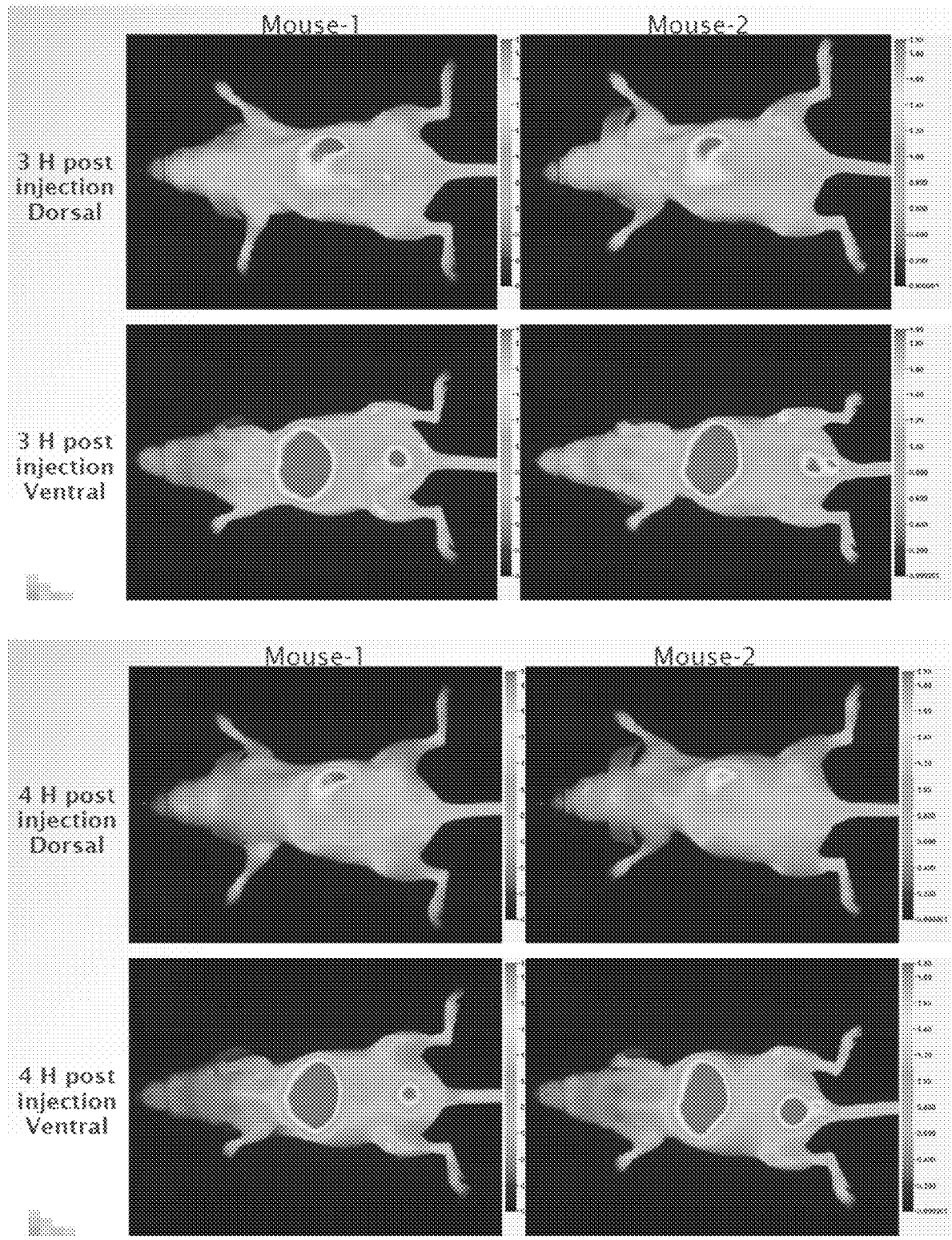

Figure 24 con't
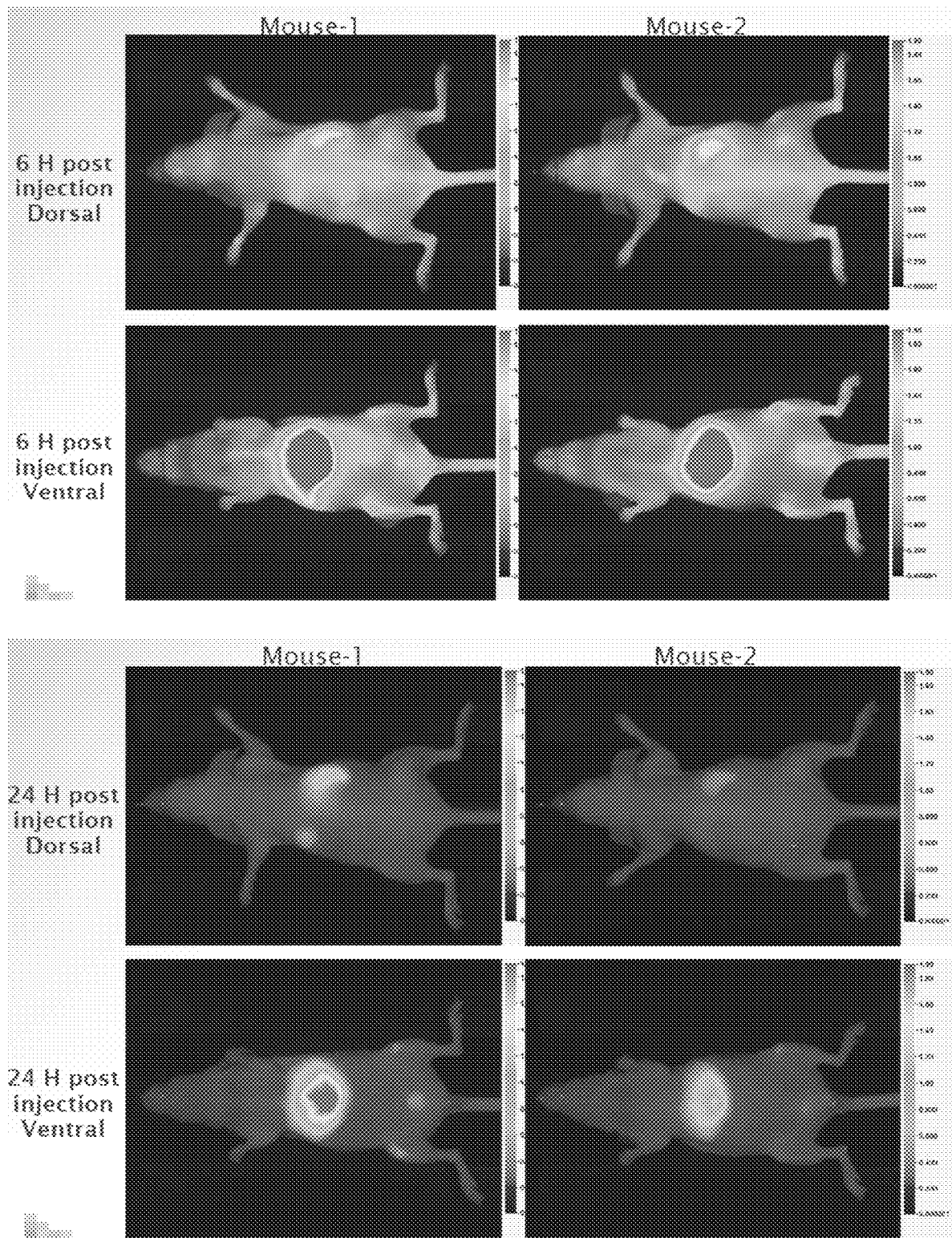

Figure 24 con't
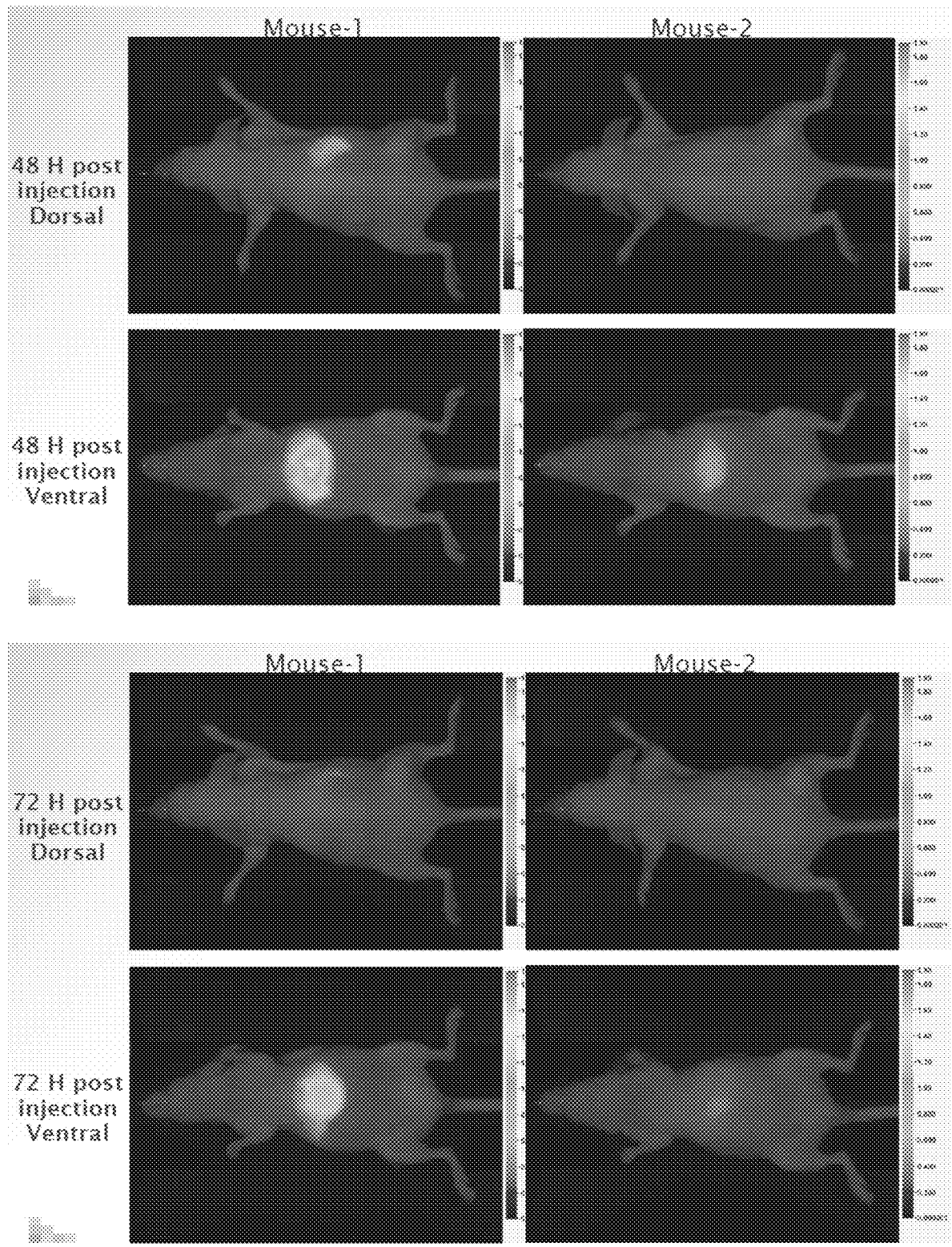

Figure 25 con't
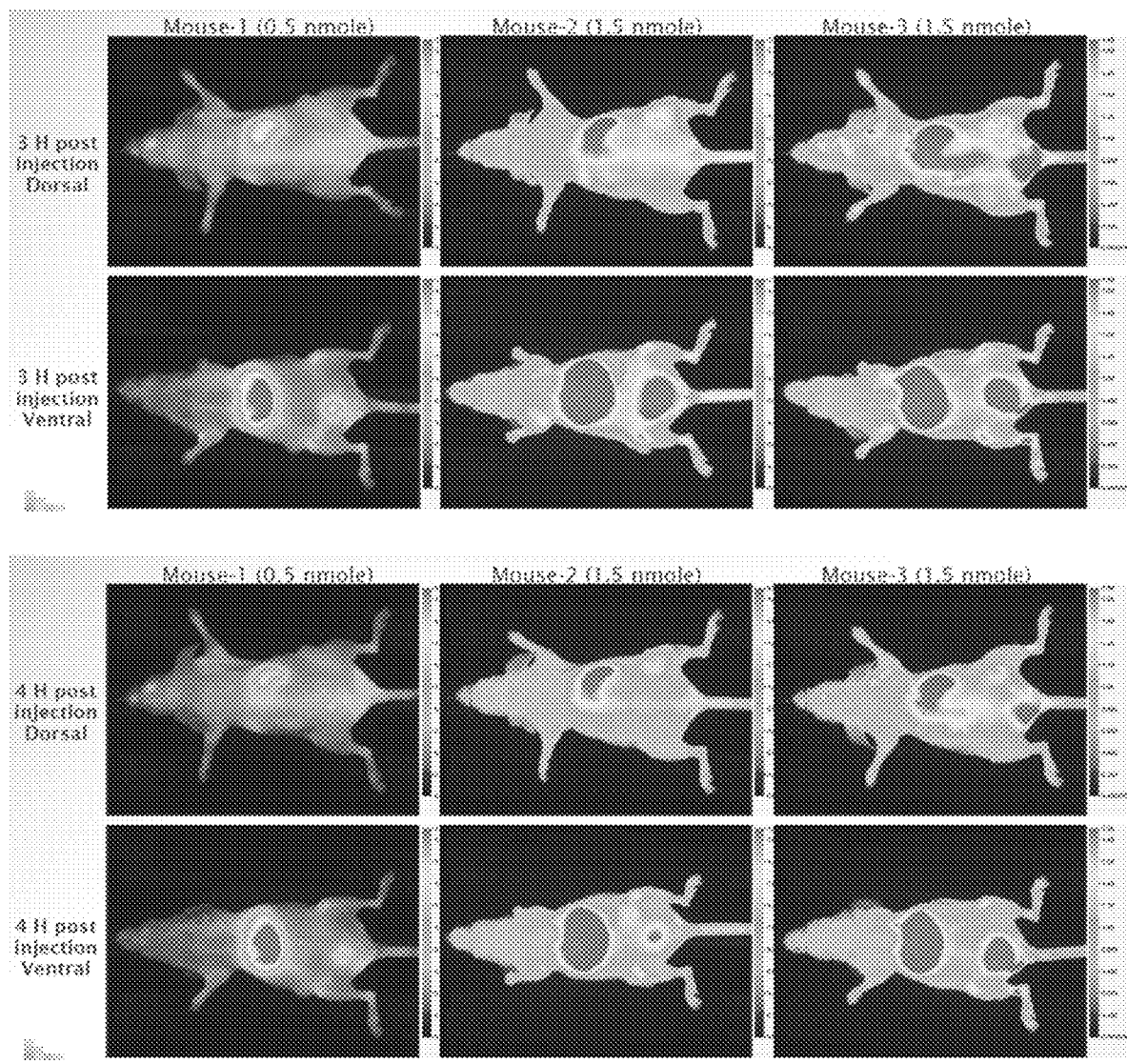

Figure 25 con't
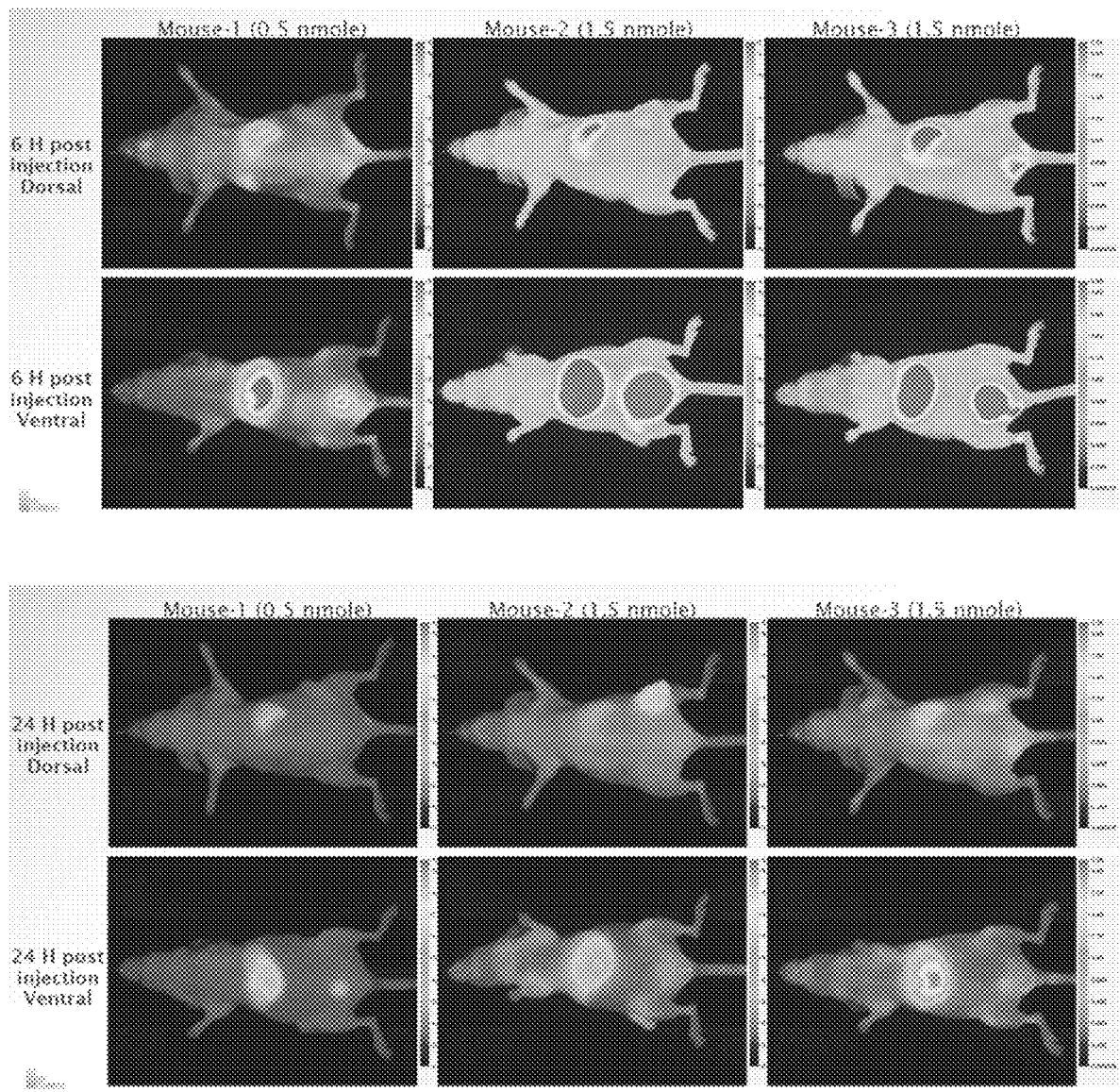

Figure 25 con't
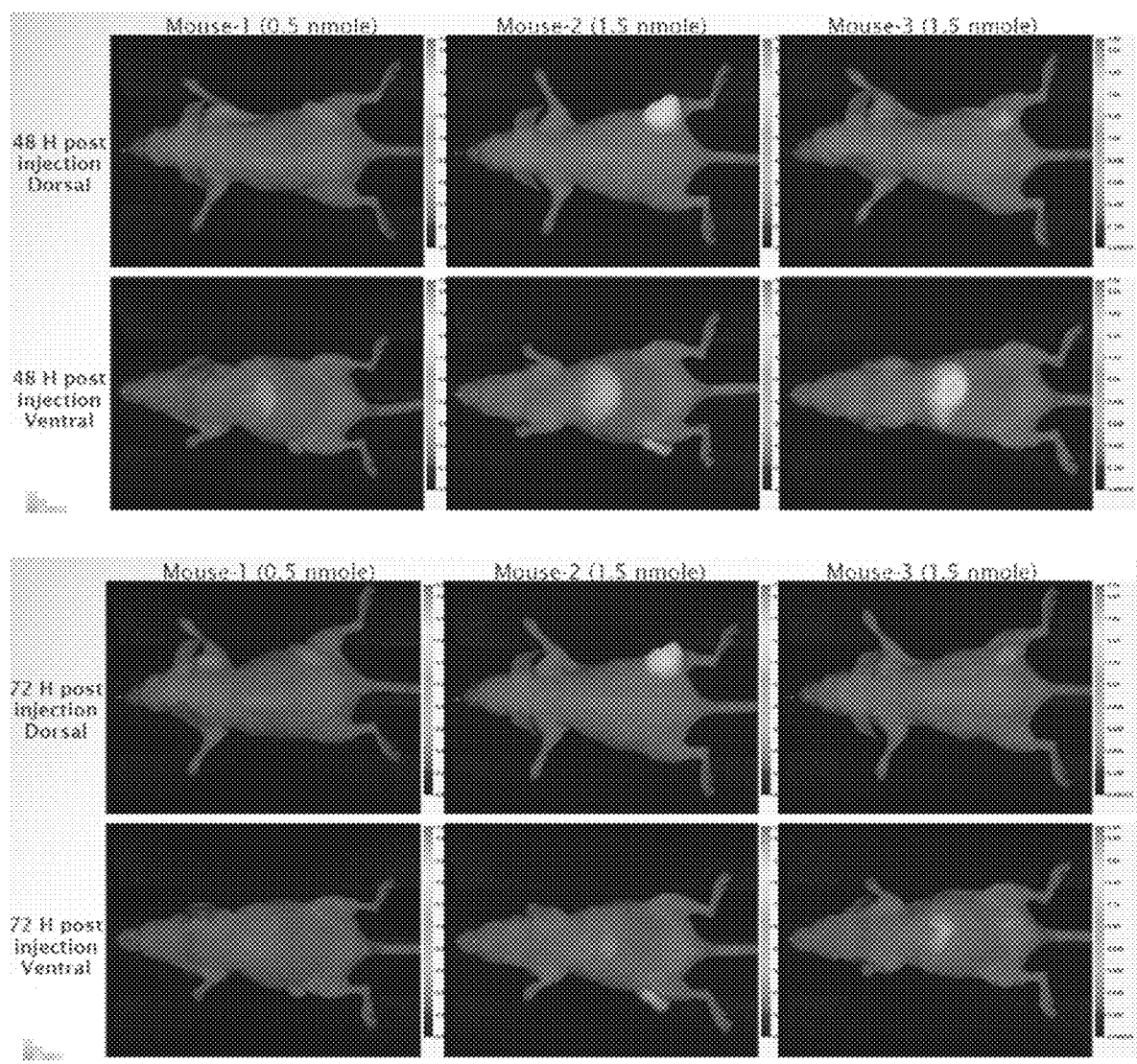

SEQUENCE LISTING

```
<160> NUMBER OF SEQ ID NOS: 58

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct

<400> SEQUENCE: 1

Gln Ser Val Ser Ser Ala
1               5

<210> SEQ ID NO 2
<211> LENGTH: 3
<212> TYPE: PRT
<213> ORGANISM: Artificial Sequence
<220> FEATURE:
<223> OTHER INFORMATION: Synthetic Construct

<400> SEQUENCE: 2

Ser Ala Ser
1

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Gln Gln Trp Ser Tyr Tyr Pro Ile Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Gln Gln Trp Ser Tyr Tyr Pro Phe Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Gln Gln Ser Tyr Trp Leu Ile Thr
1               5

<210> SEQ ID NO 6
<211> LENGTH: 9
<212> TYPE: PRT
```

<213> ORGANISM: Artificial Sequence
<220> FEATURE:
<223> OTHER INFORMATION: Synthetic Construct

<400> SEQUENCE: 6

Gly Phe Asn Ile Ser Ser Ser Ser Ile
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Gly Phe Asn Phe Ser Ser Ser Ser Ile
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Gly Phe Asn Leu Tyr Ser Ser Ser Met
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Tyr Ile Ser Ser Tyr Tyr Ser Ser Thr Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Ser Ile Tyr Pro Tyr Ser Gly Tyr Thr Tyr
1               5                   10

<210> SEQ ID NO 11
<211> LENGTH: 38
<212> TYPE: PRT
<213> ORGANISM: Artificial Sequence
<220> FEATURE:
<223> OTHER INFORMATION: Synthetic Construct

<400> SEQUENCE: 11

Ala Arg Thr Tyr Cys Pro Pro Leu Met Leu Tyr Asn Pro Thr Thr Tyr
1               5                   10                  15

Gln Met Asp Val Asn Pro Glu Gly Lys Tyr Ser Phe Gly Ala Thr Cys
            20                  25                  30

Gly Trp Ala Met Asp Tyr
        35

<210> SEQ ID NO 12
<211> LENGTH: 38
<212> TYPE: PRT
<213> ORGANISM: Artificial Sequence
<220> FEATURE:
<223> OTHER INFORMATION: Synthetic Construct

<400> SEQUENCE: 12

Ala Arg Thr Phe Cys Pro Pro Leu Met Leu Tyr Asn Pro Thr Thr Tyr
1               5                   10                  15

Gln Leu Glu Ile Asn Pro Glu Ala Lys Tyr Ser Phe Ala Ser Thr Cys
            20                  25                  30

Gly Trp Ala Met Asp Tyr
        35

<210> SEQ ID NO 13
<211> LENGTH: 38
<212> TYPE: PRT
<213> ORGANISM: Artificial Sequence
<220> FEATURE:
<223> OTHER INFORMATION: Synthetic Construct

<400> SEQUENCE: 13

Ala Arg Thr Phe Cys Pro Pro Ile Met Leu Phe Asn Ala Thr Ser Phe
1               5                   10                  15

Glu Leu Asp Ile Asp Ala Glu Ala Lys Phe Ser Phe Ala Ser Thr Cys
            20                  25                  30

Gly Trp Ala Met Asp Tyr
        35

<210> SEQ ID NO 14
<211> LENGTH: 38
<212> TYPE: PRT
<213> ORGANISM: Artificial Sequence
<220> FEATURE:
<223> OTHER INFORMATION: Synthetic Construct

<400> SEQUENCE: 14

Ala Arg Thr Phe Cys Pro Pro Leu Met Leu Phe Asn Pro Thr Thr Phe
1               5                   10                  15

Gln Leu Glu Ile Asn Ala Glu Ala Lys Tyr Ser Phe Ala Ser Thr Cys
            20                  25                  30

Gly Trp Ala Met Asp Tyr
        35

<210> SEQ ID NO 15
<211> LENGTH: 38
<212> TYPE: PRT
<213> ORGANISM: Artificial Sequence
<220> FEATURE:
<223> OTHER INFORMATION: Synthetic Construct

<400> SEQUENCE: 15

Ala Arg Thr Tyr Cys Pro Pro Leu Met Arg Tyr Asn Pro Thr Thr Tyr
1               5                   10                  15

Gln Met Asp Val Asn Pro Glu Ala Gln Tyr Ser Phe Gly Ala Thr Cys
            20                  25                  30

Gly Trp Ala Met Asp Tyr
        35

<210> SEQ ID NO 16

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Ala Arg Tyr Pro Phe Gly Val Ser Ala Tyr Tyr Ala Met Asp Tyr
1               5                   10                  15

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Ser Ser Tyr Ser Leu Ile
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Phe Ser Ser Ser Ser Ile
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Ser Ile Ser Ser Ser Tyr Gly Tyr Thr Tyr
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Thr Val Arg Gly Ser Lys Lys Pro Tyr Phe Ser Gly Trp Ala Met
1               5                   10                  15

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Trp Ser Tyr Tyr Pro Ile
1               5

<210> SEQ ID NO 22
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 22

Ile Ser Ser Ser Ser Ile
1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct

<400> SEQUENCE: 23

Tyr Ile Ser Ser Tyr Tyr Ser Ser Thr Tyr
1               5                   10

<210> SEQ ID NO 24
<211> LENGTH: 34
<212> TYPE: PRT
<213> ORGANISM: Artificial Sequence
<220> FEATURE:
<223> OTHER INFORMATION: Synthetic Construct

<400> SEQUENCE: 24

Thr Tyr Cys Pro Pro Leu Met Leu Tyr Asn Pro Thr Thr Tyr Gln Met
1               5                   10                  15

Asp Val Asn Pro Glu Gly Lys Tyr Ser Phe Gly Ala Thr Cys Gly Trp
            20                  25                  30

Ala Met

<210> SEQ ID NO 25
<211> LENGTH: 6
<212> TYPE: PRT
<213> ORGANISM: Artificial Sequence
<220> FEATURE:
<223> OTHER INFORMATION: Synthetic Construct

<400> SEQUENCE: 25

Trp Ser Tyr Tyr Pro Ile
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Construct

<400> SEQUENCE: 26

Ile Ser Ser Ser Ser Ile
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct

<400> SEQUENCE: 27

Tyr Ile Ser Ser Tyr Tyr Ser Ser Thr Tyr
1               5                   10
```

<210> SEQ ID NO 28
<211> LENGTH: 34
<212> TYPE: PRT
<213> ORGANISM: Artificial Sequence
<220> FEATURE:
<223> OTHER INFORMATION: Synthetic Construct

<400> SEQUENCE: 28

Thr Tyr Cys Pro Pro Leu Met Arg Tyr Asn Pro Thr Thr Tyr Gln Met
1               5                   10                  15

Asp Val Asn Pro Glu Ala Gln Tyr Ser Phe Gly Ala Thr Cys Gly Trp
            20                  25                  30

Ala Met

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Ser Tyr Trp Leu Ile
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

Leu Tyr Ser Ser Ser Met
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Ser Ile Tyr Pro Tyr Ser Gly Tyr Thr Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Tyr Pro Phe Gly Val Ser Ala Tyr Tyr Ala Met
1               5                   10

<210> SEQ ID NO 33
<211> LENGTH: 762
<212> TYPE: DNA
<213> ORGANISM: Artificial Sequence
<220> FEATURE:
<223> OTHER INFORMATION: Synthetic Construct

<400> SEQUENCE: 33

```
gaggttcagc tggtggagtc tgcggtggc ctggtgcagc cagggggctc actccgtttg      60
tcctgtgcag cttctggctt caacatctct tcttcttcta tccactgggt gcgtcaggcc    120
ccgggtaagg gcctggaatg ggttgcatat atttcttctt attatagctc tacttattat    180
gccgatagcg tcaagggccg tttcactata agcgcagaca catccaaaaa cacagcctac    240
ctacaaatga acagcctgag agctgaggac actgccgtct attattgtgc tcgcacttac    300
tgtcccccc tgatgctgta caaccccact acttaccaaa tggacgtcaa ccccgaaggt    360
aaatactctt ttggtgctac ttgtggctgg gctatggact actggggtca aggaaccctg    420
gtcaccgtct cctcggcctc caccaagggc ccatcggtct tccccctggc accctcctcc    480
aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtcgac    720
aagaaagttg agcccaaatc ttgtgacaaa actcacacat aa                       762
```

<210> SEQ ID NO 34
<211> LENGTH: 253
<212> TYPE: PRT
<213> ORGANISM: Artificial Sequence
<220> FEATURE:
<223> OTHER INFORMATION: Synthetic Construct

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Tyr Tyr Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Tyr Cys Pro Pro Leu Met Leu Tyr Asn Pro Thr Thr Tyr
            100                 105                 110

Gln Met Asp Val Asn Pro Glu Gly Lys Tyr Ser Phe Gly Ala Thr Cys
        115                 120                 125

Gly Trp Ala Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220
```

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr
            245                 250

<210> SEQ ID NO 35
<211> LENGTH: 678
<212> TYPE: DNA
<213> ORGANISM: Artificial Sequence
<220> FEATURE:
<223> OTHER INFORMATION: Synthetic Construct

<400> SEQUENCE: 35
gatatccaga tgacccagtc cccgagctcc ctgtccgcct ctgtgggcga tagggtcacc      60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat tcactctga ccatcagcag tctgcagccg     240
gaagacttcg caacttatta ctgtcagcaa tggtcttact acccgatcac gttcggacag    300
ggtaccaagg tggagatcaa acgaactgtg gctgcaccat ctgtcttcat cttcccgcca    360
tctgattcac agcttaagtc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacctgacg     540
ctgagcaaag cagactacga aaacataaa gtctacgcct gcgaagtcac ccatcagggc     600
ctgagctcgc ccgtcacaaa gagcttcaac agggagagt gtggtggttc tgattacaaa    660
gatgacgatg acaaataa                                                  678

<210> SEQ ID NO 36
<211> LENGTH: 225
<212> TYPE: PRT
<213> ORGANISM: Artificial Sequence
<220> FEATURE:
<223> OTHER INFORMATION: Synthetic Construct

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Tyr Tyr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln

```
                145                 150                 155                 160
Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Glu Cys Gly Gly Ser Asp Tyr Lys Asp Asp Asp Asp
                210                 215                 220

Lys
225

<210> SEQ ID NO 37
<211> LENGTH: 762
<212> TYPE: DNA
<213> ORGANISM: Artificial Sequence
<220> FEATURE:
<223> OTHER INFORMATION: Synthetic Construct

<400> SEQUENCE: 37
gaggttcagc tggtggagtc tggcggtggc ctggtgcagc caggggggctc actccgtttg     60 tcctgtgcag cttctggctt caacatctct tcttcttcta tccactgggt gcgtcaggcc    120
ccgggtaagg gcctggaatg ggttgcatat atttcttctt attatagctc tacttattat    180
gccgatagcg tcaagggccg tttcactata agcgcagaca catccaaaaa cacagcctac    240
ctacaaatga acagcctgag agctgaggac actgccgtct attattgtgc tcgcactttc    300
tgcccaccac tcatgctcta accccaacc acctaccaac tggaaattaa cccagaagct    360
aagtactcct tcgcttctac ctgcggttgg gctatggact actggggtca aggaaccctg    420
gtcaccgtct cctcggcctc caccaagggc ccatcggtct tccccctggc accctcctcc    480
aagagcacct ctggggggcac agcggccctg ggctgcctgg tcaaggacta cttcccggaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtcgac    720
aagaaagttg agcccaaatc ttgtgacaaa actcacacat aa                       762

<210> SEQ ID NO 38
<211> LENGTH: 253
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Tyr Tyr Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
            85                  90                  95
Ala Arg Thr Phe Cys Pro Pro Leu Met Leu Tyr Asn Pro Thr Thr Tyr
            100                 105                 110

Gln Leu Glu Ile Asn Pro Glu Ala Lys Tyr Ser Phe Ala Ser Thr Cys
            115                 120                 125

Gly Trp Ala Met Asp Tyr Trp Gly Gln Gly Thr Leu Val Thr Val Ser
        130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
        210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr
                245                 250
```

```
<210> SEQ ID NO 39
<211> LENGTH: 678
<212> TYPE: DNA
<213> ORGANISM: Artificial Sequence
<220> FEATURE:
<223> OTHER INFORMATION: Synthetic Construct

<400> SEQUENCE: 39
gatatccaga tgacccagtc cccgagctcc ctgtccgcct ctgtgggcga tagggtcacc      60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa tggtcttact acccgatcac gttcggacag    300
ggtaccaagg tggagatcaa acgaactgtg gctgcaccat ctgtcttcat cttcccgcca    360
tctgattcac agcttaagtc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaacataaa gtctacgcct gcgaagtcac ccatcagggc    600
ctgagctcgc ccgtcacaaa gagcttcaac aggggagagt gtggtggttc tgattacaaa    660
gatgacgatg acaaataa                                                 678
```

```
<210> SEQ ID NO 40
<211> LENGTH: 225
<212> TYPE: PRT
<213> ORGANISM: Artificial Sequence
<220> FEATURE:
<223> OTHER INFORMATION: Synthetic Construct

<400> SEQUENCE: 40

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Tyr Tyr Pro Ile
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Asp Tyr Lys Asp Asp Asp Asp
    210                 215                 220

Lys
225

<210> SEQ ID NO 41
<211> LENGTH: 762
<212> TYPE: DNA
<213> ORGANISM: Artificial Sequence
<220> FEATURE:
<223> OTHER INFORMATION: Synthetic Construct

<400> SEQUENCE: 41
gaggttcagc tggtggagtc tggcggtggc ctggtgcagc caggggctc actccgtttg      60 tcctgtgcag cttctggctt caacatctct tcttcttcta tccactgggt gcgtcaggcc    120
ccgggtaagg gcctggaatg ggttgcatat atttcttctt attatagctc tacttattat    180
gccgatagcg tcaagggccg tttcactata agcgcagaca catccaaaaa cacagcctac    240
ctacaaatga acagcctgag agctgaggac actgccgtct attattgtgc tcgcactttc    300
tgcccaccaa tcatgctctt caacgcaacc agcttcgaac tggacattga cgcagaagct    360
aagttctcct tcgcttctac ctgcggttgg gctatggact actggggtca aggaaccctg    420
gtcaccgtct cctcggcctc caccaagggc ccatcggtct tccccctggc acctcctcc     480 aagagcacct ctgggggcac agcggccctg ggctgcctgg tcaaggacta cttcccggaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtcgac    720
aagaaagttg agcccaaatc ttgtgacaaa actcacacat aa                       762
```

<210> SEQ ID NO 42
<211> LENGTH: 253
<212> TYPE: PRT
<213> ORGANISM: Artificial Sequence
<220> FEATURE:
<223> OTHER INFORMATION: Synthetic Construct

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser
            20                  25                  30

Ser Ile His Trp Val Arg Gln Ala Pro Gly Lys Gly Leu Glu Trp Val
        35                  40                  45

Ala Tyr Ile Ser Ser Tyr Tyr Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Phe Cys Pro Pro Ile Met Leu Phe Asn Ala Thr Ser Phe
            100                 105                 110

Glu Leu Asp Ile Asp Ala Glu Ala Lys Phe Ser Phe Ala Ser Thr Cys
        115                 120                 125

Gly Trp Ala Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr
                245                 250
```

<210> SEQ ID NO 43
<211> LENGTH: 678
<212> TYPE: DNA
<213> ORGANISM: Artificial Sequence
<220> FEATURE:
<223> OTHER INFORMATION: Synthetic Construct

<400> SEQUENCE: 43

```
gatatccaga tgacccagtc cccgagctcc ctgtccgcct ctgtgggcga tagggtcacc      60
atcacctgcc gtgccagtca gtccgtgtcc agcgctgtag cctggtatca acagaaacca     120
ggaaaagctc cgaagcttct gatttactcg gcatccagcc tctactctgg agtcccttct     180
cgcttctctg gtagccgttc cgggacggat tcactctga  ccatcagcag tctgcagccg     240
gaagacttcg caacttatta ctgtcagcaa tggtcttact acccgatcac ggtcggacag     300
ggtaccaagg tggagatcaa acgaactgtg gctgcaccat ctgtcttcat cttcccgcca     360
```

```
tctgattcac agcttaagtc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaacataaa gtctacgcct gcgaagtcac ccatcagggc    600
ctgagctcgc ccgtcacaaa gagcttcaac aggggagagt gtggtggttc tgattacaaa    660
gatgacgatg acaaataa                                                   678
```

<210> SEQ ID NO 44
<211> LENGTH: 225
<212> TYPE: PRT
<213> ORGANISM: Artificial Sequence
<220> FEATURE:
<223> OTHER INFORMATION: Synthetic Construct

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Tyr Tyr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Asp Tyr Lys Asp Asp Asp Asp
    210                 215                 220

Lys
225
```

<210> SEQ ID NO 45
<211> LENGTH: 762
<212> TYPE: DNA
<213> ORGANISM: Artificial Sequence
<220> FEATURE:
<223> OTHER INFORMATION: Synthetic Construct

<400> SEQUENCE: 45

```
gaggttcagc tggtggagtc tggcggtggc ctggtgcagc caggggggctc actccgtttg    60
```

| | | |
|---|---|---|
| tcctgtgcag cttctggctt caacatctct tcttcttcta tccactgggt gcgtcaggcc | 120 | |
| ccgggtaagg gcctggaatg ggttgcatat atttcttctt attatagctc tacttattat | 180 | |
| gccgatagcg tcaagggccg tttcactata agcgcagaca catccaaaaa cacagcctac | 240 | |
| ctacaaatga acagcctgag agctgaggac actgccgtct attattgtgc tcgcactttc | 300 | |
| tgcccaccac tcatgctctt caacccaacc accttccaac tggaaattaa cgcagaagct | 360 | |
| aagtactcct tcgcttctac ctgcggttgg gctatggact actggggtca aggaaccctg | 420 | |
| gtcaccgtct cctcggcctc caccaagggc ccatcggtct tccccctggc accctcctcc | 480 | |
| aagagcacct ctggggggac agcggccctg ggctgcctgg tcaaggacta cttccccgaa | 540 | |
| ccggtgacgg tgtcgtggaa ctcaggcgcc ctgaccagcg gcgtgcacac cttcccggct | 600 | |
| gtcctacagt cctcaggact ctactccctc agcagcgtgg tgaccgtgcc ctccagcagc | 660 | |
| ttgggcaccc agacctacat ctgcaacgtg aatcacaagc ccagcaacac caaggtcgac | 720 | |
| aagaaagttg agcccaaatc ttgtgacaaa actcacacat aa | 762 | |

<210> SEQ ID NO 46
<211> LENGTH: 253
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Tyr Tyr Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Phe Cys Pro Pro Leu Met Leu Phe Asn Pro Thr Thr Phe
            100                 105                 110

Gln Leu Glu Ile Asn Ala Glu Ala Lys Tyr Ser Phe Ala Ser Thr Cys
        115                 120                 125

Gly Trp Ala Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr
            245                 250

<210> SEQ ID NO 47
<211> LENGTH: 678
<212> TYPE: DNA
<213> ORGANISM: Artificial Sequence
<220> FEATURE:
<223> OTHER INFORMATION: Synthetic Construct

<400> SEQUENCE: 47

```
gatatccaga tgacccagtc cccgagctcc ctgtccgcct ctgtgggcga tagggtcacc    60
atcacctgcc gtgccagtca gtccgtgtcc agcgctgtag cctggtatca acagaaacca   120
ggaaaagctc cgaagcttct gatttactcg gcatccagcc tctactctgg agtcccttct   180
cgcttctctg gtagccgttc cgggacggat ttcactctga ccatcagcag tctgcagccg   240
gaagacttcg caacttatta ctgtcagcaa tggtcttact acccgatcac gttcggacag   300
ggtaccaagg tggagatcaa cgaactgtg gctgcaccat ctgtcttcat cttcccgcca   360
tctgattcac agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacataaa gtctacgcct gcgaagtcac ccatcagggc   600
ctgagctcgc ccgtcacaaa gagcttcaac aggggagagt gtggtggttc tgattacaaa   660
gatgacgatg acaaataa                                                 678
```

<210> SEQ ID NO 48
<211> LENGTH: 225
<212> TYPE: PRT
<213> ORGANISM: Artificial Sequence
<220> FEATURE:
<223> OTHER INFORMATION: Synthetic Construct

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Tyr Tyr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Asp Tyr Lys Asp Asp Asp Asp
    210                 215                 220

Lys
225
```

<210> SEQ ID NO 49
<211> LENGTH: 762
<212> TYPE: DNA
<213> ORGANISM: Artificial Sequence
<220> FEATURE:
<223> OTHER INFORMATION: Synthetic Construct

<400> SEQUENCE: 49

```
gaggttcagc tggtggagtc tggcggtggc ctggtgcagc caggggggctc actccgtttg      60
tcctgtgcag cttctggctt caacatctct tcttcttcta tccactgggt gcgtcaggcc     120
ccgggtaagg gcctggaatg ggttgcatat atttcttctt attatagctc tacttattat     180
gccgatagcg tcaagggccg tttcactata agcgcagaca catccaaaaa cacagcctac     240
ctacaaatga acagcctgag agctgaggac actgccgtct attattgtgc cgcacttac      300
tgtccccccc tgatgcggta caaccccact acttaccaaa tggacgtcaa ccccgaggct     360
caatactctt tggggctac ttgtggctgg gctatggact actggggtca aggaaccctg      420
gtcaccgtct cctcggcctc caccaagggc ccatcggtct tccccctggc accctcctcc     480
aagagcacct ctgggggcac agcggccctg ggctgcctgg tcaaggacta cttcccggaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtcgac     720
aagaaagttg agcccaaatc ttgtgacaaa actcacacat aa                        762
```

<210> SEQ ID NO 50
<211> LENGTH: 253
<212> TYPE: PRT
<213> ORGANISM: Artificial Sequence
<220> FEATURE:
<223> OTHER INFORMATION: Synthetic Construct

<400> SEQUENCE: 50

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Tyr Tyr Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Tyr Cys Pro Pro Leu Met Arg Tyr Asn Pro Thr Thr Tyr
            100                 105                 110
```

Gln Met Asp Val Asn Pro Glu Ala Gln Tyr Ser Phe Gly Ala Thr Cys
            115                 120                 125
Gly Trp Ala Met Asp Tyr Trp Gly Gln Gly Thr Leu Val Thr Val Ser
        130                 135                 140
Ser Ala Ser Thr Lys Gly Pro Ser Val Phe Pro Leu Ala Pro Ser Ser
145                 150                 155                 160
Lys Ser Thr Ser Gly Gly Thr Ala Ala Leu Gly Cys Leu Val Lys Asp
                165                 170                 175
Tyr Phe Pro Glu Pro Val Thr Val Ser Trp Asn Ser Gly Ala Leu Thr
            180                 185                 190
Ser Gly Val His Thr Phe Pro Ala Val Leu Gln Ser Ser Gly Leu Tyr
        195                 200                 205
Ser Leu Ser Ser Val Val Thr Val Pro Ser Ser Ser Leu Gly Thr Gln
    210                 215                 220
Thr Tyr Ile Cys Asn Val Asn His Lys Pro Ser Asn Thr Lys Val Asp
225                 230                 235                 240
Lys Lys Val Glu Pro Lys Ser Cys Asp Lys Thr His Thr
                245                 250

<210> SEQ ID NO 51
<211> LENGTH: 678
<212> TYPE: DNA
<213> ORGANISM: Artificial Sequence
<220> FEATURE:
<223> OTHER INFORMATION: Synthetic Construct

<400> SEQUENCE: 51
gatatccaga tgacccagtc cccgagctcc ctgtccgcct ctgtgggcga tagggtcacc      60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa tggtcttact acccgatcac gttcggacag    300
ggtaccaagg tggagatcaa acgaactgtg gctgcaccat ctgtcttcat cttcccgcca    360
tctgattcac agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaacataaa gtctacgcct gcgaagtcac ccatcagggc    600
ctgagctcgc ccgtcacaaa gagcttcaac aggggagagt gtggtggttc tgattacaaa    660
gatgacgatg acaaataa                                                 678

<210> SEQ ID NO 52
<211> LENGTH: 225
<212> TYPE: PRT
<213> ORGANISM: Artificial Sequence
<220> FEATURE:
<223> OTHER INFORMATION: Synthetic Construct

<400> SEQUENCE: 52

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Val Ser Ser Ala
            20                  25                  30
Val Ala Trp Tyr Gln Gln Lys Pro Gly Lys Ala Pro Lys Leu Leu Ile

```
                    35                  40                  45
        Tyr Ser Ala Ser Ser Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
        65                  70                  75                  80

Glu Asp Phe Ala Thr Tyr Tyr Cys Gln Gln Trp Ser Tyr Tyr Pro Ile
                        85                  90                  95

Thr Phe Gly Gln Gly Thr Lys Val Glu Ile Lys Arg Thr Val Ala Ala
                    100                 105                 110

Pro Ser Val Phe Ile Phe Pro Pro Ser Asp Ser Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                195                 200                 205

Phe Asn Arg Gly Glu Cys Gly Gly Ser Asp Tyr Lys Asp Asp Asp Asp
            210                 215                 220

Lys
        225

<210> SEQ ID NO 53
<211> LENGTH: 693
<212> TYPE: DNA
<213> ORGANISM: Artificial Sequence
<220> FEATURE:
<223> OTHER INFORMATION: Synthetic Construct

<400> SEQUENCE: 53
gaggttcagc tggtggagtc tggcggtggc ctggtgcagc caggggctc actccgtttg      60 tcctgtgcag cttctggctt caacctctat tcttcttcta tgcactgggt gcgtcaggcc     120
ccgggtaagg gcctggaatg ggttgcatct atttatcctt attctggcta tacttattat     180
gccgatagcg tcaagggccg tttcactata agcgcagaca catccaaaaa cacagcctac     240
ctacaaatga acagcttaag agctgaggac actgccgtct attattgtgc tcgctacccg     300
ttcggtgttt ctgcttacta cgctatggac tactggggtc aaggaaccct ggtcaccgtc     360
tcctcggcct ccaccaaggg tccatcggtc ttcccctgg cacccctctc caagagcacc     420
tctgggggca gcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtcga caagaaagtt     660
gagcccaaat cttgtgacaa aactcacaca taa                                   693

<210> SEQ ID NO 54
<211> LENGTH: 230
<212> TYPE: PRT
<213> ORGANISM: Artificial Sequence
<220> FEATURE:
<223> OTHER INFORMATION: Synthetic Construct
```

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Ser
            20                  25                  30

Ser Met His Trp Val Arg Gln Ala Pro Gly Lys Gly Leu Glu Trp Val
        35                  40                  45

Ala Ser Ile Tyr Pro Tyr Ser Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Pro Phe Gly Val Ser Ala Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr
225                 230

<210> SEQ ID NO 55
<211> LENGTH: 675
<212> TYPE: DNA
<213> ORGANISM: Artificial Sequence
<220> FEATURE:
<223> OTHER INFORMATION: Synthetic Construct

<400> SEQUENCE: 55
gatatccaga tgacccagtc cccgagctcc ctgtccgcct ctgtgggcga tagggtcacc      60
atcacctgcc gtgccagtca gtccgtgtcc agcgctgtag cctggtatca acagaaacca     120
ggaaaagctc cgaagcttct gatttactcg gcatccagcc tctactctgg agtcccttct     180
cgcttctctg gtagccgttc cgggacggat ttcactctga ccatcagcag tctgcagccg     240
gaagacttcg caacttatta ctgtcagcaa tcttactggc tgatcacgtt cggacagggt     300
accaaggtgg agatcaaacg aactgtggct gcaccatctg tcttcatctt cccgccatct     360
gattcacagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgaaaa acataaagtc tacgcctgcg aagtcaccca tcagggcctg     600
agctcgcccg tcacaaagag cttcaacagg ggagagtgtg gtggttctga ttacaaagat     660
gacgatgaca aataa                                                              675

<210> SEQ ID NO 56
<211> LENGTH: 224
<212> TYPE: PRT
<213> ORGANISM: Artificial Sequence
<220> FEATURE:
<223> OTHER INFORMATION: Synthetic Construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Trp Leu Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Ser Asp Tyr Lys Asp Asp Asp Asp Lys
    210                 215                 220

<210> SEQ ID NO 57
<211> LENGTH: 28
<212> TYPE: PRT
<213> ORGANISM: Artificial Sequence
<220> FEATURE:
<223> OTHER INFORMATION: Synthetic Construct

<400> SEQUENCE: 57

Cys Pro Pro Leu Met Leu Tyr Asn Pro Thr Thr Tyr Gln Met Asp Val
1               5                   10                  15

Asn Pro Glu Gly Lys Tyr Ser Phe Gly Ala Thr Cys
            20                  25

<210> SEQ ID NO 58
<211> LENGTH: 15
<212> TYPE: PRT
<213> ORGANISM: Artificial Sequence
<220> FEATURE:
<223> OTHER INFORMATION: Synthetic Construct -continued

```
<400> SEQUENCE: 58

Thr Val Arg Gly Ser Lys Lys Pro Tyr Phe Ser Gly Trp Ala Met
1               5                   10                  15
```

EGFR-BINDING AGENTS AND USES THEREOF

RELATED APPLICATIONS

This disclosure is a national phase entry of PCT/CA2018/050202 filed Feb. 22, 2018 (which designates the U.S.), which claims the benefit of priority to U.S. provisional application No. 62/462,175 filed Feb. 22, 2017, which is incorporated herein by reference in its entirety.

INCORPORATION OF SEQUENCE LISTING

A computer readable form of the Sequence Listing "13764-P41788US02_SequenceListing.txt" (49,152 bytes), submitted via EFS-WEB and created on Aug. 21, 2019, is herein incorporated by reference.

FIELD

This disclosure relates generally to EGFR-binding agents, and to methods and uses of these binding agents.

BACKGROUND

Antibody leads for engineering antibody-based therapeutics have been developed primarily using natural immune repertoires (Aboud-Pirak et al., 1988, Knight et al., 1993, Presta et al, 1997), but synthetic antibody technology offers an attractive alternative (Schaefer et al., 2011, Wu et al., 2010). The compatibility of synthetic antibody engineering with established combinatorial phage display techniques enables unprecedented opportunities for engineering specificity by controlling antibody sequences that mediate antigen recognition.

Protein-protein interactions (PPIs) mediate a myriad of biological functions and insights in to their structural basis can aid in the design and engineering of antibodies capable of modulating protein activities. PPIs are mediated by a variety of motifs, including small linear peptide segments (Pierschbacher and Ruoslahti, 1984), discrete domains (Pawson and Nash, 2003, Garrett et al., 2002), binding sites (Syed et al., 1998) and more complex epitopes (Aragues et al., 2007). Knowledge of these features have been exploited to rationally design antibodies with non-natural binding profiles and activities by grafting elements responsible for binding in to complementarity determining regions (CDRs) (Perchiacca et al., 2012, Barbas et al., 1993, Lee et al., 2007). These studies underscore the plasticity of CDRs in tolerating sequence and length diversity and serve as examples of rational approaches for designing antibodies that bind specific targets.

EGFR is a member of the ErbB family of cell-surface receptor tyrosine kinases (RTKs), which govern cellular growth, differentiation and apoptosis (Lemmon et al., 2014), and when dysregulated, play a central role in the aberrant growth, cellular turnover and migration processes of many cancers (Huang et al., 2012, Wang et al., 2011). EGFR over-expression is known to drive a subset of cancers and is a validated target for antibodies that have been shown to improve clinical outcomes (Bonner et al., 2006, Moroni et al., 2005). Despite the effectiveness of existing anti-EGFR therapeutic antibodies, both intrinsic and acquired resistance mechanisms contribute to their therapeutic limitations (Brand et al., 2014, Konieczkowski et al., 2013). In light of this, there is interest in developing novel antibodies that target different epitopes and possess mechanisms of action distinct from those in clinical use.

SUMMARY

The present inventors have identified novel EGFR-binding antibody variable regions that, when incorporated into antibodies and Fabs, enable these to recognize EGFR. The inventors used the dimerization loop motif of EGFR to design and construct a structure-directed, phage-displayed Fab library biased toward binding EGFR domain II. The entire dimerization loop sequence was grafted so as to replace a segment of the CDR-H3 of a human Fab and other CDRs, and certain framework residues were diversified. This phage-displayed Fab library was used in binding selections with EGFR, and for comparison, a previously validated naïve synthetic Fab library was also screened. Both libraries yielded Fabs with nanomolar dissociation constants that blocked ligand-induced receptor activation, and the epitopes of both Fabs mapped to EGFR domains I and II and did not overlap with epitopes of therapeutic anti-EGFR monoclonal antibodies (mAbs). Inhibition of breast cancer and colon cancer cell lines by Fabs disclosed herein was also shown.

Accordingly, the present disclosure provides an EGFR-binding agent which specifically binds to an epitope wholly or partly within domain I and/or domain II of EGFR.

In one embodiment, the binding agent does not bind domain III of EGFR.

In another embodiment, the binding agent comprises an antibody variable region that specifically binds human EGFR.

In another embodiment, the EGFR binding agent comprises:

(i) an antibody variable region comprising a light chain complementarity determining region (CDR)1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 11; and optionally further comprising an isoleucine at residue 39 of the VH domain, a tyrosine at residue 55 of the VH domain and a tyrosine at residue 66 of the VH domain, (ii) an affinity matured derivative of the EGFR binding agent set out in (i), or (iii) an antibody variable region comprising a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 5 and a heavy chain CDR1 comprising the amino acid sequence of amino acids 1-8 of SEQ ID NO: 8, a heavy chain CDR2 comprising the amino acid sequence of amino acids 2-9 of SEQ ID NO: 10, and a heavy chain CDR3 comprising the amino acid sequence of SEQ ID NO: 1636 and optionally further comprises a methionine at residue 39 of the VH domain, a serine at residue 55 of the VH domain and a tyrosine at residue 66 of the VH domain.

In another embodiment, the affinity matured derivative comprises:

(a) an antibody variable region comprising a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 4 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 12 and optionally further comprising an isoleucine at residue 39 of the VH domain, a tyrosine at residue 55 of the VH domain and a tyrosine at residue 66 of the VH domain;

(b) an antibody variable region comprising a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 13, and optionally further comprising an isoleucine at residue 39 of the VH domain, a tyrosine at residue 55 of the VH domain and a tyrosine at residue 66 of the VH domain, (c) an antibody variable region comprising a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 14 and optionally further comprising an isoleucine at residue 39 of the VH domain, a tyrosine at residue 55 of the VH domain and a tyrosine at residue 66 of the VH domain, or (d) an antibody variable region comprising a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 7, a heavy chain CDR2 comprising the amino acid sequence of amino acids 2-9 of SEQ ID NO: 9, and a heavy chain CDR3 comprising the amino acid sequence of SEQ ID NO: 15 and optionally further comprising an isoleucine at residue 39 of the VH domain, a tyrosine at residue 55 of the VH domain and a tyrosine at residue 66 of the VH domain.

In another embodiment, the binding agent is selected from the group consisting of an antibody, an antibody fragment, a single-chain Fv (scFv), a bispecific antibody, a phage-Fab and a phage-scFv.

In another embodiment, the binding agent is a fragment antigen-binding (Fab).

In another embodiment, the EGFR-binding agent comprises human antibody constant regions.

In another embodiment, the EGFR-binding agent is an IgG molecule.

In another embodiment, the binding agent is labelled with a detection agent.

The disclosure also provides a conjugate comprising (1) a binding agent as described herein attached to (2) an effector agent.

In one embodiment, the effector agent is an anti-neoplastic agent.

In another embodiment, the effector agent is a toxin.

The disclosure also provides pharmaceutical composition comprising an EGFR-binding agent as described herein or a conjugate as described herein and a carrier.

The disclosure also provides a use of an EGFR-binding agent as described herein, a conjugate as described herein or a pharmaceutical composition as described herein for targeting EGFR-expressing cells.

The disclosure also provides a use of an EGFR-binding agent as described herein, a conjugate as described herein or a pharmaceutical composition as described herein for binding EGFR-expressing cells.

The disclosure also provides a use of an EGFR-binding agent as described herein, a conjugate as described herein or a pharmaceutical composition as described herein for detecting EGFR-expressing cells and/or for quantitating levels of cellular EGFR expression.

The disclosure also provides a use of an EGFR-binding agent as described herein, a conjugate as described herein or a pharmaceutical composition as described herein for reducing levels of EGFR protein in EGFR-expressing cells.

In one embodiment, the EGFR-expressing cells are cancer cells.

In another embodiment, the cancer cells are breast cancer cells or colon cancer cells.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

DRAWINGS

Embodiments are described below in relation to the drawings in which.

Figure 10:
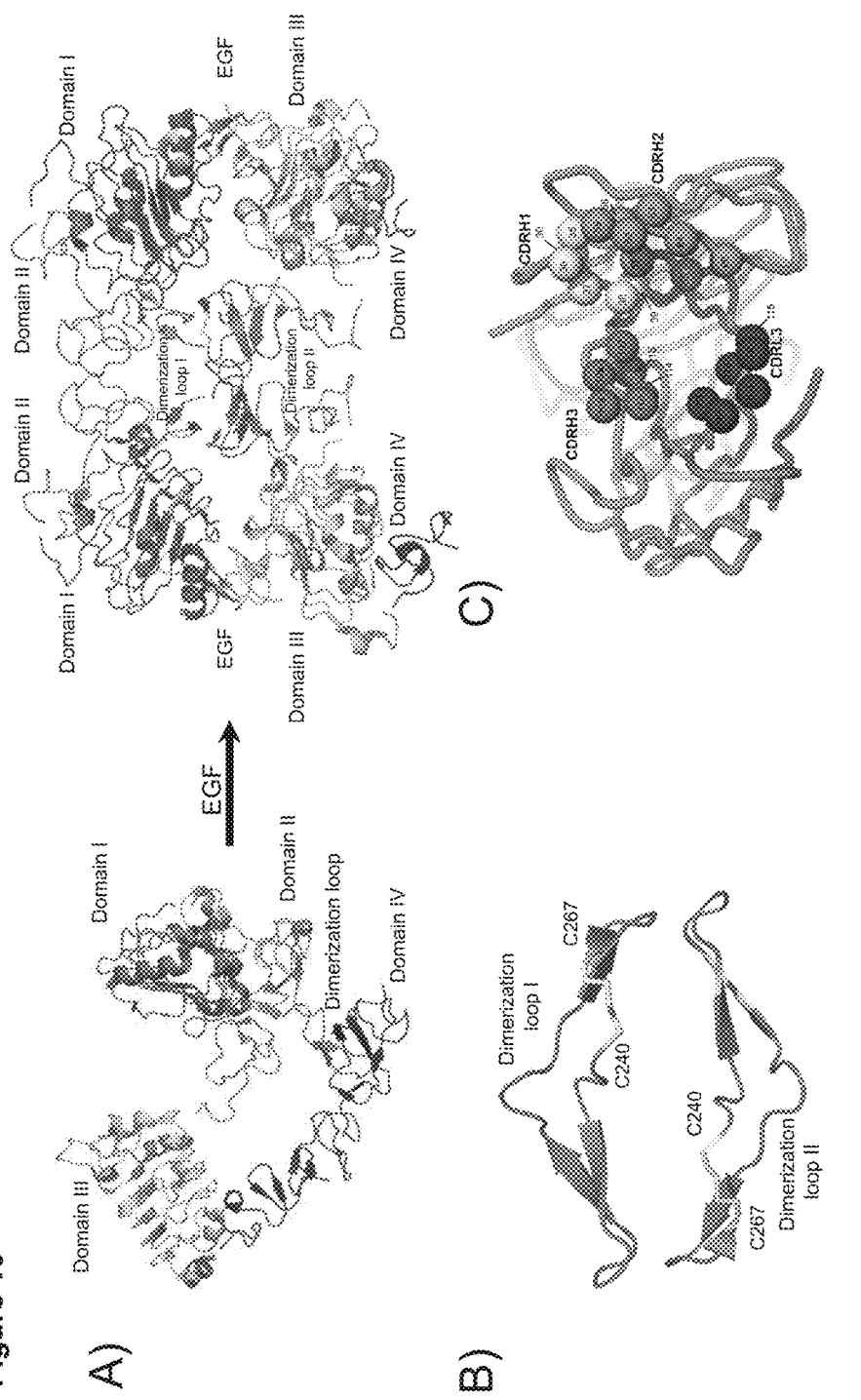

FIG. 10 shows the library design and selection library-variable CDR and FR residues of anti-EGFR Fabs. A) Conformation of the auto-inhibited, tethered EGF receptor is maintained by interaction between domains II and IV. Ligand binding induces a major structural rearrangement that exposes a 28-residue dimerization loop (residues C240-C267) in domain II. B) The dimerization loop makes extensive intermolecular interactions with the dimerization loop in a partner receptor, which are essential for dimerization, activation and signaling. C) The loops subjected to diversification in the Fab libraries. Spheres represent residues that were diversified for certain residues of CDR-H3, CDR-H1 CDR-H2, CDR-L3, and framework residues at IMGT positions 39, 55 and 66 (numbered and labeled). A representative structure is shown from the crystal coordinates of a scFv (PDB entry 1FVC) that has a framework very similar to that used in the synthetic Fab libraries. D) Selection library-variable CDR and FR residues of anti-EGFR Fabs isolated from the structure-directed library (DL06 and 8708) or Library F (8709). Mutations arising in Fab 8708 from affinity maturation of Fab DL06 are shaded grey. Residues are numbered according to IMGT standards (Lefranc et al., 2003).

Figure 11:
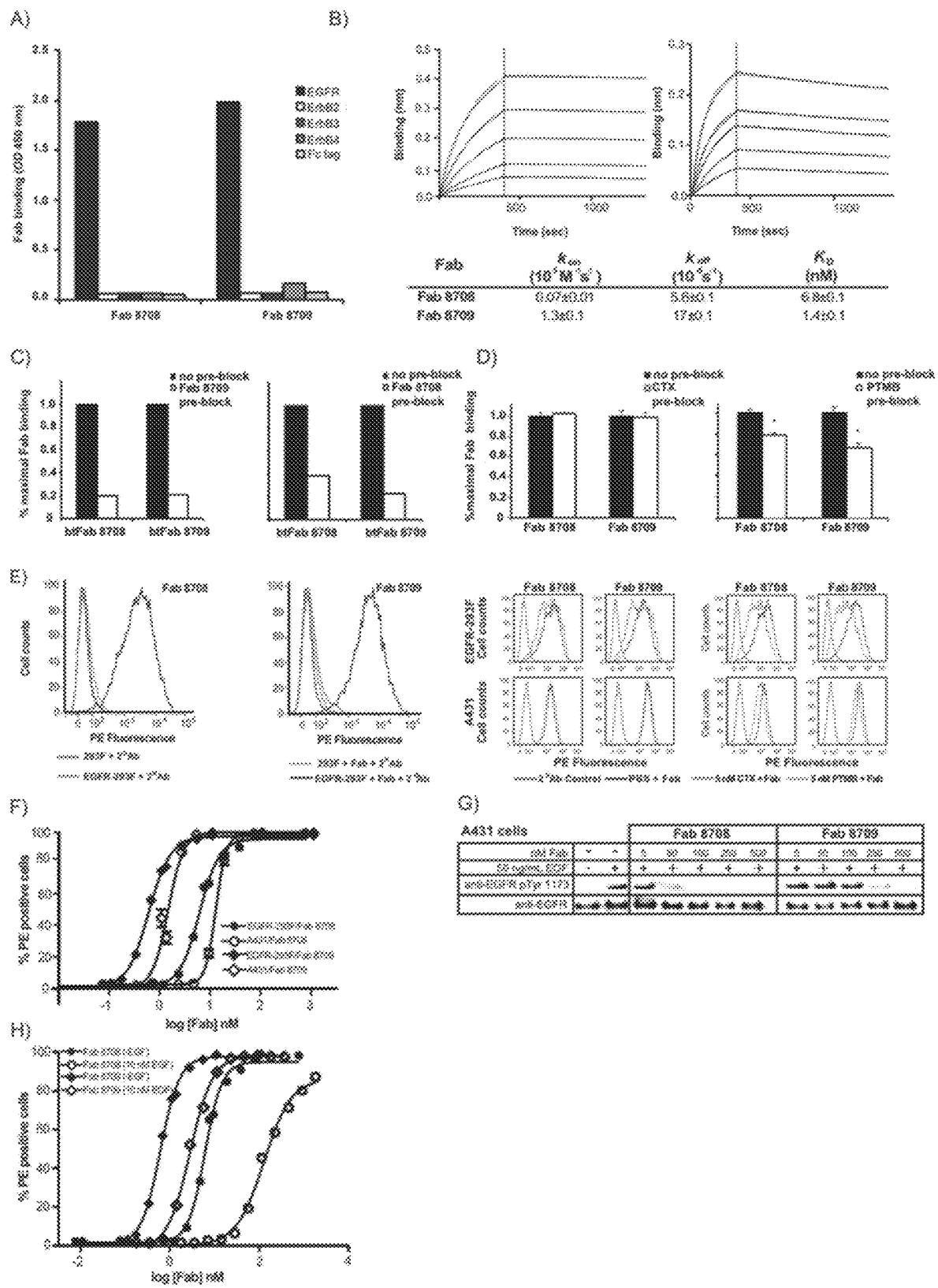

FIG. 11 shows a characterization of anti-EGFR Fabs. A) Fab specificity for ErbB family members by ELISA. B) Biolayer interferometry sensorgram traces for binding of rhEGFR to immobilized Fab 8708 (left panel) or Fab 8709 (right panel). The derived kinetic constants with errors are shown below the curves. C) ELISA for detection of biotinylated Fabs (x-axis) binding to immobilized rhEGFR pre-blocked with the indicated non-biotinylated Fab. D) ELISA (top) or flow cytometry (bottom) analysis of Fab binding to immobilized rhEGFR-ECD or cells (EGFR-293F and A431), respectively, blocked with CTX or PTMB, as indicated. E) Flow cytometry analysis of Fab 8708 (left) or Fab 8709 (right) binding to EGFR-293F and 293F cells. F) Dose response curves for Fab 8708 and Fab 8709 binding to EGFR-293F and A431 cells by flow cytometry. G) Western blots of cell lysates from A431 carcinoma cells pre-incubated with Fab prior to stimulation with EGF. Blots were developed with an anti-phospho-Tyr1173 antibody or anti-EGFR antibody as load control. H) Dose response curves obtained by flow cytometric measurement of Fab binding to A431 cells following incubation with 10 nM EGF.

Figure 12:
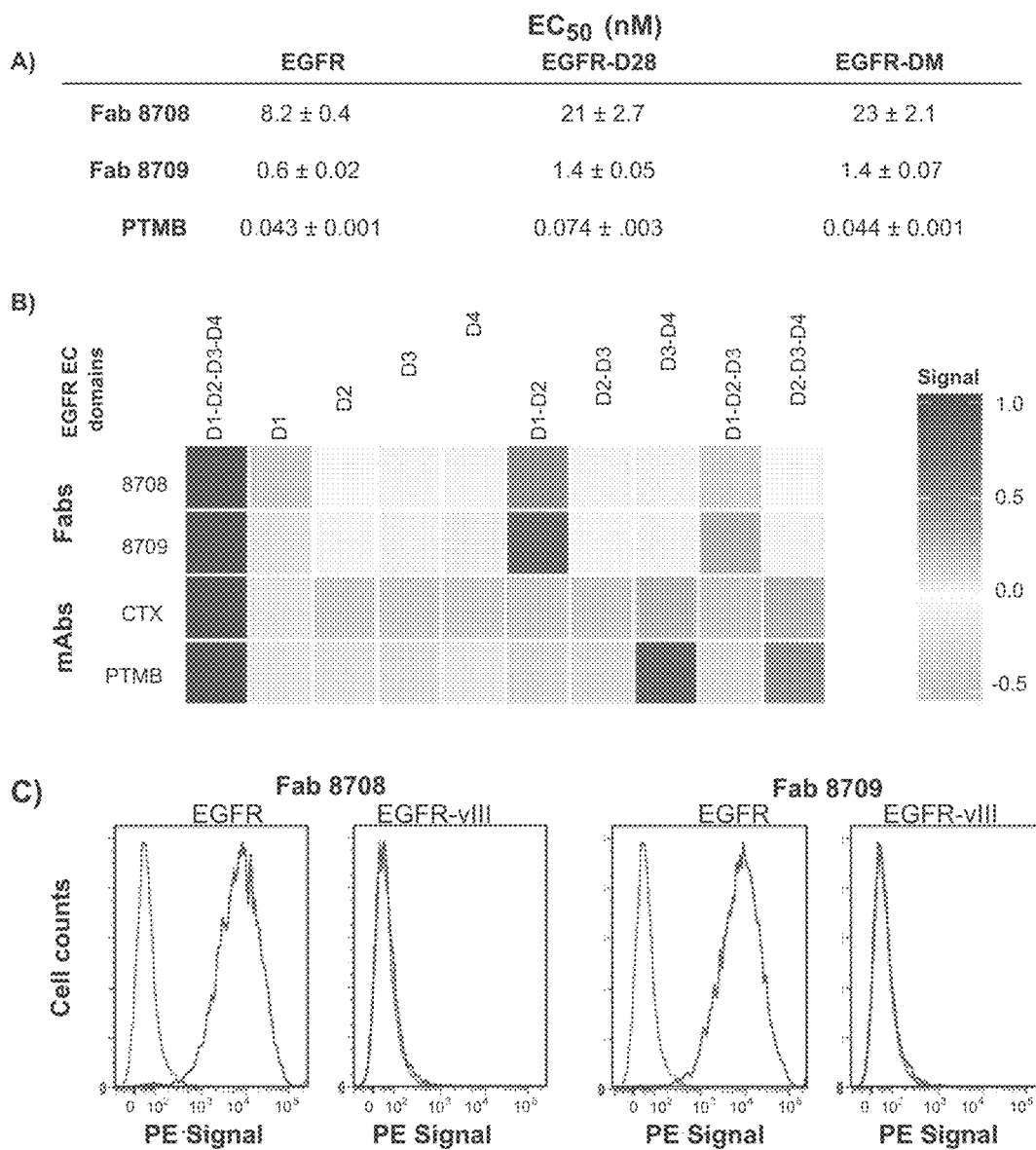

FIG. 12 shows epitope mapping of antibodies binding to EGFR variants. A) $EC_{50}$ values determined by flow cytometry for antibodies binding to HEK293F cells transiently expressing EGFR, EGFR-D28 or EGFR-DM (See also FIG. 14) B) Heat map for flow cytometry measurements of relative binding of antibodies to 293F cells expressing the indicated domains of the EGFR ECD. C) Flow cytometry of 200 nM Fab binding to HEK293F cells transiently expressing either EGFR or EGFR-vIII (dark grey trace) compared with binding to HEK293F cells transiently expressing GFP (light grey trace).

Figure 13:
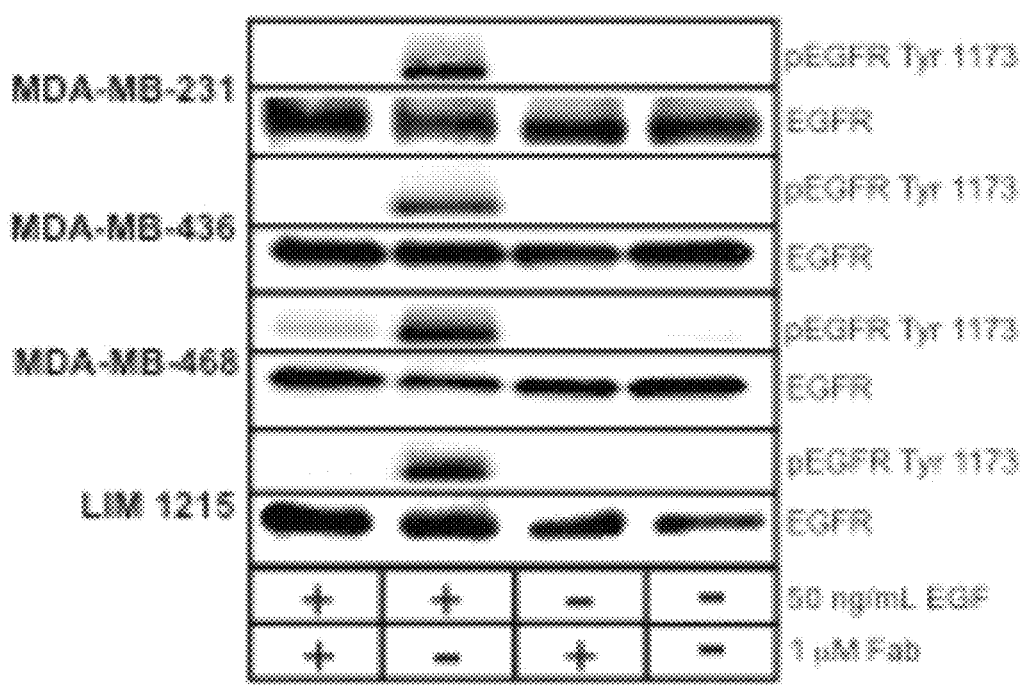

FIG. 13 shows inhibition of the colon carcinoma cell line LIM1215 by affinity matured DL06 clone Fab 8708.

Figure 14:
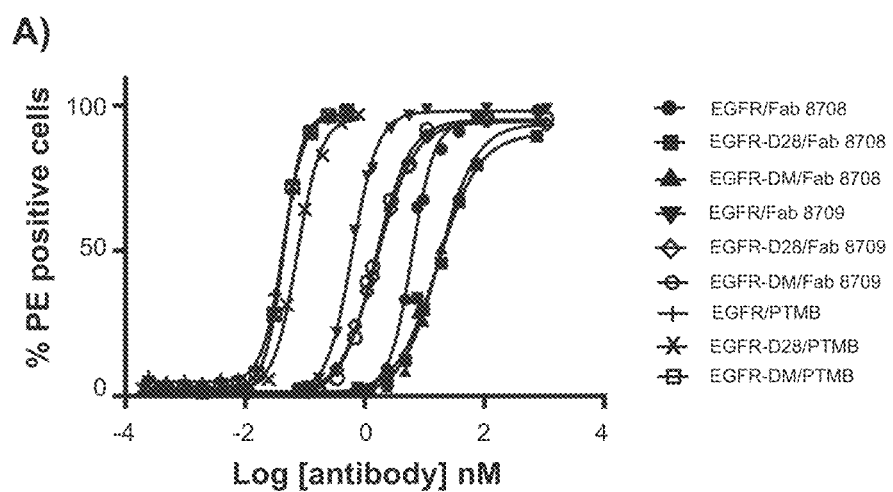

FIG. 14 shows Fab and mAb binding curves to dimerization loop mutants. Fab and control mAb binding to 293F cells transfected with EGFR, EGFR-D28 or EGFR-DM was evaluated by flow cytometry. The % of PE-labeled cells were plotted versus log[antibody] and curves fit to resolve changes in half-maximal binding.

Figure 15:
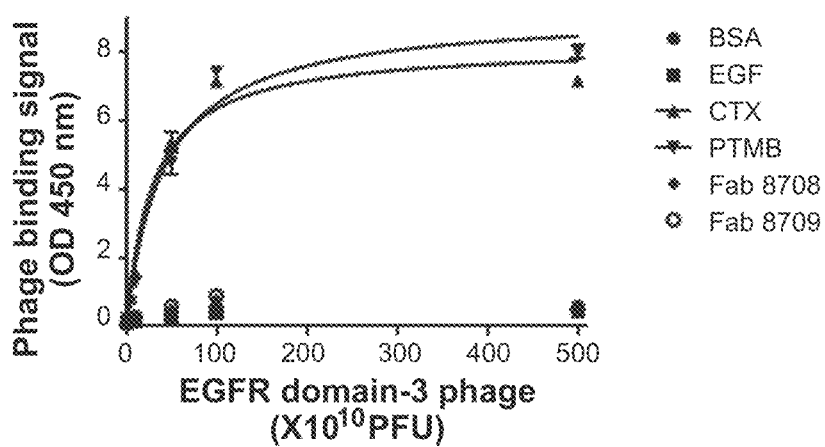

FIG. 15 shows an absence of Fab binding to EGFR domain III. Phage-displayed EGFR domain III binding to plate immobilized Fab, mAb and protein controls was quantified by ELISA.

Figure 16:
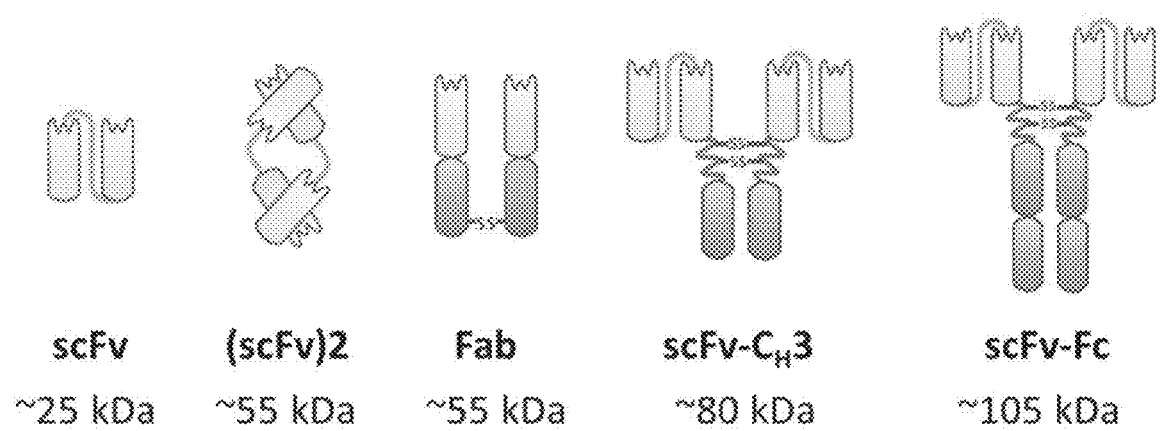

FIG. 16 shows DL06 Fab (middle) formatted into an scFv, (scFv)2, scFv-CH3 and scFv-Fc.

Figure 17:
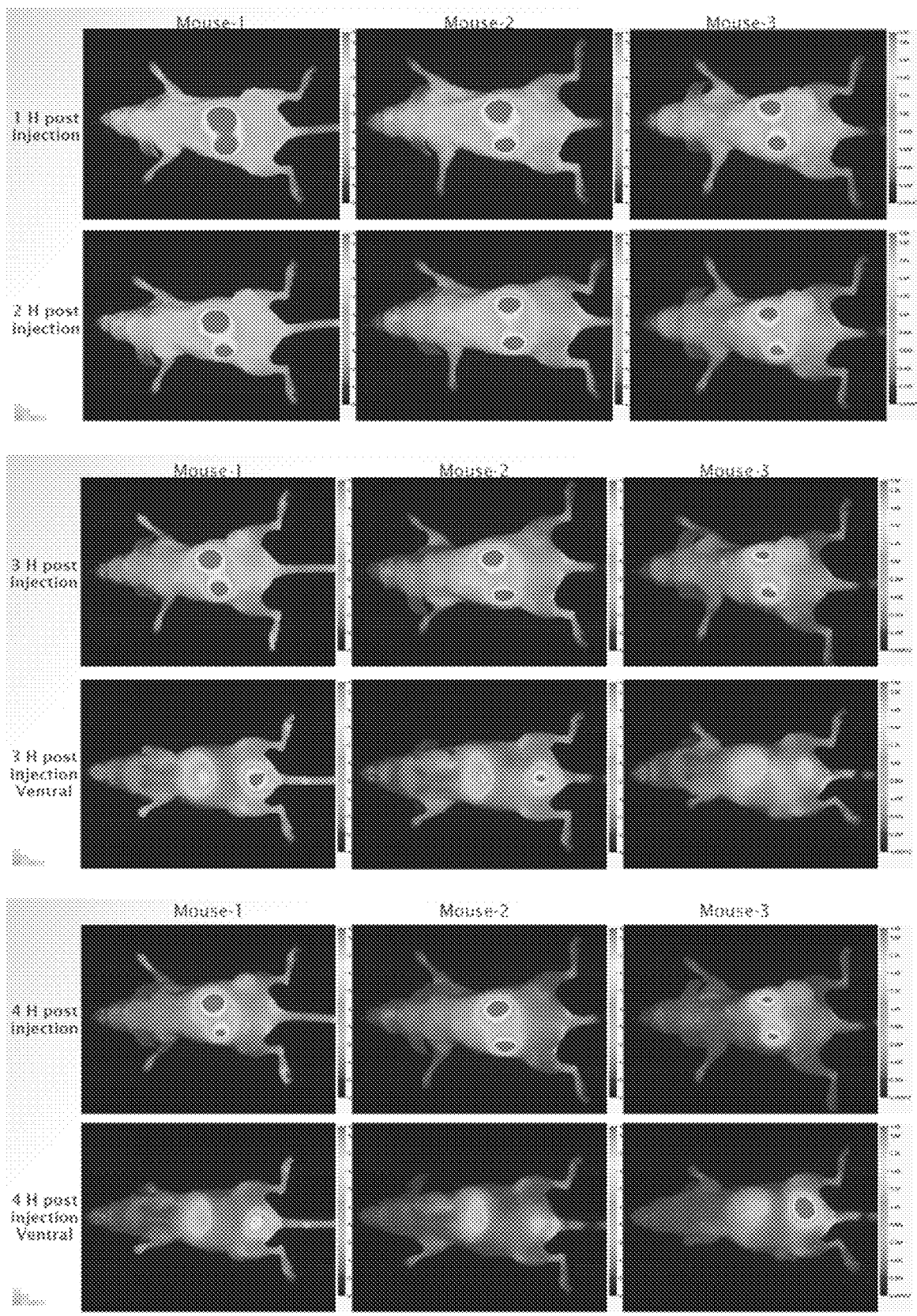

FIG. 17 shows DL06 scFv-800CW biodistribution to mice bearing A431 cell xenografts.

Figure 18:
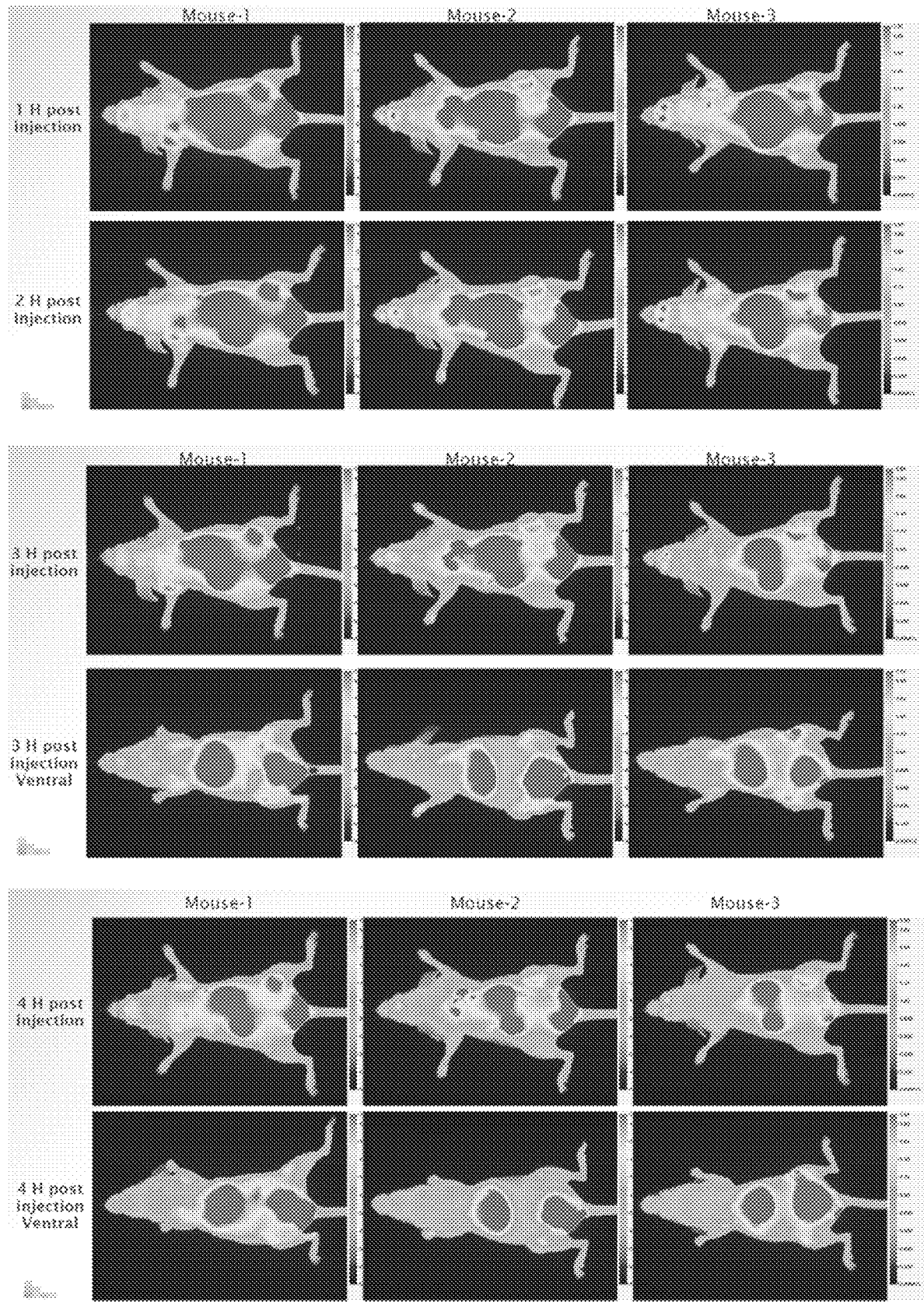

FIG. 18 shows DL06 (scFv)2-800CW biodistribution to mice bearing A431 cell xenografts.

Figure 19:
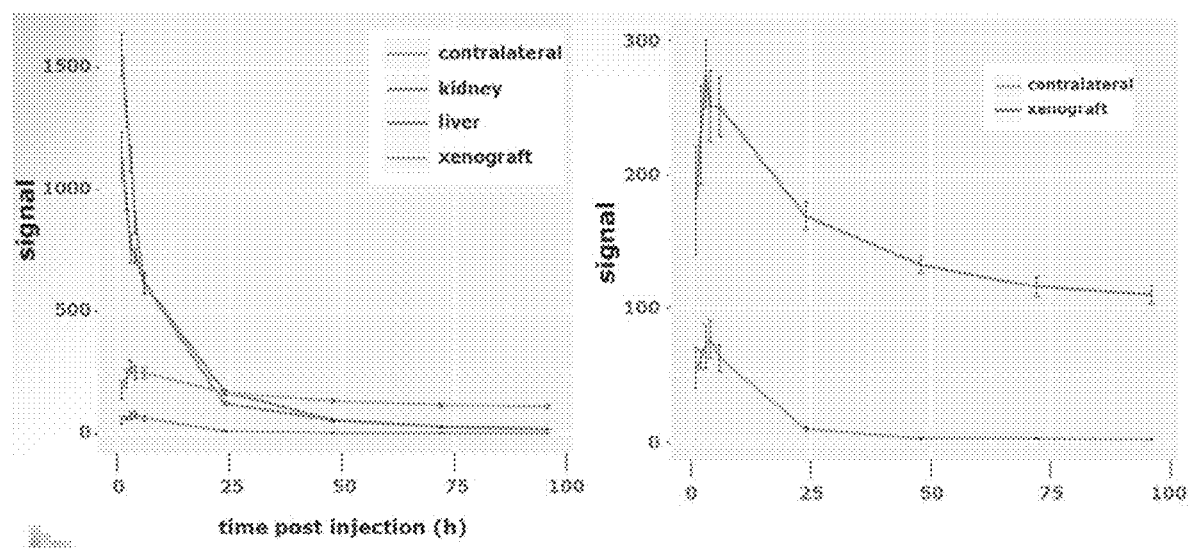

FIG. 19 shows the fluorescence intensity of DL06 (scFv)2-800CW in mice bearing A431 cell xenografts.

Figure 20:
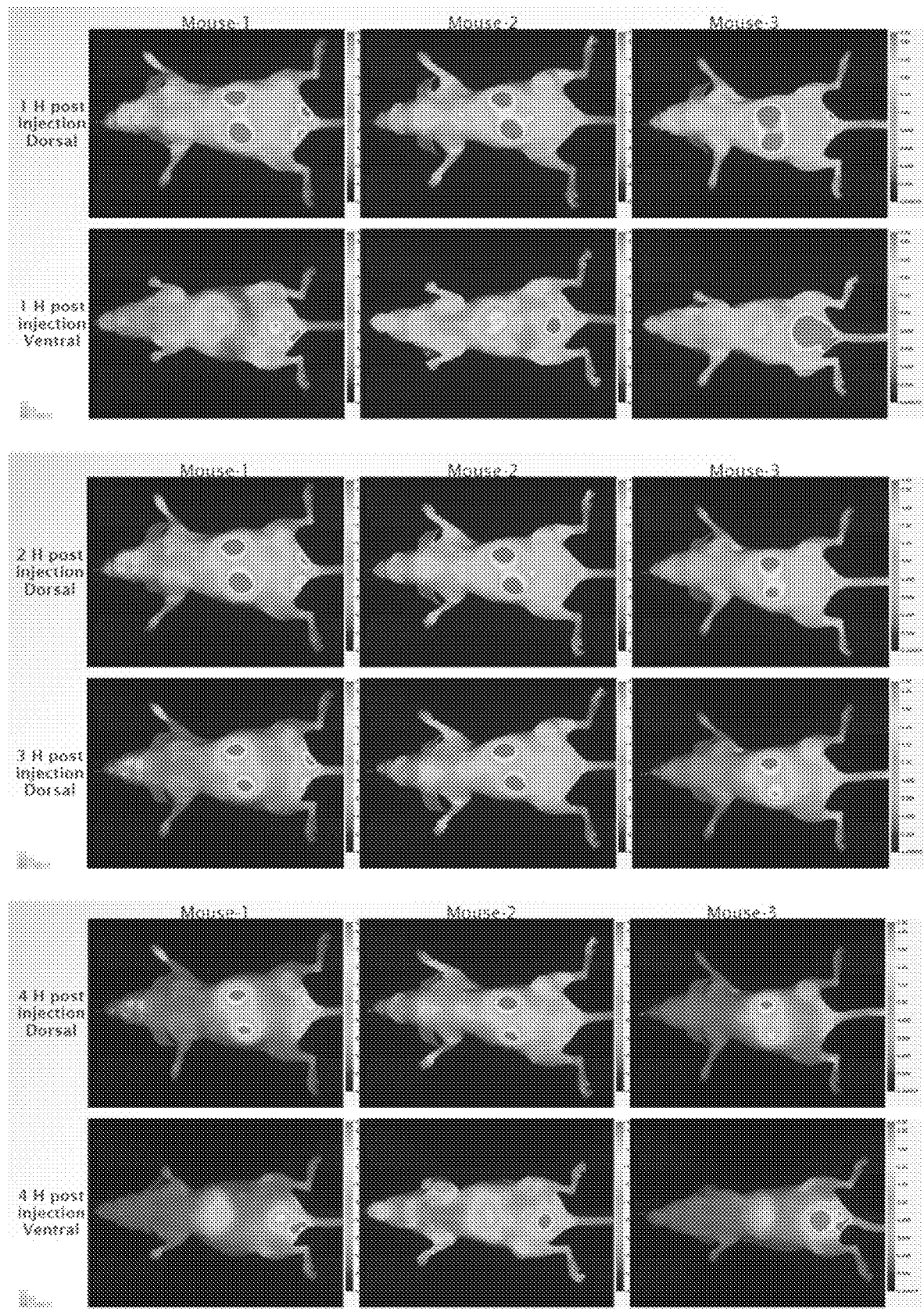

FIG. 20 shows anti-MBP (scFv)2-800CA biodistribution to mice bearing A431 cell xenografts.

Figure 21:
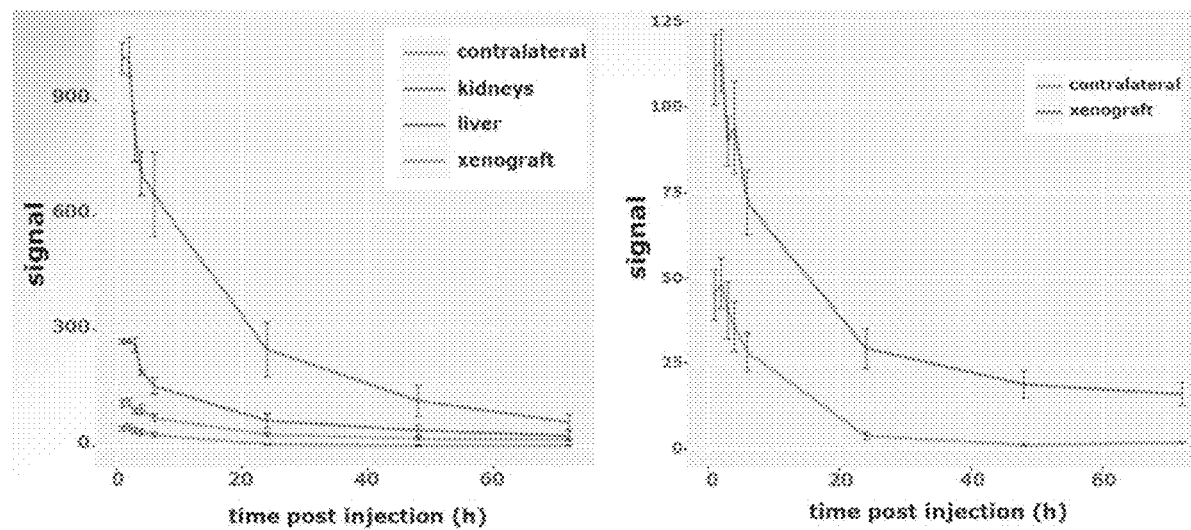

FIG. 21 shows the fluorescence intensity of anti-MBP (scFv)2-800CA in mice bearing A431 cell xenografts.

Figure 22:
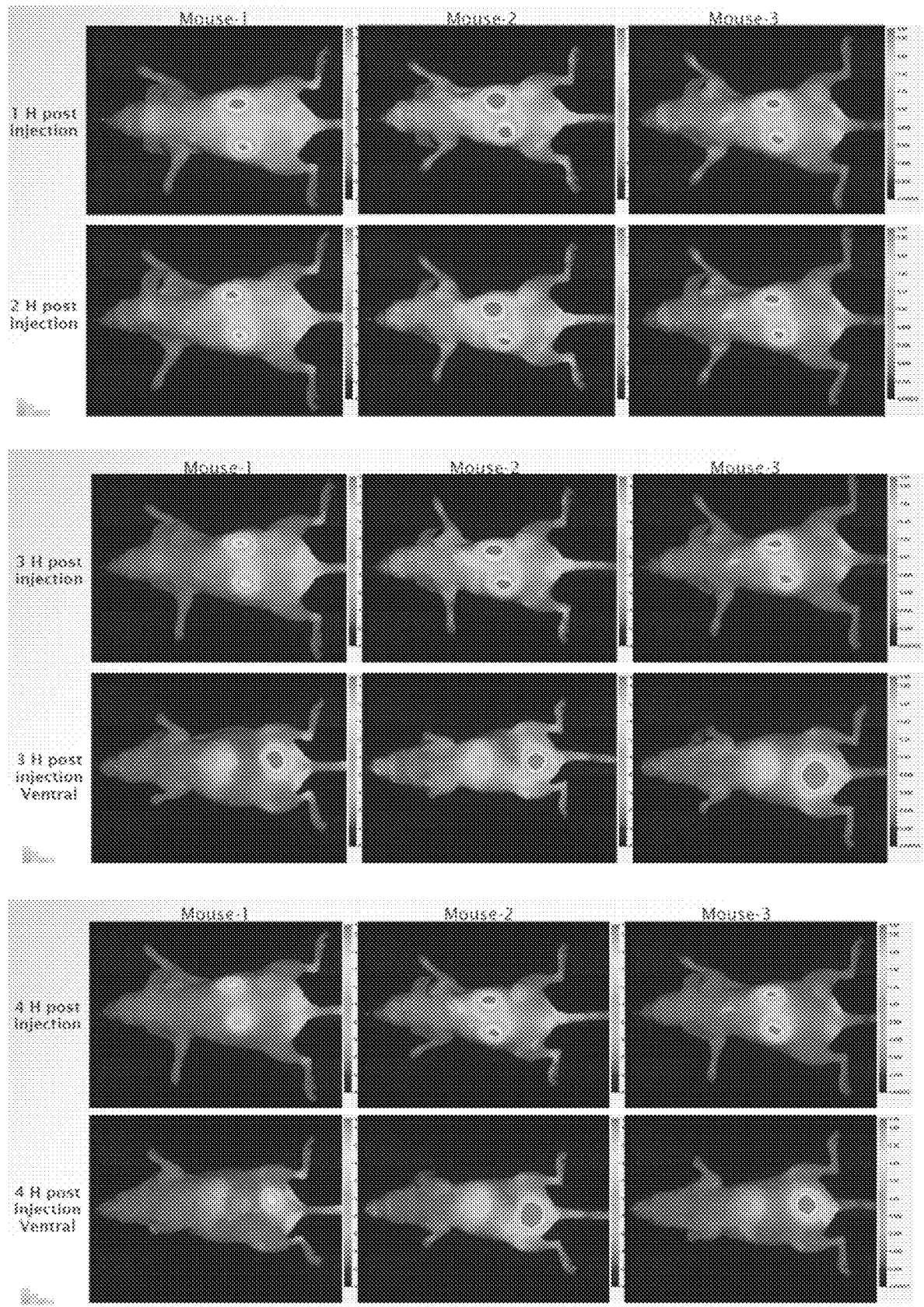

FIG. 22 shows DL06 Fab-800CW biodistribution to mice bearing A431 cell xenografts.

Figure 23:
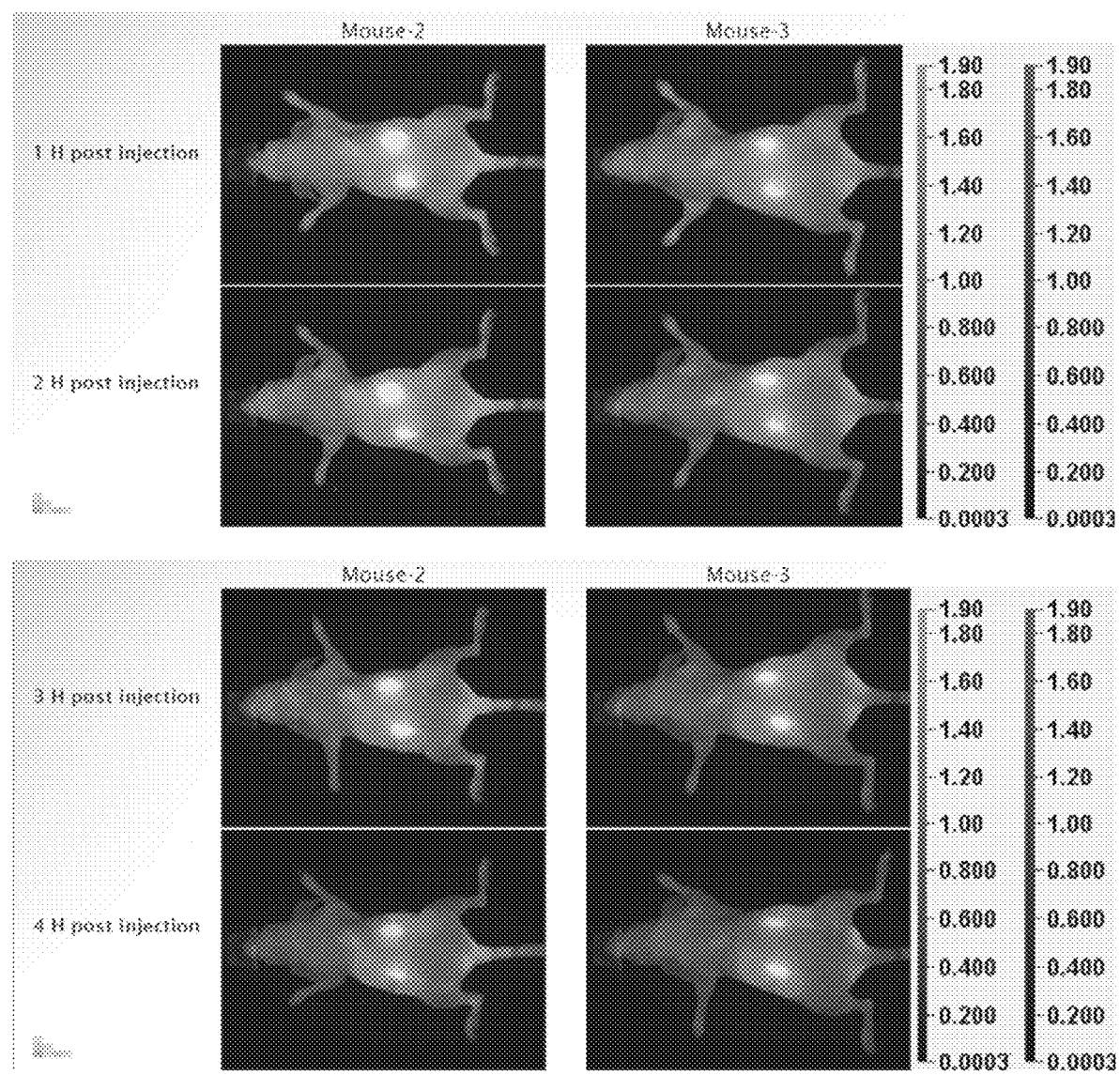

FIG. 23 shows DL06 Fab-800CW+ MBP Fab-680RD biodistribution to mice bearing A431 cell xenografts.

Figure 24:
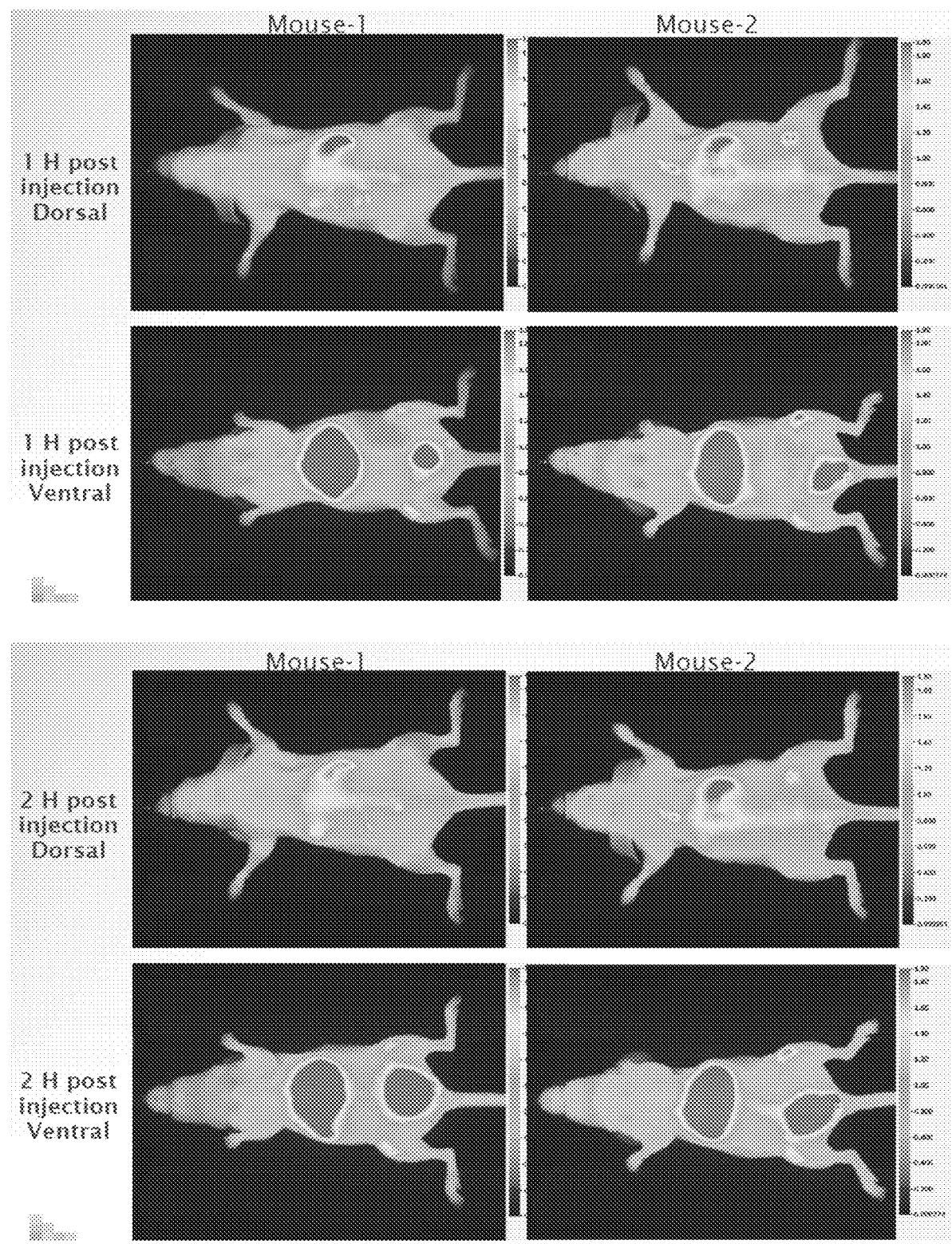

FIG. 24 shows DL06 scFv-CH3-800CW biodistribution to mice bearing A431 cell xenografts.

Figure 25:
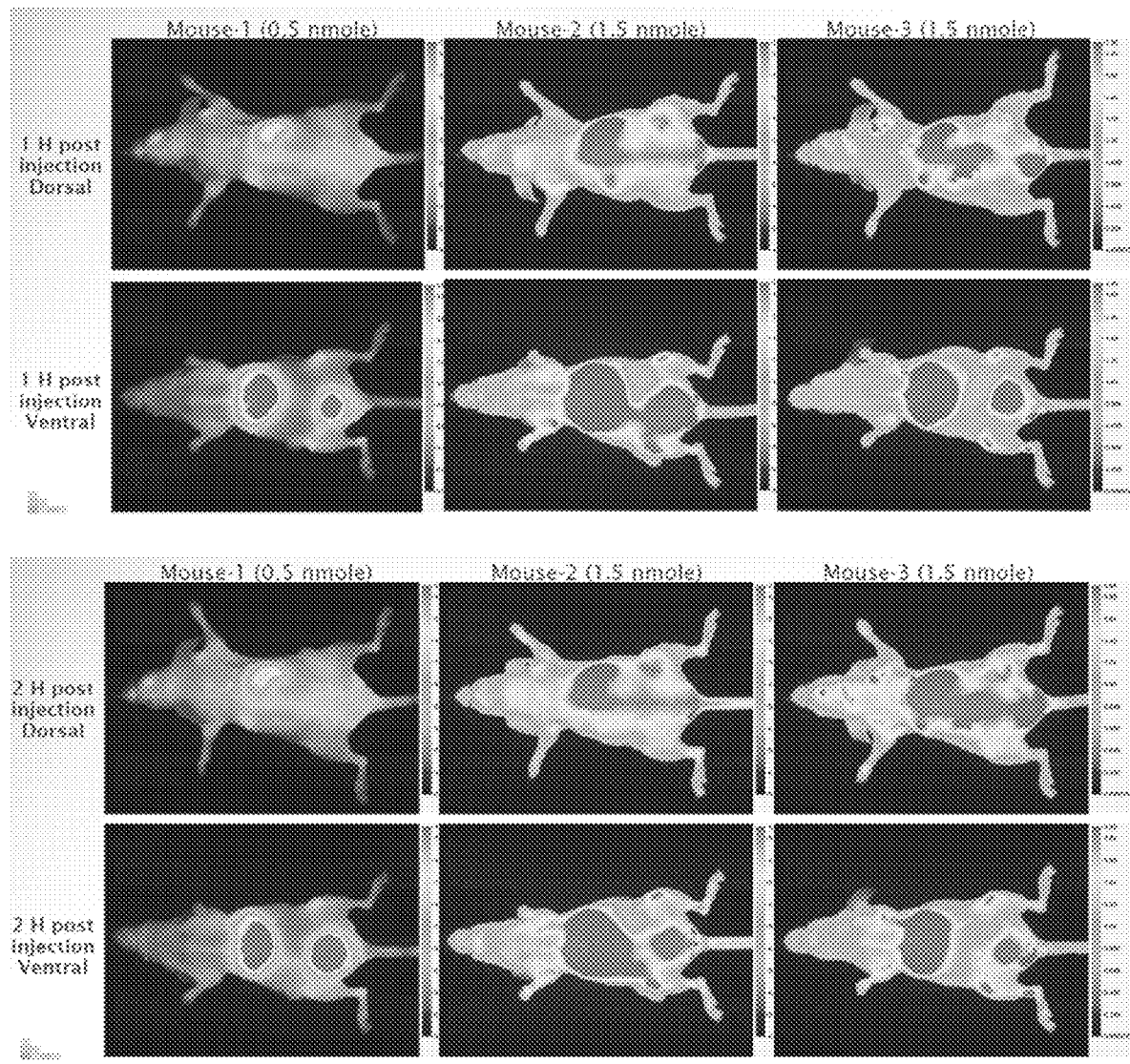

FIG. 25 shows DL06 scFv-Fc-800CW biodistribution to mice bearing A431 cell xenografts.

Figure 26:
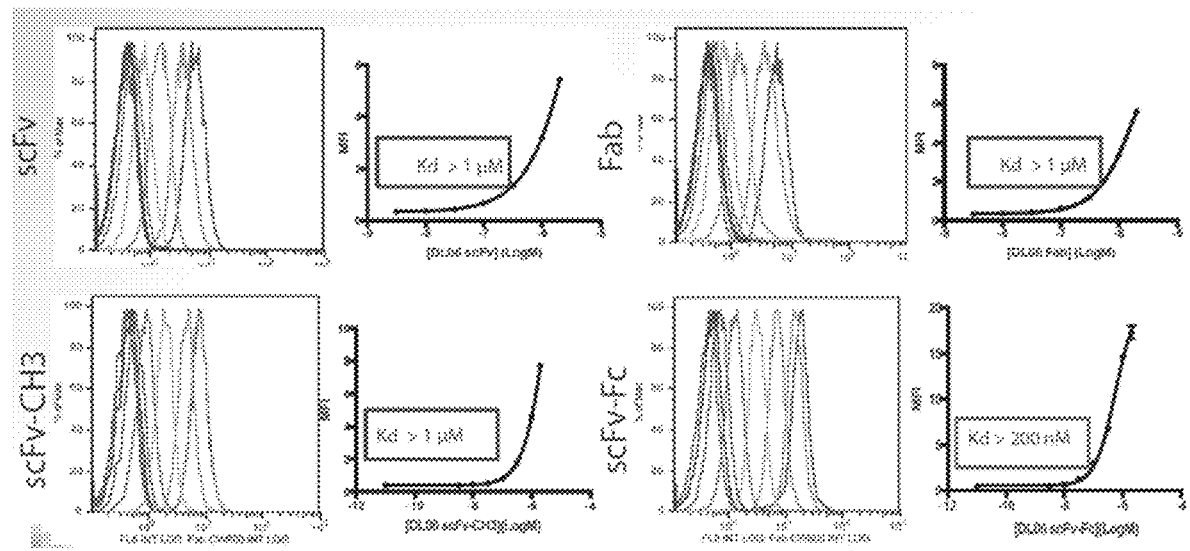

FIG. 26 shows flow cytometry data for DL06 scFv, DL06 Fab, DL06 scFv-CH3 and DL06 scFv-Fc.

Figure 27:
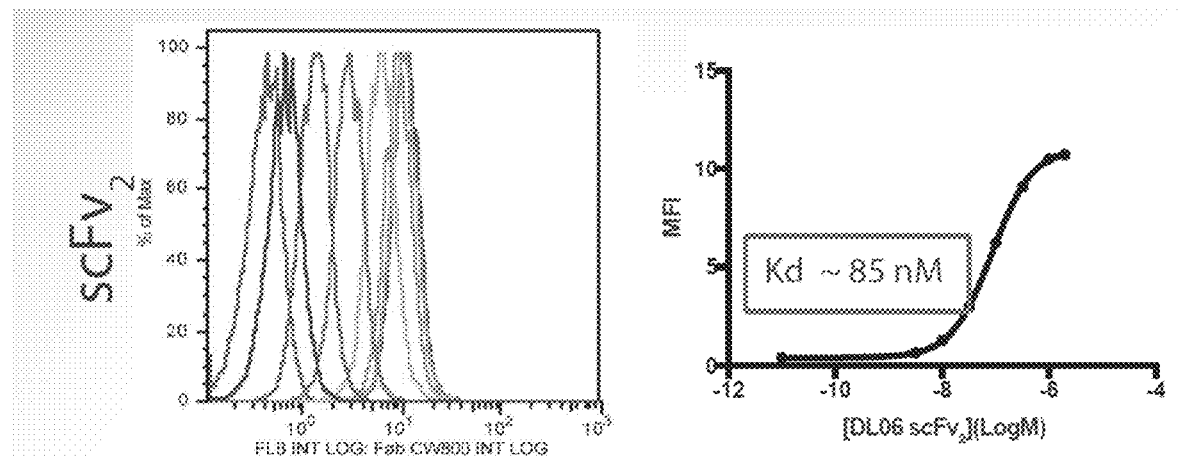

FIG. 27 shows flow cytometry data for DL06 scFv.

Figure 28:
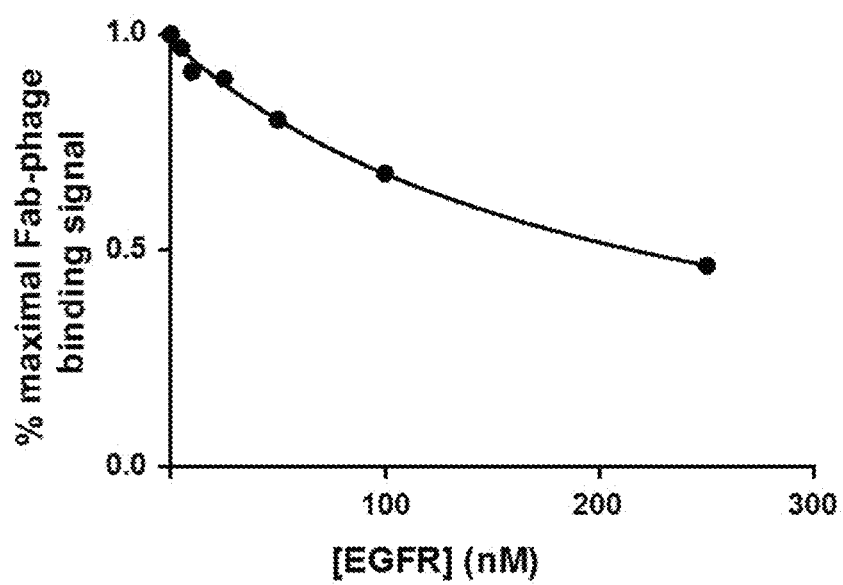

FIG. 28 shows affinity estimation of parent clone DL06 by multipoint competitive phage ELISA. Binding of parent DL06 phage-displayed Fab was assessed to plate immobilized EGFR by competitive ELISA using soluble rhEGFR as competitor. A plot of % maximal binding was generated versus increasing [competitor] and fit to approximate parent clone $IC_{50}$.

Figure 29:
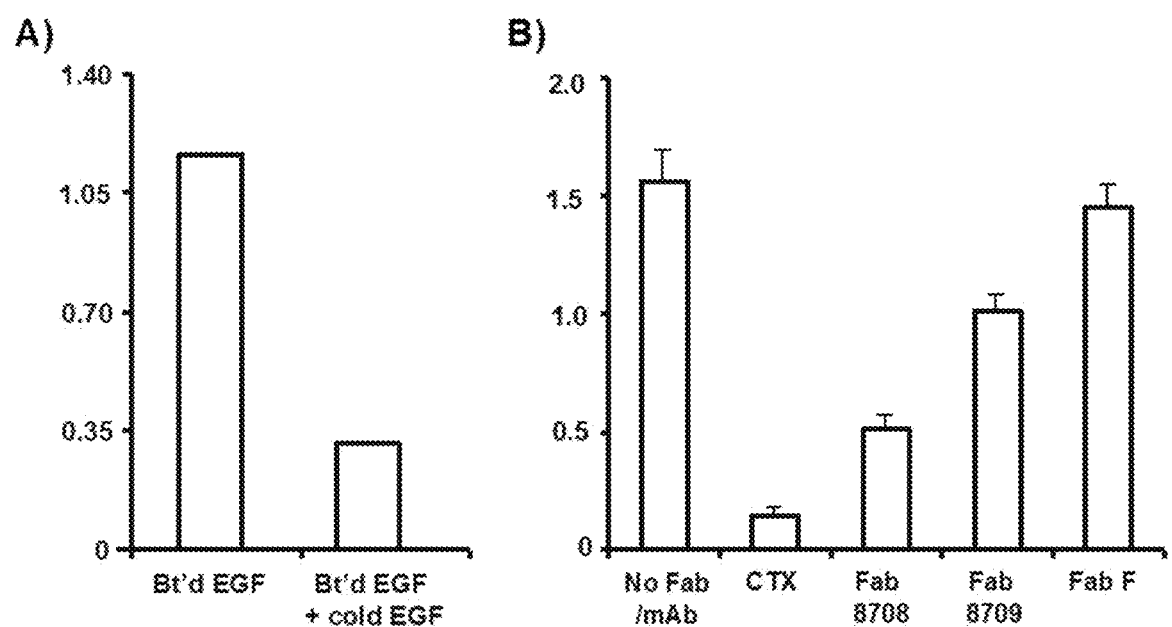

FIG. 29 shows Fab-mediated effects on EGF ligand binding by ELISA. A) Immobilized EGFR pre-incubated with unlabeled EGF effectively blocked binding of biotinylated EGF, establishing the specificity of binding. B) Binding of biotinylated EGF was similarly assessed following pre-incubation 200 nM Fab 8708, 8709 or a neutral EGFR-binding Fab F or CTX as positive control.

Figure 30:
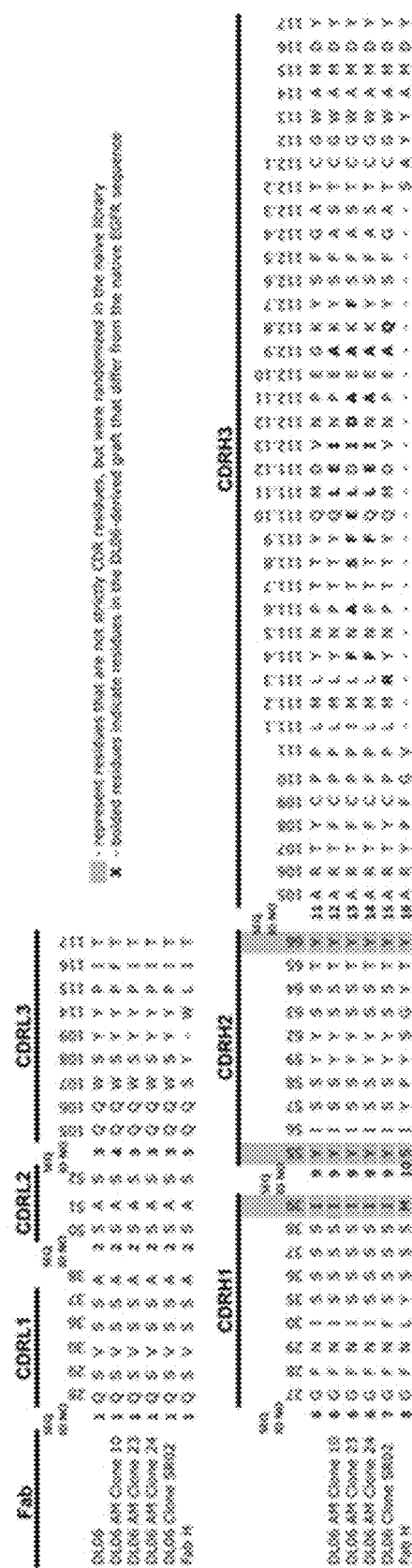

FIG. 30 shows parent and affinity matured clone CDR sequences.

DETAILED DESCRIPTION

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Compositions of Matter:

The present inventors have provided novel antibody variable regions which are capable of specifically binding to domain I and/or domain II of epidermal growth factor receptor (EGFR). When incorporated into Fabs, these antibody variable regions enable the Fabs to bind to EGFR.

The inventors have particularly provided EGFR-binding Fab clone DL06 and its affinity matured derivatives, DL06 AM Clone 10, DL06 AM Clone 23, DL06 AM Clone 24 and DL06 SR02 (also referred to as Fab 8708). The inventors have also particularly provided EGFR-binding clone Fab H (also referred to as Fab 8709). Sequences of the light chain and heavy chain complementarity determining regions (CDRs) of the clones are set out in FIG. 30.

In particular, DL06 comprises a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 11. In another embodiment, DL06 further comprises an isoleucine at residue 39 of the VH domain, a tyrosine at residue 55 of the VH domain and a tyrosine at residue 66 of the VH domain.

In addition, DL06 AM Clone 10 comprises a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 4 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 12. In another embodiment, DL06 AM Clone 10 further comprises an isoleucine at residue 39 of the VH domain, a tyrosine at residue 55 of the VH domain and a tyrosine at residue 66 of the VH domain.

In addition, DL06 AM Clone 23 comprises a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 13. In another embodiment, DL06 AM Clone 23 further comprises an isoleucine at residue 39 of the VH domain, a tyrosine at residue 55 of the VH domain and a tyrosine at residue 66 of the VH domain.

In addition, DL06 AM Clone 24 comprises a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 14. In another embodiment, DL06 AM Clone 24 further comprises an isoleucine at residue 39 of the VH domain, a tyrosine at residue 55 of the VH domain and a tyrosine at residue 66 of the VH domain.

In addition, DL06 SR02 (Fab 8708) comprises a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 7, a heavy chain CDR2 comprising the amino acid sequence of amino acids 2-9 of SEQ ID NO: 9, and a heavy chain CDR3 comprising the amino acid sequence of SEQ ID NO: 15. In another embodiment, DL06 SR02 (Fab 8708) further comprises an isoleucine at residue 39 of the VH domain, a tyrosine at residue 55 of the VH domain and a tyrosine at residue 66 of the VH domain.

In addition, Fab H (Fab 8709) comprises a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 5 and a heavy chain CDR1 comprising the amino acid sequence of amino acids 1-8 of SEQ ID NO: 8, a heavy chain CDR2 comprising the amino acid sequence of amino acids 2-9 of SEQ ID NO: 10, and a heavy chain CDR3 comprising the amino acid sequence of SEQ ID NO: 16. In another embodiment, Fab H (Fab 8709) further comprises an methionine at residue 39 of the VH domain, a serine at residue 55 of the VH domain and a tyrosine at residue 66 of the VH domain.

The inventors have also shown that the anti-EGFR Fabs are able to specifically bind both ectopically-expressed and endogenous cell-surface EGFR. Further, treatment of EGFR-positive MDA-MB-231 breast cancer cells with Fab 8708 or Fab 8709 prior to treatment with EGF inhibited EGFR phosphorylation in a dose-dependent manner. The inventors have also shown that both Fab 8708 and Fab 8709 compete with EGF for binding to EGFR.

The term EGFR as used herein refers to the ErbB1 or EGFR receptor tyrosine kinases and includes, without limitation, EGFR from any source such as those with sequences as shown in Genbank Accessions: AAI28420, AAI18666, AAH94761, incorporated herein by reference in their entirety. In one embodiment, EGFR is human EGFR.

EGFR includes a number of different domains, including extracellular domains I-IV. These domains are known and can be readily identified by a person of skill in the art. Structural models of the EGF-mediated EGFR homodimer reveal extensive receptor-receptor contacted mediated by a "dimerization loop" in domain II. In one embodiment of the present disclosure, the domain II dimerization loop of EGFR comprises the sequence as shown in SEQ ID NO: 57.

EGFR-Binding Agents

Accordingly, the disclosure therefore provides novel isolated binding agents that bind to EGFR, referred to herein as "EGFR-binding agents". As used herein, an EGFR-binding agent which "binds EGFR", "specifically binds EGFR" or is referred to as "anti-EGFR" is an agent which binds EGFR-expressing cells as opposed to cells not expressing EGFR and/or which binds EGFR according to other criteria described herein. The aforementioned terminology employs EGFR merely for illustrative purposes and applies identically herein in reference to any other protein. The terms "immunoreacts with EGFR", or "is directed against EGFR" are also used herein for the same purpose.

In one embodiment, the EGFR-binding agent binds to an epitope wholly or partly within domain I and/or domain II of EGFR. In another embodiment, the EGFR-binding agent specifically binds to domain I and/or domain II of epidermal growth factor receptor (EGFR). In another embodiment, the binding agent does not bind domain III of EGFR.

As used herein, the term "epitope" refers to the specific site or specific combination of sites/amino acids on an antigen that are bound by the Fabs described herein, for example, unmodified or modified (e.g. post-translationally modified, e.g. glycosylated) amino acid residues of EGFR, the minimal polypeptide segment of EGFR encompassing these amino acid residues, or any combination of polypeptide segments of EGFR encompassing these amino acid residues. Epitopic determinants usually consist of molecules such as amino acids or sugar side chains and usually have specific three dimensional structural characteristics, as well as specific charge characteristics.

As used herein, unless otherwise specified, an antibody or a bivalent antibody fragment (e.g. F(ab')$_2$) referred to as comprising "a" specific light chain or "a" specific heavy chain in the singular refers to an antibody or a bivalent antibody fragment in which both light chains or both heavy chains are identical, respectively.

Embodiments of the EGFR-binding agent include any type of EGFR-binding molecule, macromolecule, substance, compound, material, composition, or complex, without limitation.

In one embodiment, the EGFR-binding agent is a polypeptide. In other embodiments, the EGFR-binding agent is a non-polypeptidic agent, such as an EGFR-binding nucleic acid or an EGFR-binding organic compound. The EGFR-binding agent may be monomeric or multimeric. The EGFR-binding agent may be polymeric or non-polymeric. Alternately, the EGFR-binding agent may be an engineered polypeptide (e.g. a naturally occurring polypeptide engineered to have a modified amino acid sequence; or a chimeric polypeptide engineered to comprise two or more naturally occurring amino acid sequences; or an engineered polypeptide selected from a library of engineered polypeptides having randomized amino acid sequences), or a chemically modified polypeptide.

In one embodiment, the EGFR-binding agent comprises an EGFR-binding antibody variable region that specifically binds EGFR (also referred to herein as an "EGFR-binding antibody variable region").

As used herein, an EGFR-binding antibody variable region is a combination of an antibody heavy chain variable domain and an antibody light chain variable domain, where the antibody heavy chain variable domain and the antibody light chain variable domain form an antigen-binding site that specifically binds EGFR.

The EGFR-binding agent is optionally an antibody, an antigen-binding fragment of an antibody, or an agent comprising an EGFR-binding antibody variable region.

As used herein, and unless otherwise specified, the term "antibody" refers to an immunoglobulin (Ig) molecule. As used herein, an immunoglobulin molecule is defined as set forth in Kabat et al., 1991.

The basic antibody structural unit is known to comprise a tetramer composed of two identical pairs of polypeptide chains, each pair having one light ("L") (about 25 kDa) and one heavy ("H") chain (about 50-70 kDa). The amino-terminal portion of the light chain forms a light chain variable domain (VL) and the amino-terminal portion of the heavy chain forms a heavy chain variable domain (VH). Together, the VH and VL domains form the antibody variable region (Fv) which is primarily responsible for antigen recognition/binding. The carboxy-terminal portions of the heavy and light chains together form a constant region primarily responsible for effector function. Three highly divergent stretches within each of the VH domain and VL domain, referred to as complementarity determining regions (CDRs), are interposed between more conserved flanking stretches known as "framework regions", or "FRs". Thus, the term "FR" refers to amino acid sequences which are naturally found between, and adjacent to, CDRs in immunoglobulins. A VH domain typically has four FRs, referred to herein as VH framework region 1 (FR1), VH framework region 2 (FR2), VH framework region 3 (FR3), and VH framework region 4 (FR4). Similarly, a VL domain typically has four FRs, referred to herein as VL framework region 1 (FR1), VL framework region 2 (FR2), VL framework region 3 (FR3), and VL framework region 4 (FR4). In an antibody molecule, the three CDRs of a VL domain (CDR-L1, CDR-L2 and CDR-L3) and the three CDRs of a VH domain (CDR-H1, CDR-H2 and CDR-H3) are disposed relative to each other in three dimensional space to form an antigen-binding site within the antibody variable region. The surface of the antigen-binding site is complementary to a three-dimensional surface of a bound antigen. Unless specified otherwise, the convention employed herein to describe antibodies, including to number amino acid residues of a VL domain and of a VH domain, and to define CDRs and FRs therein is the INTERNATIONAL IMMUNOGENETICS INFORMATION SYSTEM (IMGT numbering system; Lefranc et al., 2003). One of ordinary skill in the art would possess the knowledge for numbering amino acid residues of a VL domain and of a VH domain, and identifying CDRs and FRs therein, according to a routinely employed numbering system such as the IMGT numbering system, the Kabat numbering system (Kabat et al., 1991), and the like.

The EGFR-binding agent may be an antibody, such as a human antibody, containing engineered variable regions (e.g. containing variable regions selected from a phage display library displaying engineered antibody variable regions, e.g. a phage-Fab library or a phage-scFv library), or a chimeric antibody comprising human constant regions and an antibody variable region of a non-human mammal. The EGFR-binding agent may be a humanized antibody, e.g. an antibody comprising human constant regions, human variable region framework regions, and EGFR-binding CDRs generated in a non-human mammal. The non-human mammal may be a rodent, such as a mouse, rat, rabbit, guinea pig or hamster. Alternately, the non-human mammal may be an ungulate, such as a camelid or a bovid. The EGFR-binding agent may be an antibody comprising heavy chain constant regions belonging to any type of class, or subclass. The EGFR-binding agent may comprise any type of light chain.

In one embodiment, the EGFR-binding agent is a human antibody, such as an IgG1 antibody, wherein the heavy chain constant regions are gamma1 heavy chain constant regions. In other embodiments, the EGFR-binding agent is a human antibody, such as an IgA1, IgA2, IgD, IgG2, IgG3, IgG4, IgE or IgM antibody, wherein the heavy chain constant regions are alpha1, alpha2, delta, gamma2, gamma3, gamma4, epsilon or mu heavy chain constant regions, respectively.

In yet a further embodiment, the EGFR-binding agent is an antibody wherein the light chains comprise human kappa light chain constant domains, or wherein the light chains are human kappa light chains. Alternately, the EGFR-binding agent is an antibody wherein the light chains comprise human lambda light chain constant domains, or wherein the light chains are human lambda light chains.

In still a further embodiment the EGFR-binding agent is an antibody comprising human gamma1 heavy chain constant regions and human kappa light chains.

Embodiments of EGFR-binding agents of the present disclosure further include, but are not limited to, fragment antigen-binding (Fab), single-chain Fv (scFv), single-chain Fab (scFab), Fab', Fv, chemically linked F(ab')$_2$, dsFv, dsFv', sc(Fv)$_2$, ds-scFv, (dsFv)$_2$, scFv-Fc, scFv-based chimeric antigen receptors (CARs), Fab-based CARs, scFab-based CARs, single-chain immunoglobulin (e.g. scIgG), single-domain antibody (sdAb, nanobody), scFv-Fc, minibody (scFv-CH3), diabody, tribody, tetrabody, multimeric antibody (e.g. scFv dimer, bivalent diabody), multispecific antibody (e.g. bispecific antibody, trispecific antibody, di-scFv, tri-scFv, bispecific Fab$_2$, trispecific Fab$_2$, trispecific triabody, trispecific Fab$_3$), multimeric/multispecific antibody (e.g. scFv dimer, bispecific diabody, dsFv-dsFv'), heavy-chain antibody, Fab$_3$, divalent VHH, pentavalent VHH (pentabody), (scFv-SA)$_4$ and, [sc(Fv)$_2$]$_2$.

In another embodiment, the EGFR-binding agent is a phage displaying a polypeptide comprising an EGFR-binding antibody variable region, such as a phage-Fab or phage-scFv.

Embodiments of EGFR-binding agents of the present disclosure still further include EGFR-binding nucleic acid aptamers (e.g. RNA aptamers or DNA aptamers; see, e.g. Lipi et al., 2016), peptide aptamers (see, e.g. Parashar, 2016), and chemically synthesized agents (e.g. synthetic antibody mimics; see, e.g. McEnaney et al., 2014).

In another embodiment, the EGFR-binding agent is a peptide analog. Peptide analogs are commonly used in the pharmaceutical industry as non-peptide drugs with properties analogous to those of the template peptide. These types of non-peptide compounds are termed "peptide mimetics" or "peptidomimetics" (see, e.g. Fauchere, 1986; Veber and Freidinger, 1985; and Evans et al., 1987). Such compounds are often developed with the aid of computerized molecular modeling. Peptide mimetics that are structurally similar to biologically useful peptides may be used to produce an equivalent biological effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH2NH—, —CH2S—, —CH2-CH2-, —CH=CH— (cis and trans), —COCH2-, CH(OH)CH2- and —CH2SO—, by methods well known in the art. Systematic substitution of one or more amino acids of a consensus sequence with a D-amino acid of the same type (e.g. D-lysine in place of L-lysine) may be used to generate more stable peptides. In addition, constrained peptides comprising a consensus sequence or a substantially identical consensus sequence variation may be generated by methods known in the art (see, e.g. Rizo and Gierasch, 1992), for example, by adding internal cysteine residues capable of forming intramolecular disulfide bridges which cyclize the peptide.

In an embodiment, the EGFR-binding agent comprises an antibody variable region which comprises (a) an antibody light chain variable domain, wherein the amino acid sequences of the light chain CDR1, light chain CDR2 and light chain CDR3 thereof correspond to SEQ ID NO: 1, SEQ ID NO: 2, and SEQ ID NO: 3, respectively and (b) an antibody heavy chain variable domain wherein the amino acid sequences of the heavy chain CDR1, heavy chain CDR2 and heavy chain CDR3 thereof correspond to amino acids 1-8 of SEQ ID NO: 6, amino acids 2-9 of SEQ ID NO: 9, and SEQ ID NO: 11. In another embodiment, the antibody variable region further comprises an isoleucine at residue 39 of the VH domain, a tyrosine at residue 55 of the VH domain and a tyrosine at residue 66 of the VH domain. See for example, clone DL06.

In another embodiment, the EGFR-binding agent comprises an antibody variable region which comprises (a) an antibody light chain variable domain, wherein the amino acid sequences of the light chain CDR1, light chain CDR2 and light chain CDR3 thereof correspond to SEQ ID NO: 1, SEQ ID NO: 2, and SEQ ID NO: 4, respectively and (b) an antibody heavy chain variable domain wherein the amino acid sequences of the heavy chain CDR1, heavy chain CDR2 and heavy chain CDR3 thereof correspond to amino acids 1-8 of SEQ ID NO: 6, amino acids 2-9 of SEQ ID NO: 9, and SEQ ID NO: 12. In another embodiment, the antibody variable region further comprises an isoleucine at residue 39 of the VH domain, a tyrosine at residue 55 of the VH domain and a tyrosine at residue 66 of the VH domain. See for example, DL06 AM Clone 10.

In another embodiment, the EGFR-binding agent comprises an antibody variable region which comprises (a) an antibody light chain variable domain, wherein the amino acid sequences of the light chain CDR1, light chain CDR2 and light chain CDR3 thereof correspond to SEQ ID NO: 1, SEQ ID NO: 2, and SEQ ID NO: 3, respectively and (b) an antibody heavy chain variable domain wherein the amino acid sequences of the heavy chain CDR1, heavy chain CDR2 and heavy chain CDR3 thereof correspond to amino acids 1-8 of SEQ ID NO: 6, amino acids 2-9 of SEQ ID NO: 9, and SEQ ID NO: 13. In another embodiment, the antibody variable region further comprises an isoleucine at residue 39 of the VH domain, a tyrosine at residue 55 of the VH domain and a tyrosine at residue 66 of the VH domain. See for example, DL06 AM Clone 23.

In another embodiment, the EGFR-binding agent comprises an antibody variable region which comprises (a) an antibody light chain variable domain, wherein the amino acid sequences of the light chain CDR1, light chain CDR2 and light chain CDR3 thereof correspond to SEQ ID NO: 1, SEQ ID NO: 2, and SEQ ID NO: 3, respectively and (b) an antibody heavy chain variable domain wherein the amino acid sequences of the heavy chain CDR1, heavy chain CDR2 and heavy chain CDR3 thereof correspond to amino acids 1-8 of SEQ ID NO: 6, amino acids 2-9 of SEQ ID NO: 9, and SEQ ID NO: 14. In another embodiment, the antibody variable region further comprises an isoleucine at residue 39 of the VH domain, a tyrosine at residue 55 of the VH domain and a tyrosine at residue 66 of the VH domain. See for example, DL06 AM Clone 24.

In another embodiment, the EGFR-binding agent comprises an antibody variable region which comprises (a) an antibody light chain variable domain, wherein the amino acid sequences of the light chain CDR1, light chain CDR2 and light chain CDR3 thereof correspond to SEQ ID NO: 1, SEQ ID NO: 2, and SEQ ID NO: 3, respectively and (b) an antibody heavy chain variable domain wherein the amino acid sequences of the heavy chain CDR1, heavy chain CDR2 and heavy chain CDR3 thereof correspond to amino acids 1-8 of SEQ ID NO: 7, amino acids 2-9 of SEQ ID NO: 9, and SEQ ID NO: 15. In another embodiment, the antibody variable region further comprises an isoleucine at residue 39 of the VH domain, a tyrosine at residue 55 of the VH domain and a tyrosine at residue 66 of the VH domain. See for example, clone DL06 SR02 (Fab 8708).

In another embodiment, the EGFR-binding agent comprises an antibody variable region which comprises (a) an antibody light chain variable domain, wherein the amino acid sequences of the light chain CDR1, light chain CDR2 and light chain CDR3 thereof correspond to SEQ ID NO: 1, SEQ ID NO: 2, and SEQ ID NO: 5, respectively and (b) an antibody heavy chain variable domain wherein the amino acid sequences of the heavy chain CDR1, heavy chain CDR2 and heavy chain CDR3 thereof correspond to amino acids 1-8 of SEQ ID NO: 8, amino acids 2-9 of SEQ ID NO: 10, and SEQ ID NO: 16. In another embodiment, the antibody variable region further comprises a methionine at residue 39 of the VH domain, a serine at residue 55 of the VH domain and a tyrosine at residue 66 of the VH domain. See for example, Fab H (Fab 8709).

Accordingly, the disclosure provides an EGFR-binding agent comprising: an antibody light chain variable domain comprising a light chain complementarity-determining region (CDR)$_1$ comprising or consisting of the amino acid sequence of SEQ ID NO: 1, a light chain CDR2 comprising or consisting of the amino acid sequence of SEQ ID NO: 2, and a light chain CDR3 comprising or consisting of the amino acid sequence of SEQ ID NO: 3; and (ii) an antibody heavy chain variable domain comprising a heavy chain CDR1 comprising or consisting of amino acids 1-8 of SEQ ID NO: 6, a heavy chain CDR2 comprising or consisting of amino acids 2-9 of SEQ ID NO: 9, and a heavy chain CDR3 comprising or consisting of the amino acid sequence of SEQ ID NO: 11. In another embodiment, the heavy chain variable domain further comprises an isoleucine at residue 39 of the VH domain, a tyrosine at residue 55 of the VH domain and a tyrosine at residue 66 of the VH domain. See for example DL06.

The disclosure also provides affinity matured derivatives of DL06. As used herein, the term "affinity matured derivatives" refer to variants of clones obtained through methods of affinity maturation which have similar, but not identical, CDR sequences as the original clone. Affinity matured derivatives bind to similar epitopes (for example, overlapping epitopes or the same epitope) and have similar functional activity and/or specificity as the original clone. In some embodiments, an affinity matured derivative has increased affinity to the antigen as compared to the original clone. For example, affinity may be increased by at least 5, 10, 25, 50, 75 or 100%. As described in Examples 1 and 2, affinity matured derivatives of DL06 include DL06 AM Clone 10, DL06 AM Clone 23, DL06 AM Clone 24 and DL06 SR02 (Fab 8708).

Accordingly, the disclosure also provides an EGFR-binding agent comprising:

(a) (i) an antibody light chain variable domain comprising a light chain complementarity-determining region (CDR)1 comprising or consisting of the amino acid sequence of SEQ ID NO: 1, a light chain CDR2 comprising or consisting of the amino acid sequence of SEQ ID NO: 2, and a light chain CDR3 comprising or consisting of the amino acid sequence of SEQ ID NO: 4; and (ii) an antibody heavy chain variable domain comprising a heavy chain CDR1 comprising or consisting of amino acids 1-8 of SEQ ID NO: 6, a heavy chain CDR2 comprising or consisting of amino acids 2-9 of SEQ ID NO: 9, and a heavy chain CDR3 comprising or consisting of the amino acid sequence of SEQ ID NO: 12. In another embodiment, the heavy chain variable domain further comprises an isoleucine at residue 39 of the VH domain, a tyrosine at residue 55 of the VH domain and a tyrosine at residue 66 of the VH domain (see for example DL06 AM Clone 10);

(b) (i) an antibody light chain variable domain comprising a light chain complementarity-determining region (CDR)1 comprising or consisting of the amino acid sequence of SEQ ID NO: 1, a light chain CDR2 comprising or consisting of the amino acid sequence of SEQ ID NO: 2, and a light chain CDR3 comprising or consisting of the amino acid sequence of SEQ ID NO: 3; and (ii) an antibody heavy chain variable domain comprising a heavy chain CDR1 comprising or consisting of amino acids 1-8 of SEQ ID NO: 6, a heavy chain CDR2 comprising or consisting of amino acids 2-9 of SEQ ID NO: 9, and a heavy chain CDR3 comprising or consisting of the amino acid sequence of SEQ ID NO: 13. In another embodiment, the heavy chain variable domain further comprises an isoleucine at residue 39 of the VH domain, a tyrosine at residue 55 of the VH domain and a tyrosine at residue 66 of the VH domain (see for example DL06 AM Clone 23);

(c) (i) an antibody light chain variable domain comprising a light chain complementarity-determining region (CDR)1 comprising or consisting of the amino acid sequence of SEQ ID NO: 1, a light chain CDR2 comprising or consisting of the amino acid sequence of SEQ ID NO: 2, and a light chain CDR3 comprising or consisting of the amino acid sequence of SEQ ID NO: 3; and (ii) an antibody heavy chain variable domain comprising a heavy chain CDR1 comprising or consisting of amino acids 1-8 of SEQ ID NO: 6, a heavy chain CDR2 comprising or consisting of amino acids 2-9 of SEQ ID NO: 9, and a heavy chain CDR3 comprising or consisting of the amino acid sequence of SEQ ID NO: 14. In another embodiment, the heavy chain variable domain further comprises an isoleucine at residue 39 of the VH domain, a tyrosine at residue 55 of the VH domain and a tyrosine at residue 66 of the VH domain (see for example DL06 AM Clone 24); or (d) (i) an antibody light chain variable domain comprising a light chain complementarity-determining region (CDR)1 comprising or consisting of the amino acid sequence of SEQ ID NO: 1, a light chain CDR2 comprising or consisting of the amino acid sequence of SEQ ID NO: 2, and a light chain CDR3 comprising or consisting of the amino acid sequence of SEQ ID NO: 3; and (ii) an antibody heavy chain variable domain comprising a heavy chain CDR1 comprising or consisting of amino acids 1-8 of SEQ ID NO: 7, a heavy chain CDR2 comprising or consisting of amino acids 2-9 of SEQ ID NO: 9, and a heavy chain CDR3 comprising or consisting of the amino acid sequence of SEQ ID NO: 15. In another embodiment, the heavy chain variable domain further comprises an isoleucine at residue 39 of the VH domain, a tyrosine at residue 55 of the VH domain and a tyrosine at residue 66 of the VH domain (see for example DL06 SR02 (Fab 8708)).

The disclosure further provides an EGFR-binding agent comprising: (i) an antibody light chain variable domain comprising a light chain complementarity-determining region (CDR)1 comprising or consisting of the amino acid sequence of SEQ ID NO: 1, a light chain CDR2 comprising or consisting of the amino acid sequence of SEQ ID NO: 2, and a light chain CDR3 comprising or consisting of the amino acid sequence of SEQ ID NO: 5; and (ii) an antibody heavy chain variable domain comprising a heavy chain CDR1 comprising or consisting of amino acids 1-8 of SEQ ID NO: 8, a heavy chain CDR2 comprising or consisting of amino acids 2-9 of SEQ ID NO: 10, and a heavy chain CDR3 comprising or consisting of the amino acid sequence of SEQ ID NO: 16. In another embodiment, the heavy chain variable domain further comprises a methionine at residue 39 of the VH domain, a serine at residue 55 of the VH domain and a tyrosine at residue 66 of the VH domain (see for example Fab H (Fab 8709)).

Also particularly disclosed herein is a EGFR-binding agent comprising: (a) a heavy chain amino acid sequence encoded by the nucleic acid sequence shown in SEQ ID NO: 33 and functional variants thereof, and a light chain amino acid sequence encoded by the nucleic acid sequence shown in SEQ ID NO: 35 and functional variants thereof (see for example DL06), (b) a heavy chain amino acid sequence encoded by the nucleic acid sequence shown in SEQ ID NO: 37 and functional variants thereof, and a light chain amino acid sequence encoded by the nucleic acid sequence shown in SEQ ID NO: 39 and functional variants thereof (see for example DL06 AM Clone 10), (c) a heavy chain amino acid sequence encoded by the nucleic acid sequence shown in SEQ ID NO: 41 and functional variants thereof, and a light chain amino acid sequence encoded by the nucleic acid sequence shown in SEQ ID NO: 43 and functional variants thereof (see for example DL06 AM Clone 23), (d) a heavy chain amino acid sequence encoded by the nucleic acid sequence shown in SEQ ID NO: 45 and functional variants thereof, and a light chain amino acid sequence encoded by the nucleic acid sequence shown in SEQ ID NO: 47 and functional variants thereof (see for example DL06 AM Clone 24), (e) a heavy chain amino acid sequence encoded by the nucleic acid sequence shown in SEQ ID NO: 49 and functional variants thereof, and a light chain amino acid sequence encoded by the nucleic acid sequence shown in SEQ ID NO: 51 and functional variants thereof (see for example DL06 SR02 (Fab 8708), or (f) a heavy chain amino acid sequence encoded by the nucleic acid sequence shown in SEQ ID NO: 53 and functional variants thereof, and a light chain amino acid sequence encoded by the nucleic acid sequence shown in SEQ ID NO: 55 and functional variants thereof (see for example Fab H (Fab 8709)).

Further disclosed herein is a EGFR-binding agent comprising:

(a) a heavy chain amino acid sequence shown in SEQ ID NO: 34 and functional variants thereof, and a light chain amino acid sequence shown in SEQ ID NO: 36 and functional variants thereof (see for example DL06), (b) a heavy chain amino acid sequence shown in SEQ ID NO: 38 and functional variants thereof, and a light chain amino acid sequence shown in SEQ ID NO: 40 and functional variants thereof (see for example DL06 AM Clone 10), (c) a heavy chain amino acid sequence shown in SEQ ID NO: 42 and functional variants thereof, and a light chain amino acid sequence shown in SEQ ID NO: 44 and functional variants thereof (see for example DL06 AM Clone 23), (d) a heavy chain amino acid sequence shown in SEQ ID NO: 46 and functional variants thereof, and a light chain amino acid sequence shown in SEQ ID NO: 48 and functional variants thereof (see for example DL06 AM Clone 24), (e) a heavy chain amino acid sequence shown in SEQ ID NO: 50 and functional variants thereof, and a light chain amino acid sequence shown in SEQ ID NO: 52 and functional variants thereof (see for example DL06 SR02 (Fab 8708), or (f) a heavy chain amino acid sequence shown in SEQ ID NO: 54 and functional variants thereof, and a light chain amino acid sequence shown in SEQ ID NO: 56 and functional variants thereof (see for example Fab H (Fab 8709)).

Any of the EGFR-binding agents of the present disclosure may be obtained and suitably prepared for use using well-known techniques.

Polypeptidic EGFR-binding agents of the disclosure can be synthesized by recombinant techniques. A polypeptidic EGFR-binding agent of the disclosure may be produced in recombinant sources, such as recombinant cell lines or transgenic animals. Techniques can be adapted for the production of single-chain antibodies, such as a scFv, specific to EGFR (see, e.g. U.S. Pat. No. 4,946,778).

Alternatively, a polypeptidic EGFR-binding agent of the disclosure, such as an EGFR-binding antibody of the disclosure may be obtained by immunizing an animal with EGFR, or with a polypeptide comprising a suitable EGFR epitope, so as to generate the antibody in the animal's serum.

An EGFR-binding IgG antibody of the disclosure can be purified from a biological sample, such as serum, via techniques such as affinity chromatography using protein A or protein G (see, e.g. Wilkinson, 2000). Additionally or alternatively, EGFR, or a polypeptide comprising an epitope thereof, which is specifically bound by the EGFR-binding agent may be immobilized on a column to purify the EGFR-binding agent from a sample by immunoaffinity chromatography.

An EGFR-binding antibody fragment of the disclosure may be obtained from an antibody using conventional techniques. For example, F(ab')2 fragments can be generated by treating an antibody with pepsin. The resulting F(ab')2 fragment can be treated to reduce disulfide bridges to produce Fab' fragments.

Methods of producing polypeptidic EGFR-binding agents of the disclosure are described in further detail below.

As set forth above, in an embodiment, the EGFR-binding agent may be a bispecific antibody.

As used herein, bispecific antibodies are binding agents comprising two different antibody variable regions which confer binding specificities for at least two different antigens or two different epitopes of the same antigen.

The presently disclosed bispecific antibodies specifically bind EGFR and another antigen or specifically bind different epitopes of EGFR. Optionally, the bispecific antibody binds EGFR and a cell-surface protein, receptor or receptor subunit.

In one embodiment, the bispecific antibody comprises an EGFR-binding single-chain Fab and a non-EGFR-binding scFv. Alternately, the bispecific antibody comprises an EGFR-binding Fab and a non-EGFR-binding scFv.

In another embodiment, the EGFR-binding agent is a bispecific antibody that targets, binds and/or engages immune cells such as T cells, macrophages or NK cells. According to this embodiment, the EGFR-binding agent is a bispecific antibody where one of the binding specificities is for EGFR and the other binding specificity is for an antigen expressed on the surface of T cells, macrophages or NK cells. For example, the bispecific antibody may bind EGFR and an immune cell receptor, such a receptor of a T cell, which when bound activates or inhibits activity of the immune cell.

Various techniques for making and isolating bispecific antibodies directly from recombinant cell culture have been described. For example, bispecific antibodies have been produced using leucine zippers (see, e.g. Kostelny et al., 1992), using "diabody" technology (see, e.g. Hollinger et al., 1993), and using single-chain Fv (scFv) dimers (see, e.g. Gruber et al., 1994).

A bispecific antibody that engages T cells may be referred to as a bispecific T-cell engager (BiTE). In one embodiment of the present disclosure, the bispecific antibody/BiTE specifically binds both EGFR and the T cell co-receptor CD3 (also referred to herein as EGFR-binding/CD3-binding bispecific antibody). Accordingly, provided herein is a bispecific antibody/BiTE which comprises an EGFR-binding antibody variable region of the disclosure and a CD3-binding antibody variable region. Such bispecific antibodies/BiTEs allow targeting of a T cell to a cell, such as a cancer cell, expressing surface EGFR. Various configurations of the bispecific antibodies/BiTEs are contemplated herein. For example, in one embodiment, the bispecific antibody/BiTE comprises an anti-EGFR Fab and an anti-CD3 scFv. Optionally, either the light chain or the heavy chain of the anti-EGFR Fab is linked to the heavy-chain of the anti-CD3 scFv. In another embodiment, the bispecific antibody/BiTE comprises an anti-EGFR single chain Fab (scFab) and an anti-CD3 ScFv. Optionally, either the light chain or the heavy chain of the anti-EGFR Fab or anti-EGFR scFab is linked to the heavy-chain of the anti-CD3 scFv. In one embodiment, the anti-CD3 scFv binds CD3 epsilon/gamma. In one embodiment, the BiTE/bispecific antibody binds CD3 epsilon/delta.

In a further embodiment, the bispecific antibody binds EGFR and the NK cell surface receptor CD16.

As described above, the EGFR-binding agent may have any number of valencies and/or specificities. For example, a trispecific and/or trivalent EGFR-binding agent can be prepared (see, e.g. Tutt et al., 1991).

As further described above, embodiments of the EGFR-binding agents also include EGFR-binding chimeric antigen receptors (CARs).

Accordingly, provided herein is a chimeric antigen receptor comprising (i) an EGFR-binding agent of the disclosure and (ii) one or more immune cell receptor signaling domains. In one embodiment, the CAR is a monomeric polypeptide which comprises an EGFR-binding scFv and a CAR intracellular signaling domain comprising a CD3-zeta intracellular signaling domain, and optionally further comprising one or more T cell costimulatory receptor intracellular signaling domains. In an additional embodiment, the EGFR-binding agent is a phage-Fab or phage-scFv, where the Fab or scFv specifically binds EGFR.

It can be desirable to modify a binding agent disclosed herein with respect to effector function, so as to enhance its effectiveness in binding/targeting EGFR-expressing cells and/or reducing levels of EGFR in EGFR-expressing cells. For example, where the binding agent comprises an antibody Fc region, such as an antibody, cysteine residue(s) can be introduced into the COOH terminal of the Fc region, thereby allowing interchain disulfide bond formation between antibody monomers in this region. The homodimeric antibody thus generated can have improved internalization capability and/or increased complement-mediated cell killing and antibody-dependent cellular cytotoxicity (ADCC) (see, e.g. Caron et al., 1992; and Shopes, 1992). Alternatively, an antibody can be engineered that has dual Fc regions and can thereby have enhanced complement lysis and ADCC capabilities (see, e.g. Stevenson et al., 1989). Functional variants of the EGFR-binding agents described herein are also encompassed by the present disclosure. The term "functional variant" as used herein includes modifications or chemical equivalents of the amino acid and nucleic acid sequences disclosed herein that perform substantially the same function as the polypeptides or nucleic acid molecules disclosed herein in substantially the same way. For example, functional variants of polypeptides disclosed herein include, without limitation, conservative amino acid substitutions.

A "conservative amino acid substitution" as used herein, is one in which one amino acid residue is replaced with another amino acid residue are substitutions that change an amino acid to a different amino acid with similar biochemical properties (e.g. charge, hydrophobicity and size). Variants of polypeptides also include additions and deletions to the polypeptide sequences disclosed herein. In addition, variant nucleotide sequences include analogs and derivatives thereof. A variant of the binding agents disclosed herein include agents that bind to the same antigen or epitope as the binding agents.

In one embodiment, the present disclosure includes functional variants to the amino acid sequences that encode the heavy and light chains of the EGFR-binding agents disclosed herein. In particular, functional variants of the amino acid sequences of the heavy and light chains of DL06 (SEQ ID NO: 34 and SEQ ID NO: 36, respectively), functional variants of the nucleotide sequences encoding the heavy chain and light chain of DL06 AM Clone 10 (SEQ ID NO: 38 and SEQ ID NO: 40, respectively), functional variants of the nucleotide sequences encoding the heavy chain and light chain of DL06 AM Clone 23 (SEQ ID NO: 42 and SEQ ID NO: 44, respectively), functional variants of the nucleotide sequences encoding the heavy chain and light chain of DL06 AM Clone 24 (SEQ ID NO: 46 and SEQ ID NO: 48, respectively), functional variants of the nucleotide sequences encoding the heavy chain and light chain of DL06 SR02 (Fab 8708) (SEQ ID NO: 50 and SEQ ID NO: 52, respectively) and functional variants of the nucleotide sequences encoding the heavy chain and light chain of Fab H (Fab 8709) (SEQ ID NO: 54 and SEQ ID NO: 56, respectively), are provided.

In another embodiment, the present disclosure includes functional variants to the nucleic acid sequences that encode the EGFR-binding agents disclosed herein. In particular, functional variants of the nucleotide sequences encoding the heavy chain and light chain of DL06 (SEQ ID NO: 33 and SEQ ID NO: 35, respectively), functional variants of the nucleotide sequences encoding the heavy chain and light chain of DL06 AM Clone 10 (SEQ ID NO: 37 and SEQ ID NO: 39, respectively), functional variants of the nucleotide sequences encoding the heavy chain and light chain of DL06 AM Clone 23 (SEQ ID NO: 41 and SEQ ID NO: 43, respectively), functional variants of the nucleotide sequences encoding the heavy chain and light chain of DL06 AM Clone 24 (SEQ ID NO: 45 and SEQ ID NO: 47, respectively), functional variants of the nucleotide sequences encoding the heavy chain and light chain of DL06 SR02 (Fab 8708) (SEQ ID NO: 49 and SEQ ID NO: 51, respectively) and functional variants of the nucleotide sequences encoding the heavy chain and light chain of Fab H (Fab 8709) (SEQ ID NO: 53 and SEQ ID NO: 55, respectively), are provided. In addition, the functional variants include nucleotide sequences that hybridize to the nucleic acid sequences encoding the EGFR-binding proteins and nucleotide sequences that hybridize to SEQ ID NOs: 33, 35, 37, 39, 41, 43, 45, 47, 49, 51, 53, and 55, or the complement thereof, under at least moderately stringent hybridization conditions. In addition, the functional variants include nucleotide sequences that hybridize to the nucleic acid sequences encoding the EGFR-binding proteins and nucleotide sequences disclosed herein, under at least moderately stringent hybridization conditions.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41 (% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "sequence identity" as used herein refers to the percentage of sequence identity between two amino acid sequences or two nucleic acid sequences. To determine the percent identity of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul, 1990, modified as in Karlin and Altschul, 1993. Such an algorithm is incorporated into the NBLAST and XBLAST programs of Altschul et al., 1990. BLAST nucleotide searches can be performed with the NBLAST nucleotide program parameters set, e.g. for score=100, wordlength=12 to obtain nucleotide sequences homologous to a nucleic acid molecules of the present disclosure. BLAST protein searches can be performed with the XBLAST program parameters set, e.g. to score-50, wordlength=3 to obtain amino acid sequences homologous to a protein molecule of the present invention. To obtain gapped alignments for comparison purposes, Gapped BLAST can be utilized as described in Altschul et al., 1997. Alternatively, PSI-BLAST can be used to perform an iterated search which detects distant relationships between molecules. When utilizing BLAST, Gapped BLAST, and PSI-Blast programs, the default parameters of the respective programs (e.g. of XBLAST and NBLAST) can be used (see, e.g. the NCBI website). Another non-limiting example of a mathematical algorithm utilized for the comparison of sequences is the algorithm of Myers and Miller, 1988. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In another embodiment, the variant nucleotide sequences encoding the EGFR-binding agents comprise sequences having at least 50%, or at least 60%, or at least 70%, or at least 80%, or at least 90%, or at least 95% sequence identity to SEQ ID NOs: 33, 35, 37, 39, 41, 43, 45, 47, 49, 51, 53, and 55.

In another embodiment, the variant nucleotide sequences encoding the EGFR-binding agents comprise sequences having at least 50%, or at least 60%, or at least 70%, or at least 80%, or at least 90%, or at least 95% sequence identity to the framework regions of SEQ ID NOs: 33, 35, 37, 39, 41, 43, 45, 47, 49, 51, 53, and 55. As used herein, reference to "framework regions" of a nucleotide sequence refers to the nucleotide sequence encoding the framework region (i.e. non-CDR regions) of the corresponding heavy or light chain.

Nucleic Acids and Vectors

Also provided are nucleic acids encoding the antibody variable regions described herein and nucleic acids encoding polypeptides comprising these antibody variable regions. As used herein, the term "nucleic acids" includes isolated nucleic acids.

In particular, nucleic acids encoding the CDR regions of DL06 as set out in SEQ ID NOs: 1, 2, 3, 6, 9 and 11, and functional variants thereof are provided. Also provided are nucleic acids encoding the CDR regions of DL06 AM Clone 10 as set out in SEQ ID NOs: 1, 2, 4, 6, 9 and 12, and functional variants thereof. Also provided are nucleic acids encoding the CDR regions of DL06 AM Clone 23 as set out in SEQ ID NOs: 1, 2, 3, 6, 9 and 13, and functional variants thereof. Also provided are nucleic acids encoding the CDR regions of DL06 AM Clone 24 as set out in SEQ ID NOs: 1, 2, 3, 6, 9 and 14, and functional variants thereof. Also provided are nucleic acids encoding the CDR regions of Fab H (Fab 8709) as set out in SEQ ID NOs: 1, 2, 5, 8, 10 and 16, and functional variants thereof. Also provided are nucleic acids encoding the CDR regions of DL06 SR02 (Fab 8708) as set out in SEQ ID NOs: 1, 2, 3, 7, 9 and 15, and functional variants thereof.

The disclosure also provides nucleic acids encoding the light chain and heavy chain of DL06, DL06 AM Clone 10, DL06 AM Clone 23, DL06 AM Clone 24, DL06 SR02 (Fab 8708) and Fab H (Fab 8709) as set out in SEQ ID Nos: 33, 35, 37, 39, 41, 43, 45, 47, 49, 51, 53, and 55, and functional variants thereof.

Polypeptidic binding agents disclosed herein can be expressed by a vector containing a nucleic acid encoding the polypeptide of interest using methods which are well known and routinely practiced in the art. Accordingly, the present disclosure also provides a vector expressing any of the nucleic acids described herein.

The polypeptidic binding agents can be prepared by constructing a nucleic acid encoding a polypeptidic binding agent, inserting the construct into an expression vector, and then expressing it in appropriate host cells. Vectors useful for expressing the polypeptidic binding agents disclosed herein are well known in the art. In one embodiment, the vector includes suitable translation initiation and termination signals in operable reading phase with a functional promoter and can comprise one or more phenotypic selectable markers and an origin of replication to ensure maintenance of the vector and, if desirable, to provide amplification within the host. In addition to vectors, the nucleic acids of the present disclosure can be delivered to a cell or a subject via any other method known in the art including, but not limited to, liposomes, naked DNA, adjuvant-assisted DNA, gene gun, catheters, etc.

Monoclonal Polypeptides/Monoclonal Antibodies

As described above, the EGFR-binding agent can be a polypeptide comprising an EGFR-binding antibody variable region. Accordingly, the disclosure further provides a monoclonal polypeptidic EGFR-binding agent of the disclosure, such as a monoclonal EGFR-binding antibody of the disclosure.

As used herein, a "monoclonal" polypeptidic EGFR-binding agent of the disclosure refers to a population of identical polypeptidic EGFR-binding agent molecules. For example, in the case of a monoclonal polypeptidic EGFR-binding agent of the disclosure comprising an EGFR-binding antibody variable region, such as a monoclonal EGFR-binding antibody of the disclosure, the CDRs are identical in all the molecules of the population. Various procedures known within the art may be used for the production of monoclonal polypeptides, such as monoclonal antibodies of the disclosure (see, for example, Greenfield, 2013). Monoclonal antibodies are commonly alternatively referred to using the abbreviations "mAb" or "MAb".

Monoclonal antibodies can be made by recombinant DNA methods, such as those described in U.S. Pat. No. 4,816,567. DNA encoding the monoclonal antibodies and antigen-binding fragments thereof can be readily isolated and sequenced using conventional procedures (e.g. by using oligonucleotide probes that are capable of binding specifically to genes encoding the heavy and light chains of murine antibodies). The hybridoma cells serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

Monoclonal antibodies may also be generated, e.g. by immunizing an animal with EGFR, such as, for example, murine, rat or human EGFR or an immunogenic fragment, derivative or variant thereof. Alternatively, the animal is immunized with cells transfected with a vector containing a nucleic acid molecule encoding EGFR that is expressed and associated with the surface of the transfected cells. Alternatively, the antibodies are obtained by screening a library that contains antibody or antigen binding domain sequences for binding to EGFR. This library is prepared, e.g. in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to EGFR.

Monoclonal antibodies may be prepared, for example, using hybridoma methods (see, for example, Kohler and Milstein, 1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Affinity

Non-covalent interactions occur between an immunoglobulin molecule and an antigen for which the immunoglobulin is specific. The strength, or affinity of immunological binding interactions can be expressed in terms of the dissociation constant ($K_D$) of the interaction, wherein a smaller $K_D$ represents a greater affinity. The terms "dissociation constant" and "affinity" are used interchangeably herein to refer to $K_D$. Immunological binding properties of specific polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation (see, e.g. Malmqvist, 1993). The ratio of $K_{off}/K_{on}$ enables the cancellation of all parameters not related to affinity, and is equal to the dissociation constant $K_D$ (see, e.g. Davies et al., 1990).

In various embodiments, the EGFR-binding agent binds EGFR with an affinity ($K_D$) of ≤1 micromolar, ≤900 nM, ≤800 nM, ≤700 nM, ≤600 nM, ≤500 nM, ≤400 nM, ≤300 nM, ≤200 nM, ≤100 nM, ≤90 nM, ≤80 nM, ≤70 nM, 60 nM, ≤50 nM, ≤40 nM, ≤30 nM, ≤20 nM, 10 nM, ≤9 nM, ≤8 nM, ≤7 nM, ≤6 nM, ≤5 nM, ≤4 nM, ≤2 nM, ≤1 nM, ≤0.9 nM, ≤0.8 nM, ≤0.7 nM, ≤0.6 nM, ≤0.5 nM, ≤0.4 nM to 0.3 nM, ≤0.2 nM, or ≤100 pM to about 1 pM.

In further various embodiments, the EGFR-binding agent binds EGFR with an affinity ($K_D$) of 1 micromolar to 100 nM, 100 nM to 10 nM, 10 nM to 1 nM, 1 nM to 0.1 nM, or 0.1 nM to 10 pM. In another embodiment, the EGFR-bind agent binds EGFR with an affinity ($K_D$) of 40 to 60 nM or 45 to 55 nM, optionally about 50 nM.

The disclosure also provides an EGFR-binding agent which specifically binds an EGFR epitope bound by DL06, DL06 AM Clone 10, DL06 AM Clone 23, DL06 AM Clone 24, DL06 SR02 (Fab 8708) and/or Fab H (Fab 8709).

Any one of various methods known in the art can be used to identify an EGFR-binding agent which specifically binds an EGFR epitope bound by any of the Fabs described herein. A person skilled in the art will appreciate that binding assays such as a competition binding assay can be used for this purpose. Those skilled in the art will recognize that it is possible to determine, without undue experimentation, for example, if a binding agent specifically binds an EGFR epitope bound by one or more of the Fabs described herein by ascertaining whether the binding agent prevents the Fab(s) from binding to EGFR. If the binding agent being tested competes with one or more of the Fabs described herein, as shown by a decrease in binding to EGFR by the Fab(s), then the binding agent binds to the same epitope as one or more of the Fabs described herein. Methods for the testing the specificity of binding agents include, but are not limited to, enzyme linked immunosorbent assay (ELISA) and other immunologically mediated techniques known within the art.

Detection Agents

The EGFR-binding agents described herein are optionally labeled with a detection agent. As used herein, the term "detection agent" refers to any agent that allows the presence of the EGFR-binding agent to be detected and/or quantified. Examples of detection agents include, but are not limited to, peptide tags, enzymes (for example, HRP or alkaline phosphatase), proteins (for example phycoerythrin or biotin/streptavidin), magnetic particles, chromophores, fluorescent molecules, chemiluminescent molecules, radioactive labels and dyes. In one specific embodiment, the detection agent is IR800CW fluorophore. The EGFR-binding agent may be labeled directly or indirectly with the detection agent.

In another embodiment, the detection agent is lanthanide. For example, the EGFR-binding agent may be modified with a chelating agent such that it binds lanthanide for use in time resolved fluorescent applications. Without being bound by theory, lanthanide is believed to enhance sensitivity and widen the dynamic range of analysis. For example, non-radioactive lanthanide chelate labels offer long lived fluorescence emission and a large Stokes shift that can enhance signal to noise ratios. Dissociation enhanced lanthanide fluorescent immunoassays (DELFIA) are an alternative to ELISA that can be used to characterize protein-protein interactions, ligand receptor binding studies and more.

Conjugates

The present disclosure also includes a conjugate comprising (1) an EGFR-binding agent, optionally an antibody or an antibody antigen binding fragment, that has been attached to (2) an effector agent.

In one embodiment, the conjugate is an immunoconjugate wherein the EGFR-binding agent comprises an antibody variable region.

In one embodiment, the effector agent is a label, which can generate a detectable signal, directly or indirect. Examples of labels include radioactive isotopes (i.e., a radioconjugate).

In another embodiment, the effector agent is a therapeutic agent. Therapeutic agents include, but are not limited to, cancer therapeutic agents/antineoplastic agents. In yet another embodiment, the therapeutic agent is a toxin.

The term "cancer therapeutic agent" or "antineoplastic agent" is used herein to refer to agents that have the functional property of decreasing levels of cancer cells.

The toxin may be an enzymatically active toxin of bacterial, fungal, plant, or animal origin, or a fragment thereof. Toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

Radioconjugated EGFR-binding agents of the disclosure, such as antibodies of the disclosure, may be employed to bind radionuclides to EGFR-expressing cells, for example to visualize the cells or as a cytotoxic treatment of the cells. A variety of radionuclides are available for the production of radioconjugated antibodies. Examples include 212Bi, 131I, 131In, 90Y, and 186Re.

Those of ordinary skill in the art will recognize that a large variety of possible moieties can be coupled to the polypeptidic EGFR-binding agents of the disclosure, such as those comprising an antibody variable region (e.g. antibodies or antibody fragments comprising an EGFR-binding antibody variable region) (see, for example, Cruse and Lewis, 1989, the entire contents of which are incorporated herein by reference). Coupling may be accomplished by any chemical reaction that will bind a moiety and an EGFR-binding agent of the disclosure, so long as these retain their respective activities/characteristics for the intended use thereof. This linkage can include many chemical mechanisms, for instance covalent binding, affinity binding, intercalation, coordinate binding and complexation.

For example, conjugates of a polypeptidic EGFR-binding agent of the disclosure, such as an antibody and an effector agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987).

Carbon-14-labeled 1-isothiocyanatobenzyl-3-methyldiethylene triaminepentaacetic acid (MX-DTPA) is an exemplary chelating agent for conjugation of radionucleotide to the antibody (see, e.g. WO94/11026).

Pharmaceutical Compositions

The disclosure also provides pharmaceutical compositions comprising an EGFR-binding agent or conjugate or radioconjugate described herein as an active ingredient and a pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin.

A pharmaceutical composition is formulated to be compatible with its intended route of administration. Examples of routes of administration include parenteral, e.g. intravenous, intradermal, subcutaneous, oral (e.g. inhalation), transdermal (i.e., topical), transmucosal, and rectal administration.

In one embodiment, the active ingredient is prepared with a carrier that will protect it against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In one embodiment, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms are dictated by and directly dependent on the unique characteristics of the active ingredient and the particular therapeutic effect to be achieved, and the limitations inherent in the art of preparing such an active ingredient for the treatment of individuals.

The formulation can also contain more than one active ingredient as necessary for the particular indication being treated, optionally those with complementary activities that do not adversely affect each other. Alternatively, or in addition, the pharmaceutical composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

METHODS AND USES

The disclosure also provides uses and methods relating to the EGFR-binding agents described herein.

Detecting EGFR-Expressing Cells

The EGFR-binding agents, conjugates and pharmaceutical compositions of the present disclosure are useful for detecting cells that express EGFR. Accordingly, the disclosure provides a use of the EGFR-binding agents described herein for targeting, binding and/or detecting EGFR-expressing cells. Optionally, the cells are cancer cells, including, but not limited to, breast cancer cells, including triple negative breast cancer cells, colon cancer cells, colorectal cancer cells, pancreatic cancer cells, breast cancer cells, gastric cancer cells, prostate cancer cells, liver cancer cells, pancreatic cancer cells, lung cancer cells, melanoma cells, brain cancer cells and head and neck squamous cell carcinoma cells In one embodiment, the EGFR-binding agents, conjugates, and pharmaceutical compositions described herein are useful for targeting, binding and/or detecting cell surface expression of EGFR-expressing cells.

In another embodiment, the EGFR-binding agents, conjugates and pharmaceutical compositions described herein are useful for targeting, binding, detecting and/or localizing EGFR.

In another embodiment, the EGFR-binding agents, conjugates and pharmaceutical compositions described herein are useful for targeting, binding and/or detecting EGFR in cell lysates.

In yet another embodiment, the EGFR-binding agents, conjugates and pharmaceutical compositions described herein are useful for detecting and/or quantitating levels of expression of EGFR in a sample, optionally in an EGFR expressing cell. In one embodiment, the EGFR-binding agents, conjugates and pharmaceutical compositions are used to detect and/or quantitate cellular EGFR levels. In another embodiment, the EGFR-binding agents, conjugates and pharmaceutical compositions are useful for detecting and/or quantitating cell surface EGFR levels.

In general, the use of binding agents for detection of analytes, such as total cellular or surface-expressed EGFR protein, is well known in the art and may be achieved through the application of numerous approaches. These methods are generally based upon the detection of a label or marker, such as radioactive, fluorescent, biological and enzymatic tags. Examples of methods include, but are not limited to, Western blotting, enzyme linked immunosorbent assay (ELISA), immunofluorescence, immunohistochemistry and flow cytometry.

The EGFR-binding agents, conjugates and pharmaceutical compositions of the present disclosure are also useful for reducing and/or eliminating the level or amount of EGFR protein in a cell. Optionally, the cell is a EGFR-positive cancer cell, including, but not limited to, breast cancer cell, including but not limited to, a triple negative breast cancer cell, a pancreatic cancer cell, colorectal cancer cell, colon cancer cell, gastric cancer cell, prostate cancer cell, liver cancer cell, pancreatic cancer cell, lung cancer cell, melanoma cell, brain cancer cell and head and neck squamous cell carcinoma cell. The EGFR protein in an EGFR-expressing cell is optionally reduced by at least 5, 10, 15, 20, 25, 30, 35, 40, 45, 50, 55, 60, 65, 70, 75, 80, 85, 90, 95, 96, 97, 98 or 99%; or by 100%.

Targeting EGFR-Expressing Cells to Immune Cells

Further, the EGFR-binding agents, conjugates and pharmaceutical compositions of the present disclosure are useful for engaging, targeting and/or binding cells of the immune system.

For example, in one embodiment described above, the EGFR-binding agent is a bispecific antibody where one of the binding specificities is for EGFR and the other binding specificity is for an antigen expressed on an immune cell such as a T cell, macrophage or NK cell. As described above, one example of a bispecific antibody that targets T cells is a bispecific T-cell engager (BiTE).

In another embodiment described above, the EGFR-binding agent is an EGFR-binding chimeric antigen receptor (CAR) which includes an EGFR-binding agent of the disclosure, such as an EGFR-binding scFv as its antigen-binding/targeting domain.

Accordingly, the bispecific antibodies and chimeric antigen receptors described herein are useful for targeting immune effector cells to EGFR-expressing cells.

Also provided are methods for targeting EGFR-expressing cells comprising exposing the EGFR-expressing cells to an immune effector cell expressing a CAR of the disclosure, or to a combination of a bispecific antibody of the disclosure and an immune effector cell specifically bound by the bispecific antibody.

Targeting immune effector cells to EGFR-expressing cells through these methods may be useful for eliminating, and/or shifting the phenotype of, EGFR-expressing cells from a cancerous phenotype towards a less cancerous or non-cancerous phenotype. In addition, targeting immune effector cells to EGFR-expressing cells may be useful for treating diseases where EGFR is expressed or overexpressed such as cancer.

Diagnostic Methods

The EGFR-binding agents disclosed herein are useful in the detection/quantitation of EGFR in patient samples or in control samples of healthy individuals and accordingly may be useful diagnostics. For example, the binding agents of the disclosure can be used to detect/quantitate total cellular expression of EGFR and/or cell-surface expressed EGFR. As used herein, the term "diagnostics" encompasses screening, stratification, monitoring and the like.

In one embodiment, the EGFR-binding agents are used to detect EGFR expressing cells, optionally cancer cells such as breast cancer cells.

In another embodiment, the EGFR-binding agents are used for detecting/quantitating expression of EGFR. In another embodiment, the EGFR-binding agents described herein can be used to detect/quantitate expression of EGFR in a sample.

For example, EGFR-binding agents of the disclosure, such as the antibodies and antibody fragments of the disclosure, may be used for practicing any one of various assays, e.g. immunofluorescence, flow cytometry or ELISAs, to detect/quantitate EGFR levels in a sample.

In one embodiment, the sample is a patient sample, such as a cancer sample from a cancer patient. Alternately, the sample may be a control sample from a healthy individual. Embodiments of the sample include but are not limited to, a sample of cultured cells, cultured cell supernatant, cell lysate, serum, blood plasma, biological fluid or biological tissue. In other embodiments, the sample is obtained from a cancer. In certain embodiments, the sample is a biopsy sample.

Treatment of Cancer

EGFR has been shown to play an important role in various cancers, including breast cancer and specifically triple negative breast cancer, and colon or colorectal cancer.

Accordingly, the EGFR-binding agents and pharmaceutical compositions of the present disclosure may be useful for treating a cancer, for example a breast cancer, a colon cancer or a colorectal cancer.

In one embodiment, the EGFR-binding agents and pharmaceutical compositions described herein may be used in a method for treating cancer, the method comprising administering an effective amount of a EGFR-binding agent or pharmaceutical composition disclosed herein to an animal or cell in need thereof, optionally wherein the cancer is breast cancer, optionally triple negative breast cancer, a colon cancer or a colorectal cancer.

In another embodiment, a use of the EGFR-binding agents and pharmaceutical compositions described herein for treating cancer in a subject in need thereof, optionally wherein the cancer is breast cancer, optionally triple negative breast cancer, a colon cancer or a colorectal cancer is provided. In a further embodiment, a use of the EGFR-binding agents and pharmaceutical compositions described herein for preparing a medicament for treating cancer in a subject in need thereof, optionally wherein the cancer is breast cancer, optionally triple negative breast cancer is provided, a colon cancer or a colorectal cancer.

In another embodiment, an effective amount of an EGFR-binding agent or pharmaceutical composition disclosed herein may be used for treating or preventing a cancer, optionally wherein the cancer is breast cancer, optionally triple negative breast cancer, a colon cancer or a colorectal cancer. In another embodiment, an EGFR-binding agent or pharmaceutical composition disclosed herein may be used in the preparation of a medicament for treating or preventing a cancer, optionally wherein the cancer is breast cancer, optionally triple negative breast cancer, a colon cancer or a colorectal cancer.

In yet another embodiment, an effective amount of an EGFR-binding agent or pharmaceutical composition disclosed herein may be used for in treating or preventing a cancer, optionally wherein the cancer is breast cancer, optionally triple negative breast cancer, a colon cancer or a colorectal cancer.

As described above, the present disclosure provides conjugates comprising (1) an EGFR-binding agent and (2) an effector agent, where the effector agent is optionally a toxin or an anti-neoplastic agent.

Accordingly, the present disclosure provides a method of using a conjugate disclosed herein for treating a cancer, the method comprising administering an effective amount of an EGFR-binding agent or pharmaceutical composition disclosed herein to an animal or cell in need thereof, optionally wherein the cancer is breast cancer, optionally triple negative breast cancer, a colon cancer or a colorectal cancer.

In one embodiment, a use of a conjugate described herein for treating cancer in a subject in need thereof, optionally wherein the cancer is breast cancer, optionally triple negative breast cancer, a colon cancer or a colorectal cancer is provided. In a further embodiment, a use of an conjugates described herein for preparing a medicament for treating cancer in a subject in need thereof, optionally wherein the cancer is breast cancer, optionally triple negative breast cancer, a colon cancer or a colorectal cancer is provided.

In one embodiment, an effective amount of a conjugate disclosed herein is used for treating or preventing a cancer, optionally wherein the cancer is breast cancer, optionally triple negative breast cancer, a colon cancer or a colorectal cancer. In another embodiment, an conjugates disclosed herein is used in the preparation of a medicament for treating or preventing a cancer, optionally wherein the cancer is breast cancer, optionally triple negative breast cancer, a colon cancer or a colorectal cancer.

In yet another embodiment, an effective amount of a conjugate disclosed herein is used for treating or preventing a cancer, optionally wherein the cancer is breast cancer, optionally triple negative breast cancer, a colon cancer or a colorectal cancer.

As used herein, the terms "subject" and "animal" include all members of the animal kingdom, in one embodiment the subject is a mammal. In a further embodiment the subject is a human being. In one embodiment, the subject is a patient having a disease, such as a cancer, associated with EGFR-expressing cells.

The term "a cell" includes a single cell as well as a plurality or population of cells.

An effective amount of an EGFR-binding agent, conjugate or pharmaceutical composition of the disclosure relates generally to the amount needed to achieve a therapeutic objective. As noted above, this may be a binding interaction between the EGFR-binding agent and EGFR that, in certain cases, interferes with the functioning of EGFR.

The amount required to be administered will furthermore depend on the binding affinity of the EGFR-binding agent for EGFR, and will also depend on the rate at which an administered EGFR-binding agent is depleted from the free volume of the subject to which it is administered. Common ranges for therapeutically effective dosing of an EGFR-binding agent, conjugate or pharmaceutical composition of the disclosure may be, by way of non-limiting example, from about 0.1 mg kg body weight to about 50 mg/kg body weight. Common dosing frequencies may range, for example, from twice daily to once a week.

Efficaciousness of treatment is determined in association with any known method for diagnosing or treating the particular cancer. Alleviation of one or more symptoms of the cancer indicates that the antibody confers a clinical benefit.

As used herein, "treating or preventing a cancer" includes, but is not limited to, reversing, alleviating or inhibiting the progression of the cancer or symptoms or conditions associated with the cancer. Preventing includes preventing occurrence of the cancer or symptoms or conditions associated with the cancer or preventing worsening of the severity of the cancer or symptoms or conditions associated with the cancer. Accordingly, "treating or preventing the cancer" optionally includes the prophylactic treatment of a subject in order to prevent or reduce the incidence or recurrence of the cancer or symptoms or conditions associated with the cancer.

In one embodiment, the active ingredient may be used in combination with at least one additional therapeutic agent. Accordingly, the application provides a method of detecting, preventing or treating a cancer using the EGFR-binding agents, conjugate or pharmaceutical compositions disclosed herein in combination with at least one additional therapeutic agent. An additional therapeutic agent may be administered prior to, overlapping with, concurrently, and/or after administration of the active ingredients. When administered concurrently, the EGFR-binding agents, conjugates or pharmaceutical compositions and an additional therapeutic agent may be administered in a single formulation or in separate formulations, and if administered separately, then optionally, by different modes of administration. The combination of one or more EGFR-binding agents, conjugates or pharmaceutical compositions and one or more other therapeutic agents may synergistically act to combat the cancer.

Embodiments of the additional therapeutic agent include additional EGFR-binding agents, additional EGFR-binding conjugates, additional EGFR-binding pharmaceutical compositions, cytokines, growth factor inhibitors, immunosuppressants, anti-inflammatory agents, metabolic inhibitors, enzyme inhibitors, anti-neoplastic agents, cytotoxic agents and/or cytostatic agents. Such combination therapies may advantageously utilize lower dosages of an administered active ingredient, thus avoiding possible toxicities or complications associated with monotherapy. In one embodiment, the additional therapeutic agent is an anti-EGFR antibody such as nimotuzumab or matuzumab. In another embodiment, the additional therapeutic agent is an antibody for an ErbB receptor.

Screening Assays

The disclosure also provides methods (also referred to herein as "screening assays") for identifying modulators, i.e., test agents (e.g. peptides, peptidomimetics, small molecules or other drugs) that modulate or otherwise interfere with the binding of a protein disclosed herein with EGFR.

The test agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection (see, e.g. Lam, 1997).

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Phage Display Antibody (Ab) Technology:

Phage-displayed Ab libraries are a powerful technology for the generation of therapeutic Abs. Highly complex libraries of >$10^{10}$ independent Ab fragments are displayed on phage particles as coat protein fusion molecules and screened to isolate Ab that recognize antigens of interest. The present inventors established synthetic Ab libraries with antigen-binding sites constructed entirely from engineered sequences. These Abs use an optimized human framework, and are thus minimally immunogenic when used as potential therapeutics. The synthetic Abs are highly stable, and their human framework and antigen combining sites can be tailored to optimize affinity, specificity and efficacy.

Selection, Characterization and Optimization of EGFR Dimerization Loop-Binding Fabs:

The present inventors took a 'structure-directed' approach to selecting for antibodies that could potentially bind to common structural elements of ErbB receptors that play a critical role in receptor dimerization. A library was generated based upon a graft of the Domain II, cysteine-rich, dimerization loop of EGFR (Residues 240-267, CPPLMLYNPT-TYQMDVNPEGKYSFGATC) (SEQ ID NO:57) replacing a segment within the heavy chain CDRH3 of a Library F template (TVRGSKKPYFSGWAM) (SEQ ID NO:58) Fab, randomizing other CDR's of the Fab, as well as certain framework residues. This dimerization loop is present in all ErbB receptors (albeit with some variation in sequence), exhibits absolute sequence conservation at select residues within the loop and has been shown to be critical for dimerization and downstream transphosphorylation and signaling events [Garrett, Cell, 2002].

Figure 1:
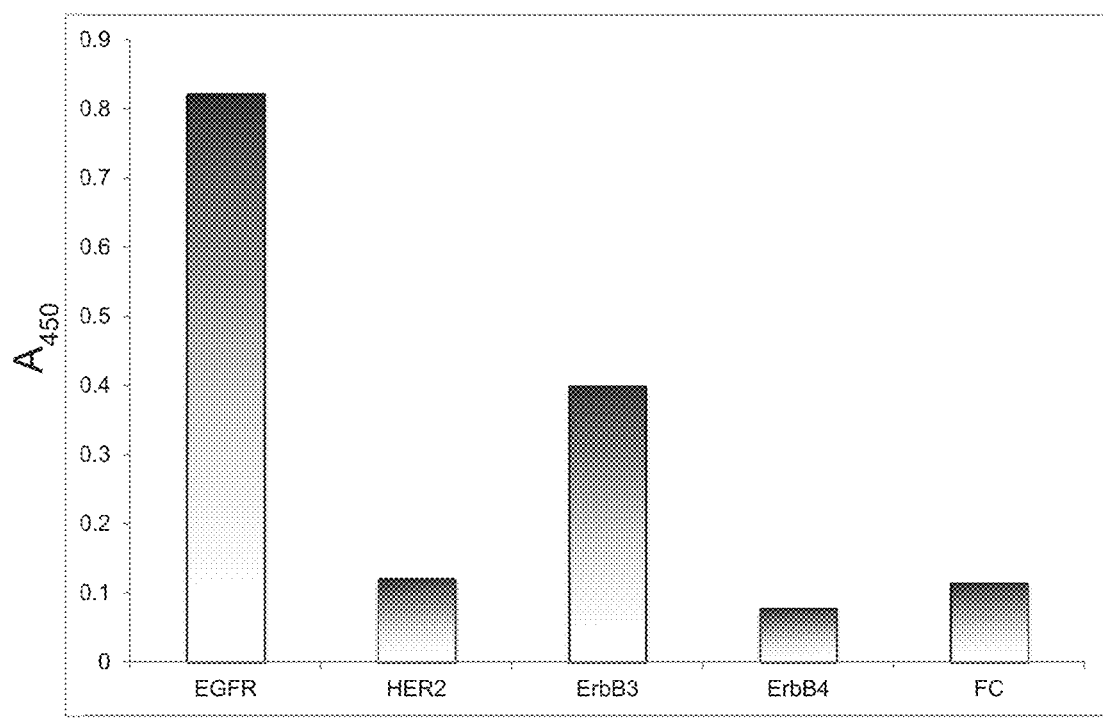
FIG. 1 shows single point Fab-phage ELISA revealing bi-specificity for both EGFR and ErbB3.

Selections were conducted in vitro against purified, plate-immobilized EGFR and led to the isolation of a Fab-phage molecule (DL06) that contained the grafted dimerization loop of EGFR in CDR-H3 of the antibody framework with bi-specificity for both EGFR and ErbB3 (FIG. 1). This molecule exhibited an apparent affinity of >100 nM by multi-point, competitive ELISA using purified EGFR and thus an additional round of selections was undertaken in which the dimerization loop was homology scanned, randomizing residues at each position of the CDR-H3 loop to substitute physicochemically similar amino acids and re-randomizing the other CDRs.

Figure 2:
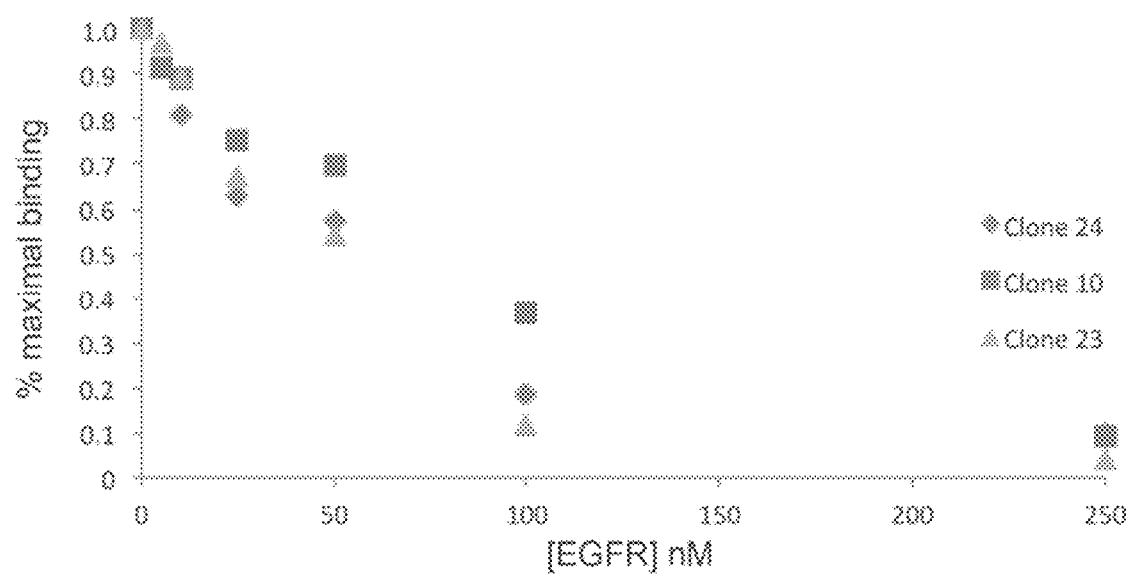
FIG. 2 shows multi-point competitive ELISA with purified EGFR indicates affinity of ~50 nM for all three affinity matured clones.
Figure 3:
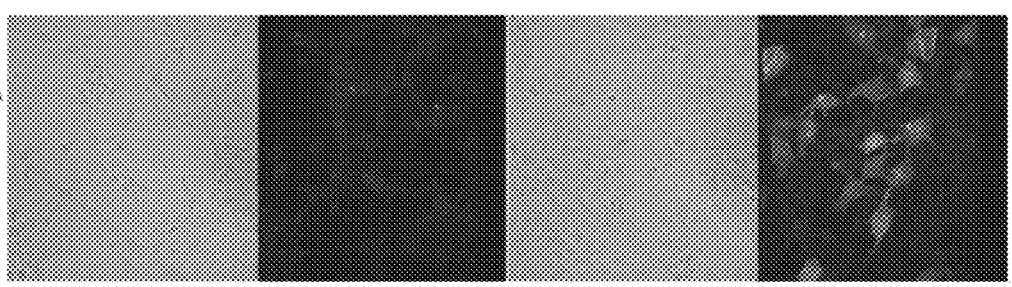
FIG. 3 shows pBABE-EGFR transfected 293T cells stained with EGFR-Binding Fab DLO6 AM Clone 10 and Alexa 488-labeled anti-FLAG.
Figure 4:
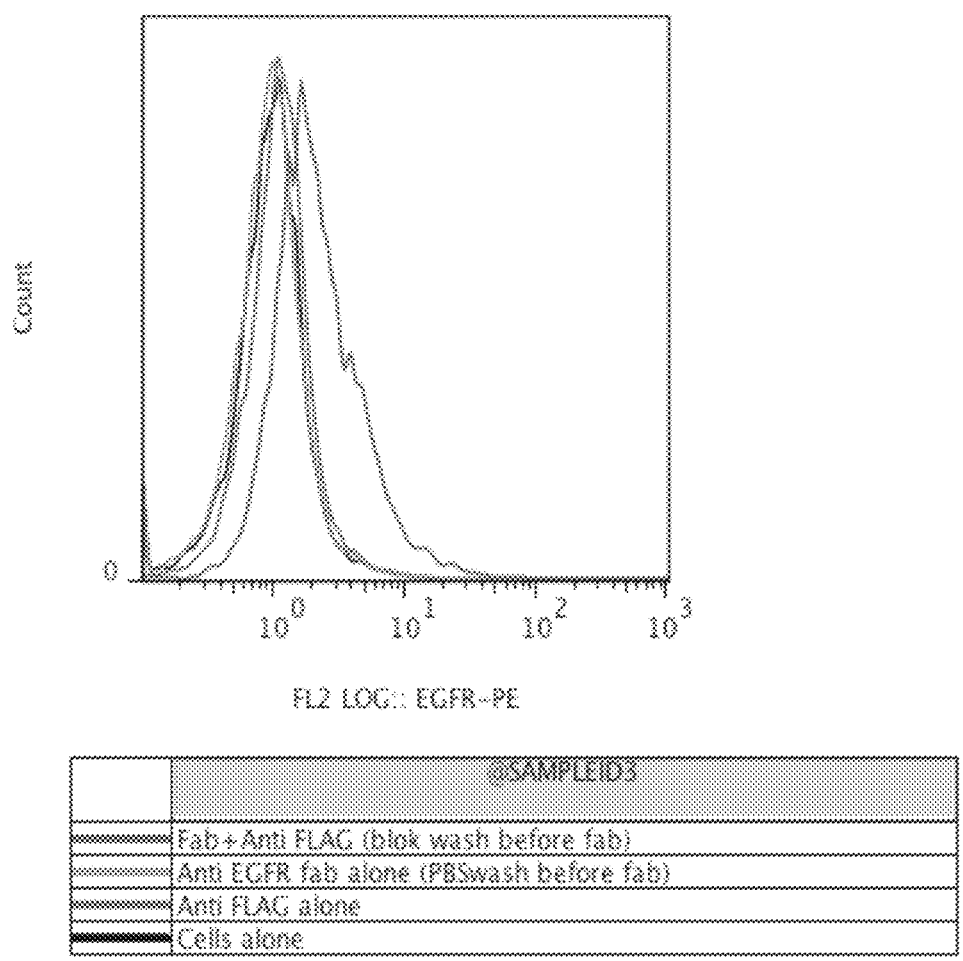
FIG. 4 shows flow cytometric analysis reveals population of EGFR over-expressing MDA-MB-231 breast cancer cell line that stains positively using EGFR-Binding Fab DL06 AM Clone 10.
Figure 5:
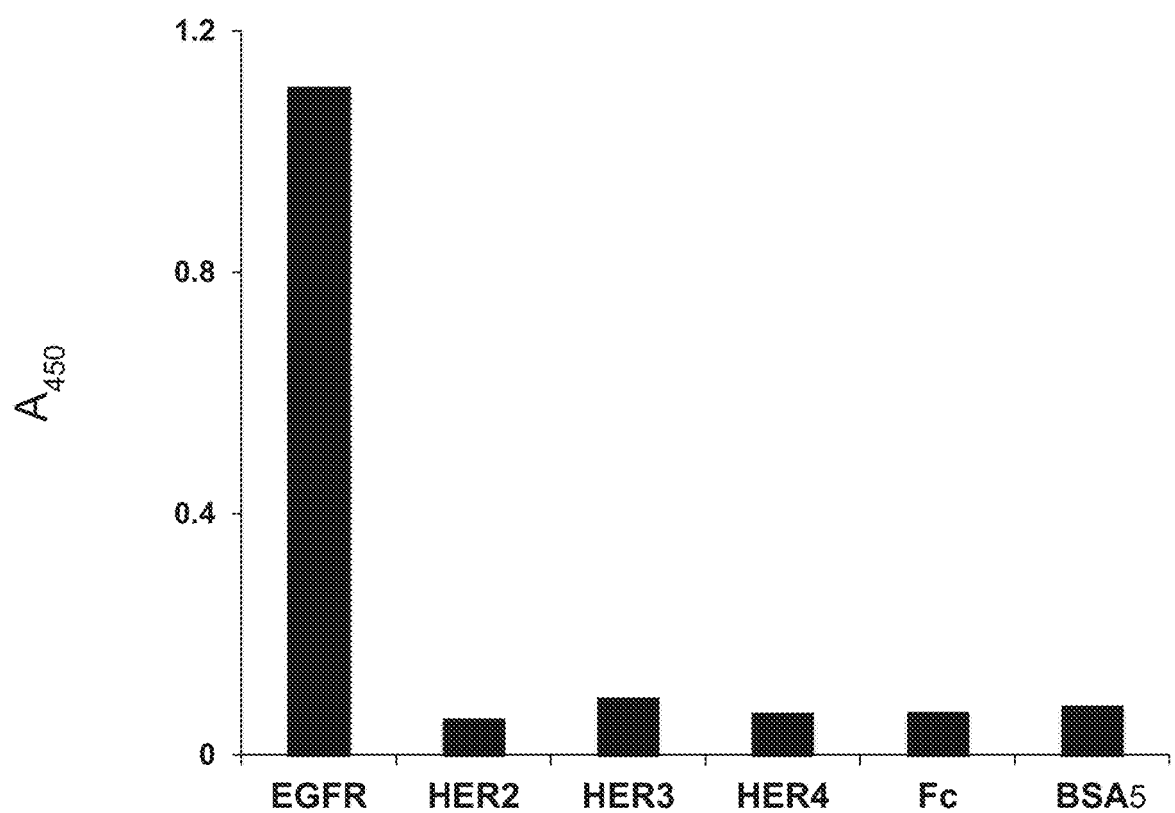
FIG. 5 shows the specificity of the isolated, affinity matured EGFR-Binding Fab DL06 AM Clone 10 was confirmed by ELISA against immobilized ErbB family members revealing exclusive specificity to EGFR.

Additional rounds of selections resulted in the isolation of Fab molecules with improved affinities of ~50 nM (FIG. 2) as purified Fabs (DL06 AM Clone 10, DL06 AM Clone 24, and DL06 AM Clone 23), albeit with specificity only for EGFR (See FIG. 5). Nevertheless, evaluation of Fab clone DL06 AM Clone 10 confirmed cell binding in EGFR-transfected, fixed 293T cells by immunofluorescence microscopy (FIG. 3), as well as by flow-cytometry in live MDA-MB-231 EGFR-over-expressing breast cancer cells (FIG. 4). In the same cells, previously published techniques were used to assess the degree of ligand-induced homodimerization of EGFR in the presence and absence of the Fab. The design strategy employed to obtain the Fabs described within this disclosure was aimed at isolating antibody clones that specifically bind the dimerization loop in EGFR that mediates critical protein-protein interactions required for dimerization.

Figure 6:
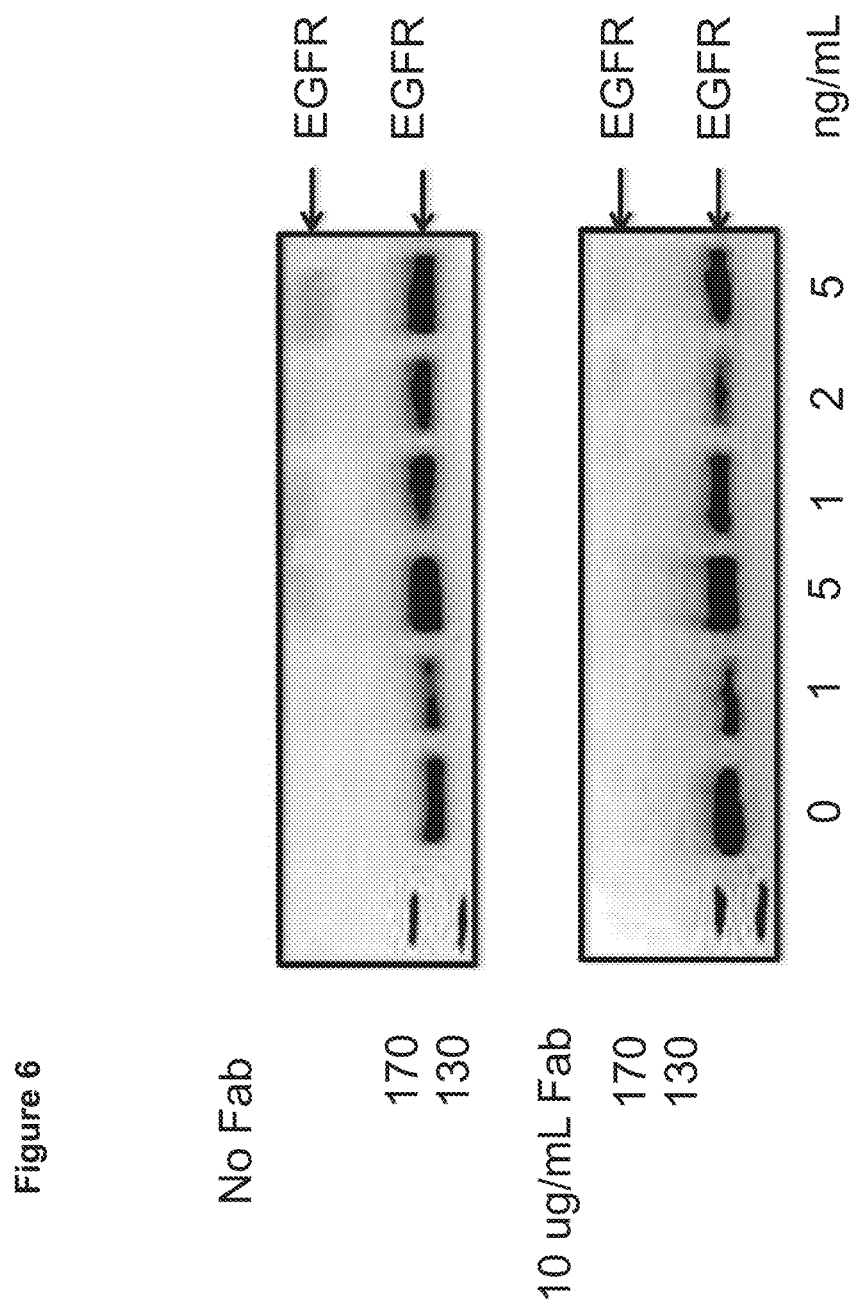
FIG. 6 shows cells pre-incubated with Fab DL06 AM Clone 10, inhibit cross-linking of cell-surface EGFR with cell-impermeant $BS^3$ following stimulation with a range of [EGF]. Western blots of cell lysates treated in this fashion confirm the ability of this to block EGF-induced EGFR homodimerization.

To test the ability of the Fab to block this loop and inhibit dimerization, EGFR-expressing triple negative breast cancer (TNBC) cell lines (MDA-MB-231) were pre-incubated with 10 ug/mL DL06 AM Clone 10 (see FIG. 30 for sequence of CDRs of DL06 AM Clone 10). Cells were then stimulated with a range of [EGF] and then the receptor was cross-linked at the end of stimulation (10 minutes) using a cell impermeant, bifunctional cross-linking reagent (bis sulfosuccinimidyl suberate—BS3). Results clearly show that DL06 AM Clone 10 is capable of inhibiting dimerization required for receptor activation (FIG. 6).

Figure 7:
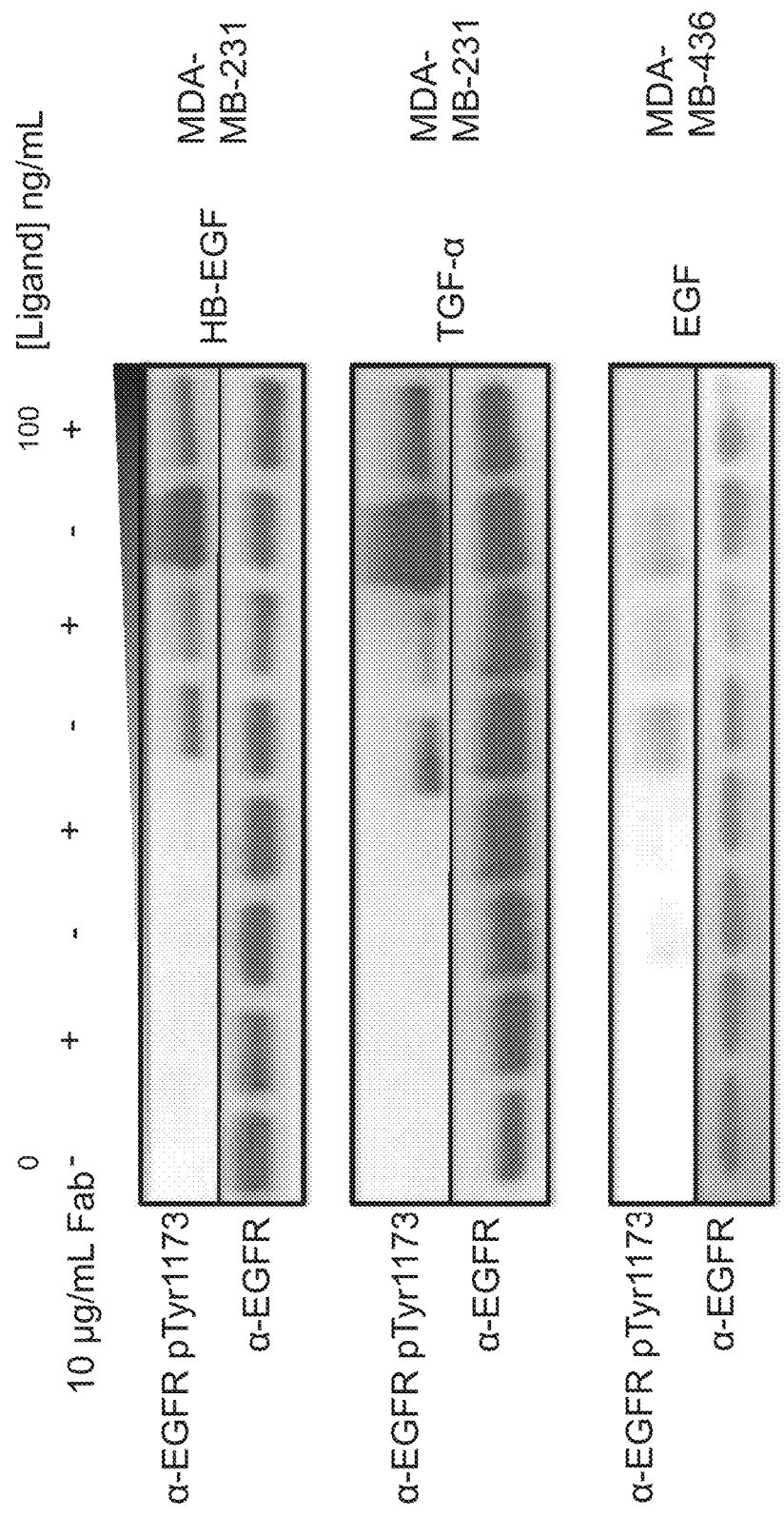
FIG. 7 shows pre-incubation of cells with Fab DLO6 AM Clone 10 inhibits the activation of EGFR by several EGFR specific-ligands in various EGFR expressing triple negative breast cancer cell lines (TNBC) as confirmed by expression by Western blot comparison of EGFR activation/phosphorylation by anti-pTyr1173 antibodies to overall EGFR.

To further strengthen these results, MDA-MB-231 cells, as well as another EGFR-expressing TNBC cell line—MDA-MB-436 were pre-incubated with 10 ug/mL DL06 AM Clone 10. It was then stimulated with either EGF or other EGFR ligands (HB-EGF and TGF-alpha) to assess activation of EGFR as evidenced by phosphorylation residue Tyr1173 in the cytoplasmic domain of EGFR. In accord with inhibition of homodimerization, clear evidence of the inhibitory activity of DL06 AM Clone 10 was obtained, and as diminished staining of EGFR with anti-pTyr1173 antibodies (10 in comparison to load control western blots specific for EGFR alone) in cells pre-blocked with DL06 AM Clone 10 (FIG. 7) was observed.

Figure 8:
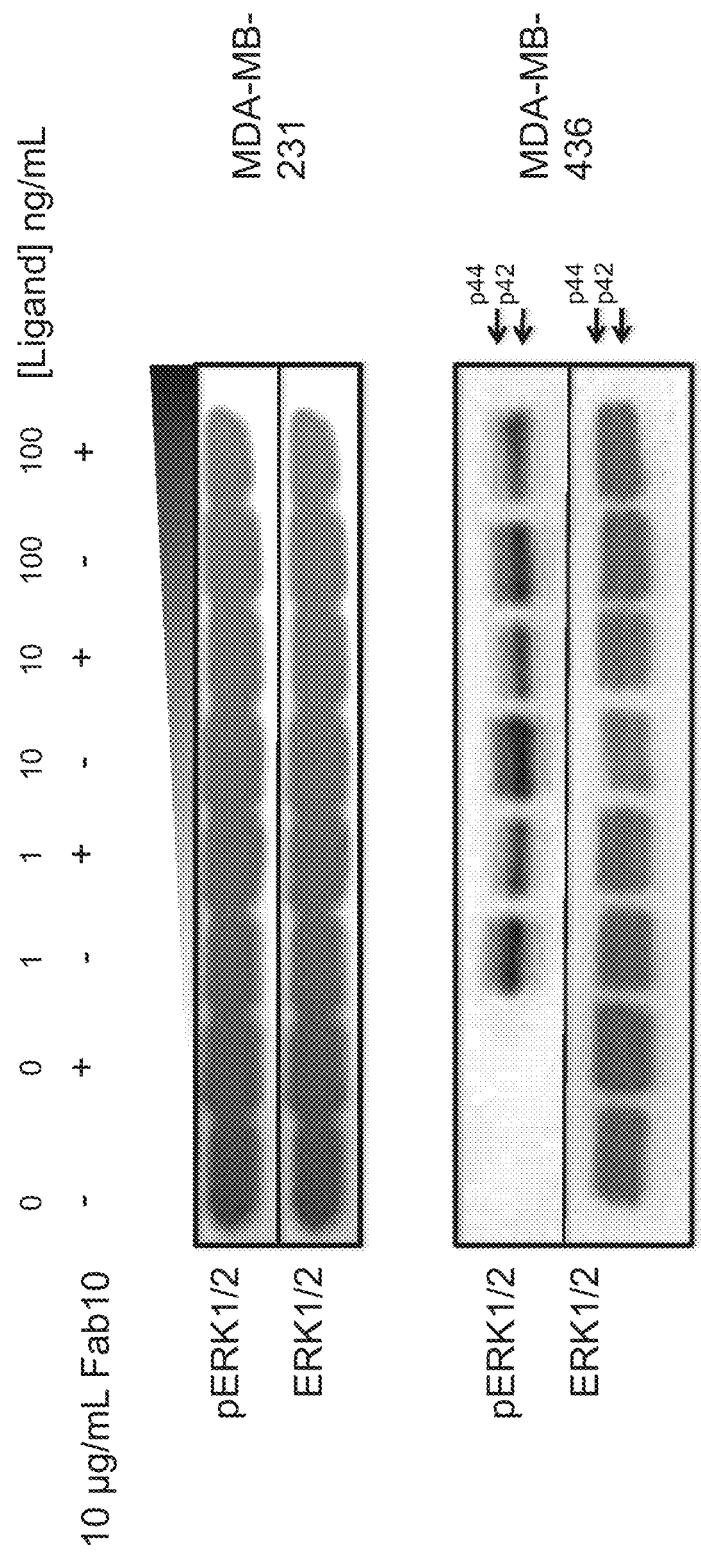
FIG. 8 shows pre-incubation of cells with Fab DL06 AM Clone 10 inhibits the activation of signaling molecules downstream of EGFR by EGF in the MDA-MB-436 EGFR-expressing TNBC cell line but not in MDA-MB-231 cells (which possess an activating Ras mutation) as confirmed by Western blot of ERK1/2 phosphorylation by anti-p-Thr202/Tyr204 antibodies in comparison to overall ERK1/2.
Figure 9:
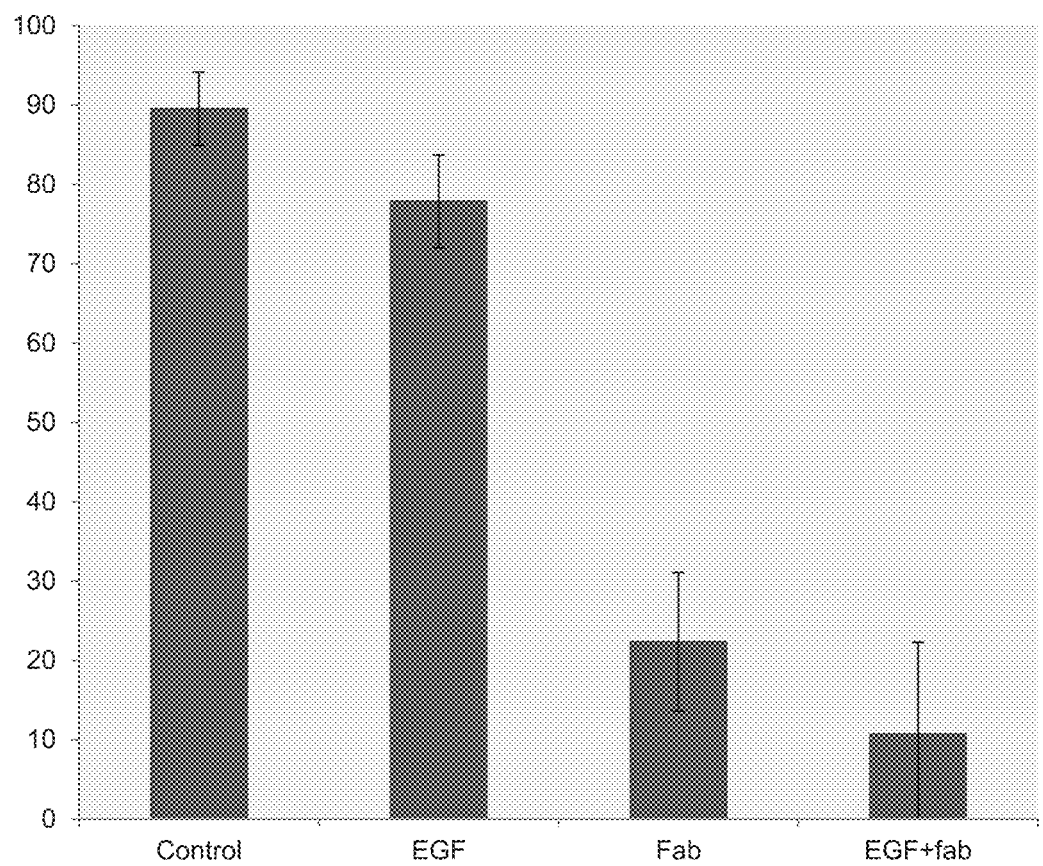
FIG. 9 shows cultivation of MDA-MB-231 cells in the presence of EGFR-binding Fab DL06 AM Clone 10 inhibits proliferation under both serum-starved and serum-fed conditions.

Previous characterization of TNBC cells suggests that mutations in some of these cell lines may contribute EGFR-independent growth signals that uncouple downstream signals from receptor. The MDA-MB-231 cell line is one such cell line, known to possess a mutation in the Ras oncogene that constitutively activates downstream effectors such ERK1/2. To determine whether DL06 AM Clone 10 was capable of inhibiting signals further downstream of EGFR, the phosphorylation of ERK1/2 at pThr202/Tyr204 was assessed in both the MDA-MB-231 and 436 cell lines in the presence and absence of Fab. As anticipated, pre-incubation of DL06 AM Clone 10 with cells for one hour inhibited the EGF-induced activation of ERK1/2 in the 436 cell line, but not in the 231 cell line in which downstream is uncoupled from EGFR by activating mutations in the intervening Ras effector (FIG. 8). However, incubation of serum-starved MDA-MB-231 cells supplemented with EGF nonetheless confirmed the anti-proliferative activity of this Fab and its potential as an anti-cancer therapeutic (FIG. 9).

Example 2

This example provides additional details on the affinity maturation process that yielded clones DL06 AM Clone 10, DL06 AM Clone 24, and DL06 AM Clone 23 from clone DL06. In addition, this example describes a second affinity maturation strategy that yielded clone DL06 SR02 (Fab 8708). This example also describes Fab H (Fab 8709) which was obtained from a separate and distinct, non-graft, tailored diversity library referred to as library F that is described Persson, J M B, 2013.

Background

Structural models of the EGF-mediated EGFR homodimer reveal extensive receptor-receptor contacts mediated by a "dimerization loop" in domain II (Garrett et al, 2002, Ogiso, 2002). In the inactive conformation, the dimerization loop interacts with domain IV residues to maintain a tethered, closed conformation (Ferguson et al., 2003), but upon ligand binding, it undergoes conformational rearrangement allowing intermolecular contact with a second EGFR via the face opposite the ligand binding site (FIG. 10A) (Garrett et al., 2002, Ogiso, 2002). The dimerization loop mediates critical contacts required for EGFR signaling (FIG. 10B), and its deletion ablates ligand-induced receptor activation (Garrett et al., 2002). Nevertheless, exposure of the loop alone is insufficient for receptor activation and secondary contacts in domains II and IV also contribute functional interactions (Dawson et al., 2005).

Based on these observations, the dimerization loop motif was used to design and construct a structure-directed, phage-displayed Fab library biased toward binding EGFR domain II. The entire dimerization loop sequence was grafted in to CDR-H3 of a human Fab framework (Cho et al., 2003) and other CDRs were diversified. This phage-displayed Fab library was used in binding selections with EGFR, and for comparison, a previously validated naïve synthetic Fab library (Persson et al., 2013) was also screened. Both libraries yielded Fabs with nanomolar dissociation constants that blocked ligand-induced receptor activation, and the epitopes of both Fabs mapped to EGFR domains I and II and did not overlap with epitopes of therapeutic anti-EGFR monoclonal antibodies (mAbs).

Results

Design and Construction of a Structure-Directed Synthetic Antibody Library

The EGFR monomer exists in a dynamic equilibrium between an auto-inhibited conformation, where domains II and IV form an intramolecular interaction, and an extended conformation capable of dimerization (FIG. 10A) (Mattoon et al., 2004). Upon interaction of EGF with the ligand-binding site (between domains I and III), the equilibrium shifts toward the extended conformation that promotes receptor dimerization and activation. Structural analyses have shown that dimerization between EGFR partners is mediated primarily by a 28 residue 3-hairpin dimerization loop in domain II that makes extensive contact with the analogous loop of a partner receptor and adjacent regions on domain II (FIG. 10B) (Lemmon et al., 2014).

To construct a structure-directed antibody library, the dimerization loop sequence of EGFR was grafted so as to replace a segment within the heavy chain CDR-H3 of an anti-maltose-binding protein (MBP) Fab that has been used previously as a scaffold for synthetic Fab libraries (Persson et al., 2013) (FIG. 10C). Single residues on either end of the graft were added and randomized, while CDR-L1 and -L2 were held constant and tailored diversity was introduced into CDR-L3, -H1 and -H2, and in framework residues at IMGT positions 39, 55 and 66, as described (Persson et al., 2013). The new library (named library DL) contained ~5×10$^9$ unique members and sequencing of representative clones verified that all clones contained the EGFR dimerization loop in CDR-H3 and the designed diversity in CDR-L3, -H1 and -H2.

Isolation of Anti-EGFR Fabs from Libraries DL and F

Selections were conducted in parallel against the immobilized F$_c$-tagged extracellular domain (ECD) of the recombinant human EGFR (rhEGFR) using library DL and a previously described library F, which contains random CDR-H3 sequences of various lengths and CDR-H1, -H2, and -L3 diversity identical to that of library DL (Persson et al., 2013). Enrichment of phage titres from both libraries was observed for rhEGFR compared to non-specific control BSA protein. Clonal phage supernatants from round 3 (library F) or round 6 (library DL) were tested by phage ELISA for binding to EGFR and control proteins (BSA and Fc). EGFR-specific clones were isolated from libraries DL and F, and clones of interest were sequenced (FIG. 10D). Library DL yielded a single unique Fab sequence (named DL06), which as expected, contained the dimerization loop sequence from EGFR in the CDR-H3 location. In the case of library F, a high affinity Fab that competed with Fab DL06 for binding to EGFR was focused on (see below).

Affinity of phage-displayed Fab DL06 was assessed using a multi-point competitive ELISA with soluble rhEGFR as described (Sidhu and Fellouse, 2006). rhEGFR inhibited phage-displayed Fab DL06 binding with an $IC_{50}$ of ~200 nM (FIG. 28). To improve the affinity of DL06, the dimerization loop sequence in CDR-H3 was affinity matured. A DL06-based affinity maturation library was constructed by "soft randomizing" the dimerization loop in CDR-H3 in a manner such that each amino acid position contained ~50% wild-type sequence and ~50% mutant sequences (see Methods). The affinity maturation library was subjected to 4 rounds of binding selections with rhEGFR, and screening by competitive phage ELISAs revealed that the highest affinity clone exhibited a seven-fold enhancement in affinity ($IC_{50}$~30 nM). Sequencing revealed that, relative to the parent Fab-DL06, the new Fab (named Fab 8708) contained three substitutions in the dimerization loop CDR-H3 (FIG. 10D).

Epitope-blocking experiments were conducted to determine whether Fab 8708 would block simultaneously binding of the Fabs isolated from library F. Immobilized rhEGFR was incubated with saturating concentrations of purified Fab 8708 protein and binding of Fab-phage was assessed. Fab 8708 blocked both binding of phage-displayed Fab 8708 and a single Fab 8709, suggesting that the two Fabs could have an overlapping epitope.

Characterization of Anti-EGFR Fabs

The specificities of Fab 8708 and Fab 8709 were assessed by ELISA with the four human ErbB family members and specific binding to EGFR was confirmed (FIG. 11A). Optical biolayer interferometry was used to study the kinetics of Fab binding to immobilized rhEGFR. Binding curves were globally fit with a 1:1 model and revealed tight, single-digit nanomolar affinities for both Fabs (FIG. 11B). However, the Fabs differed significantly in their kinetics of binding, with Fab 8709 exhibiting an 18-fold faster on-rate and a 3-fold faster off-rate than Fab 8708. In agreement with the results obtained using Fab-phage, it was also confirmed that both Fabs blocked binding of each other to immobilized rhEGFR (FIG. 11C). Notably, neither Fab was blocked by the therapeutic mAb cetuximab (CTX) and both were only partially blocked by the distinct therapeutic mAb panitumumab (PTMB) (FIG. 11D). Similar results versus both mAbs were obtained by in vitro binding assays (FIG. 11D, upper panels) and on cells (FIG. 11D, lower panels). Taken together, these results confirm that Fab 8708 and Fab 8709 likely share overlapping epitopes, which are distinct from the epitopes recognized by CTX and PTMB.

To confirm specific binding of the Fabs to cell-surface EGFR, Fab binding was assessed by flow cytometry using HEK293F cells transiently transfected with a plasmid designed to express full-length EGFR with a C-terminal GFP fusion (EGFR-GFP). At saturating Fab 8708 or Fab 8709 concentrations, greater than 95% of EGFR-expressing cells (EGFR-293F cells) were labeled, while no significant binding was observed for untransfected HEK293F cells (FIG. 11E). Fab binding to the EGFR-293F cells or to A431 cells that express high levels of endogenous EGFR was quantified by testing a range of Fab concentrations, and both Fabs exhibited saturation behavior (FIG. 11F) with $EC_{50}$ values in the low nanomolar range. Taken together, these results show that both Fabs are able to efficiently and specifically recognize both ectopically-expressed and endogenous cell-surface EGFR.

The effects of Fab binding on the activation of EGFR by EGF were assessed by evaluating levels of receptor phosphorylation using western blotting analysis. Treatment of EGFR-positive A431 carcinoma cells with either Fab prior to treatment with EGF inhibited EGFR phosphorylation in a dose-dependent manner (FIG. 11G). Given the antagonistic activity of the Fabs on EGF-mediated signaling, the effects of EGF on Fab binding and observed that pre-incubation of cells with EGF resulted in a shift to higher concentrations of both Fabs required to reach saturation was explored (FIG. 11H). Moreover, it was also observed that both Fabs blocked binding of EGF to immobilized rhEGFR in an ELISA (FIG. 29). Taken together, these results show that both Fabs compete with EGF for binding to the EGFR and consequently act as competitive antagonists of receptor activation.

Characterization of EGFR Epitopes

To assess whether the dimerization loop of EGFR is important for the binding of Fab 8708 and Fab 8709, dose response curves were generated by flow cytometry (FIG. 14) to determine $EC_{50}$ values for binding to cell-surface EGFR and EGFR mutants (FIG. 12A). Fab cell binding assays were conducted with HEK293F cells transfected to express EGFR or one of two EGFR mutants known to inhibit receptor dimerization and activation (Garrett et al, 2002, Ogiso, 2002), namely, EGFR-D28, which lacks the dimerization loop residues C240-C267, and EGFR-DM, which contains two mutations in the dimerization loop (Y251A/R285S). PTMB, which binds to domain III (Voigt et al, 2012), was used as a positive control. As expected, $EC_{50}$ values for PTMB were virtually identical for binding to cells expressing EGFR or EGFR-DM and less than two-fold reduced for binding to cells expressing EGFR-D28. For Fab 8708 and Fab 8709, the $EC_{50}$ values relative to EGFR binding were reduced for binding to both EGFR-DM and EGFR-D28 but the effects were less than three-fold. These results were surprising for Fab 8708, since it was believed that the dimerization loop insertion in CDR-H3 would target binding to the dimerization loop of EGFR, and thus, deletion of the dimerization loop in EGFR was expected to have a much greater effect on Fab binding.

Given the unexpected finding that deletion of the dimerization loop in EGFR had only a minor effect on the binding of Fab 8708, the Fab and mAb epitopes were mapped in further detail by using cells expressing fragments of EGFR. Specifically, flow cytometry was used to assess the binding of PTMB, CTX, Fab 8708 and Fab 8709 to HEK293F cells transfected to express fragments of EGFR comprising single domains (D1, D2, D3, D4), double domains (D1-D2, D2-D3, D3-D4) or triple domains (D1-D2-D3, D2-D3-D4). Binding signals at saturating concentrations were used to construct a comparative heat map (FIG. 12B). Consistent with epitopes centered on domain III, PTMB and CTX bound to EGFR fragments containing domain III (D3-D4 and D2-D3-D4). These results were further confirmed by phage display of EGFR domain III and evaluation of phage binding to immobilized Fab 8708, Fab 8709, CTX, PTMB, EGF and BSA, in which phage binding was observed only to CTX and PTMB (FIG. 15). In contrast, Fab 8708 and Fab 8709 bound to fragments containing domain I (D1, D1-D2, D1-D2-D3) with the strongest binding to the fragment that contained domains I and II (D1-D2). The binding of the two Fabs to cells displaying EGFR-vIII, a natural deletion variant missing all of domain I and most of domain II, including the dimerization loop (Libermann et al., 1984) was also tested. As expected, neither Fab exhibited any binding by flow cytometry, whereas both Fabs exhibited robust binding to cells displaying EGFR under the same conditions (FIG. 12C). Taken together, these results provide evidence that both Fab 8708 and Fab 8709 recognize similar epitopes that are centered on domain I but also involve domain II, and which do not overlap with the epitopes of PTMB and CTX.

Methods

Fab Library Construction

Oligonucleotide-directed combinatorial mutagenesis was used to simultaneously diversify CDR-H3, -H2, -H1 and -L3 in a human Fab framework, as described (Persson et al., 2013). The CDR-H3 sequence was replaced by the 28-residue loop comprising residues Cys240-Cys267 of EGFR with an additional NNC (N=A/G/C/T) codon flanking each side. The CDR-H2, -H1 and -L3 sequences were diversified as described for library F. The mutagenesis reaction was electroporated in to *Escherichia coli* SS320 and the resulting library DL contained $8.4 \times 10^9$ unique members. The library for affinity maturation of Fab DL06 was constructed similarly except that only CDR-H3 was diversified using a mutagenic oligonucleotide in which codons encoding for the dimerization loop (excluding Cys240 and Cys267) were replaced with a mixture comprising 85% of the wild-type base and 5% of each of the other three bases.

Selection and Characterization of EGFR-Binding Fab-Phage

Library phage pools were cycled through rounds of selection for binding to $F_c$-tagged rhEGFR-ECD (R&D, 344-ER-050, Minneapolis, Minn.) immobilized in immunosorption plates (eBioscience Inc., San Diego, Calif.) as described (Sidhu and Fellouse, 2006). After 4-6 rounds of selection, specific binding of individual clones was evaluated by phage ELISA as described (Birtalan et al., 2008). Clones that exhibited at least 10-fold greater signals for binding to rhEGFR compared with F or BSA were subjected to DNA sequencing to decode the sequences of the phage-displayed Fabs.

ELISAs

Fabs were expressed and purified as previously described (Hornsby et al., 2015). Purified Fc-tagged ECDs of EGFR (R&D, Minneapolis, Minn., 344-ER) and the other three ErbB family members (R&D, Minneapolis, Minn., 1129-ER, 348-RB, 1131-ER) were adsorbed in individual wells of an immunosorption plate, and binding of Fab to the immobilized proteins was assessed by ELISA using an anti-FLAG Ab-HRP conjugate (Sigma, Oakville, ON) as described (Sidhu et al., 2004). For competition ELISAs, immobilized EGFR was blocked with saturating concentrations of Fab or mAb for 30 min prior to the addition of Fab or biotinylated Fab (btFab). btFabs were generated by mutating the C-terminus of the Fab heavy chain to possess an Avi tag using standard molecular techniques, expressing in biotin ligase-transformed *E. coli* cells using published methods (Kay et al., 2009) and purifying as above. Biotinylated Fabs were detected using a 0.1 μg/mL solution of streptavidin-HRP in PBS with 0.2% BSA and 0.05% Tween and developed as above.

Biolayer Interferometry

Binding kinetics were determined by biolayer interferometry using a ForteBio Octet Red384 system (Pall Corporation, Menlo Park, Calif.) with Fab proteins immobilized on amine-reactive generation-2 biosensors (ForteBio, Menlo Park, Calif.) according to the manufacturer's instructions. Sensor-captured Fabs were exposed to serial dilutions of rhEGFR-ECD-Fc, and association and dissociation was assessed by the shift in wavelength (nm) after subtracting blank responses. Analysis was performed using a 1:1 Langmuir model and globally fit to determine $k_{on}$ and $k_{off}$ values using Octet Software (ForteBio). $K_D$ was calculated as the ratio of $k_{off}/k_{on}$.

Flow Cytometry

Flow cytometry was used to evaluate Fab binding to cell surface EGFR and various mutants. Mutants were generated from the EGFR-GFP construct (Carter and Sorkin, 1998) using standard molecular biology techniques, constructs were sequence verified, and 293F cells were transfected with DNA purified using the Maxi-prep system (Qiagen, Toronto, ON), as described (Longo et al., 2013). Transfected cultures were cultivated for at least 48 h (DMEM media, 10% FBS, 37° C. in 5% $CO_2$) prior to analysis. Adherent cells were grown to ~80% confluency, harvested with cell dissociation buffer and collected as transfected 293F cells by centrifugation at 2000 g. Cells were stained by first washing with ice-cold PBS, blocking with 0.1% goat serum in PBS, incubating with Fab or mAb for 1 h on ice, washing, incubating with mouse anti-FLAG M2 R-PE-labeled (Prozyme-Phycolink, Hayward, Calif., PJ315) or goat anti-human (Fab')$_2$ fragment IgG PE-labeled (Beckman Coulter, Mississauga, ON, PN1M1626) secondary antibody, and fixing in 2% paraformaldehyde in PBS. Immuno-stained cells were analyzed on a Miltenyi Biotec MACS Quant VYB cytometer collecting a minimum of $10^3$ cell events after exclusion of debris, aggregates and low-GFP expressing cells (for cells transfected with a plasmid designed for the expression of GFP). Cells stained with secondary alone were used as non-binding controls and cell-binding data were represented as histogram plots using FlowJo Software Version 9.3 (Ashland, Oreg.). To obtain binding curves and affinity estimates, log [Fab] was plotted vs. the % PE-positive cells and fit using the log [inhibitor] versus response equation with standard fit in Prism Version 7.0 (Graphpad, La Jolla, Calif.).

EGFR Signaling Assays

To evaluate the effects of Fabs on EGFR signaling, EGF-induced receptor phosphorylation was assessed by western blot analysis as described[49]. In brief, serum-starved A431 carcinoma cells were pre-treated with varying concentrations of Fab in serum-free media and incubated at 37° C. for 1 h before stimulating with 50 ng/mL EGF (R&D, Minneapolis, Minn., 236-EG-200) for 15 min in the presence of Fab. Cells were collected on ice by scraping in to lysis buffer and phosphorylation of receptor was assessed by separation of 10 μL lysate on an SDS-PAGE gel and transfer to PVDF support using standard methods. The blot was treated with a 1:1000 dilution of rabbit polyclonal anti-pEGFR Tyr1173 antibody (Cell Signaling, Danvers, Mass., #4407) and a 1:5000 dilution anti-rabbit-HRP secondary antibody (Santa Cruz Biotech, Santa Cruz, Calif., sc-2004) in PBS, 0.2% Tween, followed by development with a chemiluminescent substrate (Biorad, Mississauga, ON). Western blots detecting total EGFR as load control were developed using rabbit polyclonal anti-EGFR antibodies (Santa Cruz Biotech, Santa Cruz, Calif., sc-03).

Estimation of Fab-Phage Affinity by Multi-Point Competitive ELISA

Purified Fc-tagged ECD of EGFR (R&D, 344-ER) was adsorbed in individual wells of an immunosorption plate, and binding of Fab-phage to immobilized protein was assessed by multipoint competition ELISA using soluble EGFR ECD as competitor. Percent maximal binding was calculated by dividing signals observed in the presence of soluble EGFR by signals measure in the absence of EGFR and the inhibition curve fit using Prism (Graphpad).

EGF Ligand Binding Assay

Recombinant EGF ligand (R&D, CF 236EG-200) was biotinylated by reaction with a 2:1 molar ratio of the N-hydroxysuccinimide ester of biotin (Pierce/Thermo, #21329) as per manufacturers instructions. Unreacted biotin was removed by washing 5× with 500 μL of PBS pH 7.4 in a 3 kDa cutoff centrifugal concentrator tube. Microplates (Nunc) were coated with a 10 μg/mL solution of rhEGFR-ECD overnight at 4° C. with shaking and binding of biotinylated EGF was detected by ELISA with 0.1 μg/mL streptavidin HRP (NEB, 3999S) and quantified at 450 nm after development with TMB substrate.

Fab Binding to Cell Surface wtEGFR, Dimerization Loop and Domain Mutants

Experiments were conducted as described with Fab-binding plots generated from % PE-labeled cell values versus Fab concentration for the EGFR, EGFR-28 and EGFR-DM mutants from which data in FIG. 12A was extracted.

ELISA for EGFR Domain III Binding

EGFR Domain III (residues 311-514—including 34 residues from the N-terminal end of domain IV) was cloned in to a phagemid vector using standard molecular techniques and the binding of phage particles displaying domain III to immobilized Fab, mAb or negative controls evaluated by ELISA as described in the main text. Proteins (Fabs 8708, 8709, CTX, PTMB, EGF and BSA) were immobilized in separate wells of a microplate ON at 4° C. from a 10 μg/mL solution in PBS with shaking at 200 rpm. The measured OD450 nm values were plotted versus phage concentrations and fit using Prism (Graphpad, CA) to assess binding.

Discussion

Following the clinical success and commercialization of CTX and PTMB, investigators have attempted to develop additional anti-EGFR antibodies for therapeutic applications (Machiels et al., 2011, Bleeker at al, 2004, Crombet at al., 2003, Fernandez et al., 1992, Graeven et al., 2006, Murthy et al., 1987). Efforts have been driven by the observation that targeting of alternative epitopes may provide additional potential clinical benefit via several mechanisms. Targeting of an epitope distinct from that of a primary therapy can circumvent mutations that compromise binding and render first line therapies ineffective (Montagut et al., 2012). Further, combinations of non-competitive Abs can offer additional potency outside of Ab-dependent cell cytotoxicity mechanisms by promoting receptor internalization (Friedman et al., 2005) or enhancing inactivation (Klapper et al., 1997) and are proving clinically useful (Ko et al., 2015, Yamahita-Kashima et al., 2011).

Grafting techniques are an attractive means of rationally designing antibodies to target specific epitopes for various applications and there are a growing number of successful examples that have used this strategy (Perchiacca et al., 2012, Barbas et al., 1993, Lee et al., 2007). One purpose of this study was to test the hypothesis that by grafting a receptor interaction domain in to CDR-H3, combined with randomization of additional CDRs, antibodies could be isolated with specificity for the native interaction domain in the target receptor. By targeting the interaction domain by design, the aim was to obtain lead antibodies that would block receptor dimerization and activation, but whose mechanism of action would be distinct from the existing therapeutics PTMB and CTX. It was further sought to compare the grafting strategy with selections using a highly functional naïve synthetic Fab library (Persson et al., 2013).

Using both naïve and structure-directed libraries, Fabs were obtained that bound specifically to cell-surface EGFR with high affinity and antagonized EGF-dependent activation. The success shown here in generating potent antagonists of EGFR signaling from repertoires that do not rely on animals or even immunized sources of Ab diversity confirm that synthetic Ab libraries are up to the task of providing leads for clinical development. Comparison of the epitopes of the Fabs described herein to those of PTMB and CTX further confirmed that synthetic libraries, whether based upon naïve or structure-directed diversity, provide a substantial advantage over conventional immunization techniques and can make accessible novel epitopes from which additional clinical benefit could potentially be obtained. The successful demonstration of the viability of grafting techniques to obtain potent and specific antibodies further adds to the body of literature that supports the use of structure-directed design strategies in protein engineering.

Example 3

The ability of Fab DL06 SR02 (Fab 8708) to block EGF-induced activation of EGFR was assessed in a variety of different EGFR-expressing breast and colon cancer cell lines (FIG. 13). Cells were incubated with or without Fab 8708 before stimulating with 50 ng/mL EGF. Following stimulation of cells, activation and phosphorylation of EGFR in collected cell lysates was visualized by western blot detection of pTyr1773 signals and compared to total EGFR western signals from an anti-EGFR polyclonal antibody. Results show that in the absence of EGF, no activation of receptor is observed and this is not affected by the presence of Fab. Alternately, strong activation signals obtained in the absence of Fab could be, in most cases, completely abrogated by pre-incubation with 50 μg/mL (1 μM) Fab 8708.

Example 4

Imaging of DL06 Fragments labeled with 800CW in A431 xenograft-bearing mice

Molecular imaging of expression level of ErbB1 is important for cancer diagnosis, prognosis, and eligibility for therapy. Accordingly, a number of fragments of DL06 were labeled and imaging in xenograft-bearing mice.

TABLE 1

Observed percentages of tumors overexpressing EGFR1 in various types of cancer

| Tumor type | Tumor overexpressing EGFR1 (%) |
|---|---|
| Head and neck | 80-100 |
| Breast | 14-91 |
| Renal | 50-90 |
| Non-small cell lung | 40-80 |
| Colon | 22-75 |
| Ovarian | 35-70 |
| Glioma | 40-63 |
| Pancreatic | 30-50 |
| Bladder | 31-48 |

Yewale C, Biomaterials. 2013 November; 34(34): 8690-707.

As described in Examples 1 and 2, DL06 Fab was developed by grafting of the dimerization arm into the CDR-H3 followed by phage display.

DL06 Fab was formatted into an scFv, (scFv)2, scFv-CH3 and scFv-Fc (FIG. 16). The different DL06 fragments as imaging agents for A431 xenografts expressing EGFR1 were compared.

Establishing A431 Xenografts and Imaging

Ten millions of A431 cells expressing EGFR1 were injected into the right flank of each female CD-1® Nude mouse. Imaging was done when xenograft volume reached 150-300 mm³.

The fragment dose was 0.5 nmole of 800CW-labeled fragment.

Mice were imaged at 1, 2, 3, 4 and 6, 24, 48 and 72 hours.

DL06 scFv-800CW Imaging

DL06 scFv-800CW biodistribution to mice bearing A431 cell xenografts is shown in FIG. 17.

DL06 scFv did not show preferential accumulation to the xenografts. The highest florescence of this fragment was seen on the kidneys. Liver distribution was significantly lower than kidney excretion. These results suggest that this fragment was eliminated quickly from the blood through kidney excretion, such that there was not sufficient time for xenograft accumulation.

DL06 (scFv)2-800CW Imaging

DL06 (scFv)2-800CW biodistribution to mice bearing A431 cell xenografts is shown in FIG. 18.

DL06 (scFv)2 showed clear accumulation to the xenografts specifically at 24 h and after. Fluorescence in the xenograft maintained higher level compared to the surrounding tissues up to 96 h post-injection for the three mice. The accumulation in the xenografts peaked at about 3-4 h, and fluorescence intensity at the xenografts was nearly four times higher than at the contralateral side of the mouse body (i.e., same position opposite to the xenograft on the mouse body). At 24 hours the xenograft had fluorescence intensity about 17-fold higher than that of the contralateral side (FIG. 19). Liver distribution and kidney excretion were at comparable levels for the first 24 h then the fluorescence cleared from these organs (FIG. 19).

Anti-MBP (scFv)2-800CW Imaging in A431 Xenograft-Bearing Mice

Anti-MBP (scFv)2-800CA biodistribution to mice bearing A431 cell xenografts is shown in FIG. 18.

In this experiment, MBP (scFv)2 labeled with 800CW-NHS was used as control for DL06 (scFv)2.

0.5 nmole of 800CW-labeled MBP (scFv)2 were injected into three mice bearing A431 xenografts. The mice were imaged 1, 2, 3, 4, 6, 24, 48 and 72 h post-injection.

Anti-MBP (scFv)2 did not show preferential accumulation to the xenografts. The highest florescence of this fragment was seen in the kidneys followed by liver. Liver distribution was significantly lower than kidney excretion.

Xenografts did not retain the MBP (scFv)2 for long and elimination took place at early time points (fluorescence has a minor peak at 2 h) (FIG. 19).

Fluorescence intensity at the xenografts was two-to-three times higher than at the contralateral side of the mouse body. At 24 hours the fluorescence had intensity about 7-fold higher than that of the contralateral side.

DL06 Fab-800CW Imaging

DL06 Fab-800CW biodistribution to mice bearing A431 cell xenografts is shown in FIG. 20.

DL06 Fab did not show preferential accumulation to the xenografts. The highest florescence of the Fab was seen on the kidneys. Liver distribution of the Fab was significantly lower than kidney excretion. It is clear that the Fab got eliminated from the blood fast through kidney excretion which didn't allow enough time for xenograft accumulation.

DL06 Fab-800CW+ MBP Fab-800RD Imaging

Two of the mice described above were imaged with two dyes.

DL06 Fab-800CW+ MBP Fab-680RD biodistribution to mice bearing A431 cell xenografts is shown in FIG. 21.

This example was designed to confirm whether the DL06 Fab could accumulate in the xenograft relatively higher than the control MBP Fab.

Mice were co-injected with 0.5 nmole of each of DL06 Fab and MBP Fab and imaged at 1, 2, 3, 4, 6, 24, 48 and 72 h post-injection.

800CW fluorescence was set as GREEN pseudocolor while 680RD fluorescence was set as RED pseudocolor.

680RD fluorescence covered the whole abdominal cavity up to 48 h, while no accumulation of MBP fluorescence in the xenograft was observed at any time point. Similarly, 800CW fluorescence was seen mainly in kidneys, while the DL06 Fab didn't show appreciable accumulation to the xenograft.

DL06 scFv-CH3-800CW Imaging

DL06 scFv-CH3-800CW biodistribution to mice bearing A431 cell xenografts is shown in FIG. 22.

DL06 scFv-CH3 was imaged in two mice. 0.5 nmole of 800CW-labeled fragment was injected into mice bearing A431 xenografts. The mice were imaged at 1, 2, 3, 4, 6, 24, 48 and 72 h post-injection.

DL06 scFv-CH3 did not show preferential accumulation to the xenografts. The fragment did not distribute to the kidneys. Liver distribution was significantly high.

DL06 scFv-Fc-800CW Imaging

DL06 scFv-Fc-800CW biodistribution to mice bearing A431 cell xenografts is shown in FIG. 23.

DL06 scFv-Fc was imaged in two doses and three mice. 0.5 nmole of 800CW-labeled DL06 scFv-Fc was injected into one mouse bearing A431 xenografts and 1.5 nmole of 800CW-labeled DL06 scFv-Fc was injected into two mice bearing A431 xenografts. The mice were imaged at 1, 2, 3, 4, 6, 24, 48 and 72 h post-injection.

DL06 scFv-Fc did not show preferential accumulation to the xenografts at 0.5 nmole dose. At 1.5 nmole dose there was initial accumulation that cleared fast from one mouse but lasted in the other. The size of the xenograft may have been a factor. The fragment did not distribute to the kidneys. Liver distribution was significantly high.

Example 5

DL06 Fragments Flow Cytometry Data on A431 Cells (FIGS. 26 and 27)

DL06 (scFv2) was the only fragment that saturated on A431 by flow cytometry.

The DL06 (scFv)2 fragment had a Kd of 85 nM, which indicates good binding in vitro, and was translated into good binding in vivo.

(scFv)2 showed the highest affinity for the EGFR+ cell line A431, followed by Fc-scFv, scFv, Fab and CH3s-scFv showed similar lower affinity.

The in vitro flow cytometry data correlated with the in vivo imaging results, where the (scFv)2 showed the best imaging properties.

| TABLE OF SEQUENCES | |
|---|---|
| SEQUENCES IN FIG. 30: | |
| SEQ ID NO: 1 | QSVSSA |
| SEQ ID NO: 2 | SAS |

TABLE OF SEQUENCES

| | |
|---|---|
| SEQ ID NO: 3 | QQWSYYPIT |
| SEQ ID NO: 4 | QQWSYYPFT |
| SEQ ID NO: 5 | QQSYWLIT |
| SEQ ID NO: 6 | GFNISSSSI |
| SEQ ID NO: 7 | GFNFSSSSI |
| SEQ ID NO: 8 | GFNLYSSSM |
| SEQ ID NO: 9 | YISSYYSSTY |
| SEQ ID NO: 10 | SIYPYSGYTY |
| SEQ ID NO: 11 | ARTYCPPLMLYNPTTYQMDVNPEGKYSFGATCGWAMDY |
| SEQ ID NO: 12 | ARTFCPPLMLYNPTTYQLEINPEAKYSFASTCGWAMDY |
| SEQ ID NO: 13 | ARTFCPPIMLFNATSFELDIDAEAKFSFASTCGWAMDY |
| SEQ ID NO: 14 | ARTFCPPLMLFNPTTFQLEINAEAKYSFASTCGWAMDY |
| SEQ ID NO: 15 | ARTYCPPLMRYNPTTYQMDVNPEAQYSFGATCGWAMDY |
| SEQ ID NO: 16 | ARYPFGVSAYYAMDY |

SEQUENCES IN FIG. 10:

| | |
|---|---|
| SEQ ID NO: 17 | SSYSLI |
| SEQ ID NO: 18 | FSSSSI |
| SEQ ID NO: 19 | SISSSYGYTY |
| SEQ ID NO: 20 | TVRGSKKPYFSGWAM |
| SEQ ID NO: 21 | WSYYPI |
| SEQ ID NO: 22 | ISSSSI |
| SEQ ID NO: 23 | YISSYYSSTY |
| SEQ ID NO: 24 | TYCPPLMLYNPTTYQMDVNPEGKYSFGATCGWAM |
| SEQ ID NO: 25 | WSYYPI |
| SEQ ID NO: 26 | ISSSSI |
| SEQ ID NO: 27 | YISSYYSSTY |
| SEQ ID NO: 28 | TYCPPLMRYNPTTYQMDVNPEAQYSFGATCGWAM |
| SEQ ID NO: 29 | SYWLI |
| SEQ ID NO: 30 | LYSSSM |
| SEQ ID NO: 31 | SIYPYSGYTY |
| SEQ ID NO: 32 | YPFGVSAYYAM |

Nucleic and amino acid sequences

DL06 Heavy chain nucleotide sequence (SEQ ID NO: 33)
```
GAGGTTCAGCTGGTGGAGTCTGGCGGTGGCCTGGTGCAGCCAGGGGGCT
CACTCCGTTTGTCCTGTGCAGCTTCTGGCTTCAACATCTCTTCTTCTTCTATC
CACTGGGTGCGTCAGGCCCCGGGTAAGGGCCTGGAATGGGTTGCATATAT
TTCTTCTTATTATAGCTCTACTTATTATGCCGATAGCGTCAAGGGCCGTTTCA
CTATAAGCGCAGACACATCCAAAAACACAGCCTACCTACAAATGAACAGCCT
GAGAGCTGAGGACACTGCCGTCTATTATTGTGCTCGCACTTACTGTCCCCC
CCTGATGCTGTACAACCCCACTACTTACCAAATGGACGTCAACCCCGAAGG
TAAATACTCTTTTGGTGCTACTTGTGGCTGGGCTATGGACTACTGGGGTCAA
GGAACCCTGGTCACCGTCTCCTCGGCCTCCACCAAGGGCCCATCGGTCTTC
CCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACTC
AGGCGCCCTGACCAGCGGCGTGCACACCTTCCCGGCTGTCCTACAGTCCT
```

TABLE OF SEQUENCES

CAGGACTCTACTCCCTCAGCAGCGTGGTGACCGTGCCCTCCAGCAGCTTG
GGCACCCAGACCTACATCTGCAACGTGAATCACAAGCCCAGCAACACCAAG
GTCGACAAGAAAGTTGAGCCCAAATCTTGTGACAAAACTCACACATAA

DL06 Heavy chain amino acid sequence (SEQ ID NO: 34)
EVQLVESGGGLVQPGGSLRLSCAASGFNISSSSIHWVRQAPGKGLEWVAYISS
YYSSTYYADSVKGRFTISADTSKNTAYLQMNSLRAEDTAVYYCARTYCPPLMLY
NPTTYQMDVNPEGKYSFGATCGWAMDYWGQGTLVTVSSASTKGPSVFPLAP
SSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHT DL06 Light chain nucleotide sequence (SEQ ID NO: 35)
GATATCCAGATGACCCAGTCCCCGAGCTCCCTGTCCGCCTCTGTGGGCGAT
AGGGTCACCATCACCTGCCGTGCCAGTCAGTCCGTGTCCAGCGCTGTAGC
CTGGTATCAACAGAAACCAGGAAAAGCTCCGAAGCTTCTGATTTACTCGGCA
TCCAGCCTCTACTCTGGAGTCCCTTCTCGCTTCTCTGGTAGCCGTTCCGGG
ACGGATTTCACTCTGACCATCAGCAGTCTGCAGCCGGAAGACTTCGCAACT
TATTACTGTCAGCAATGGTCTTACTACCCGATCACGTTCGGACAGGGTACCA
AGGTGGAGATCAAACGAACTGTGGCTGCACCATCTGTCTTCATCTTCCCGC
CATCTGATTCACAGCTTAAGTCTGGAACTGCCTCTGTTGTGTGCCTGCTGAA
TAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACA
GCACCTACAGCCTCAGCAGCACCCTGACGCTGAGCAAAGCAGACTACGAAA
AACATAAAGTCTACGCCTGCGAAGTCACCCATCAGGGCCTGAGCTCGCCCG
TCACAAAGAGCTTCAACAGGGGAGAGTGTGGTGGTTCTGATTACAAAGATG
ACGATGACAAATAA DL06 Light chain amino acid sequence (SEQ ID NO: 36)
DIQMTQSPSSLSASVGDRVTITCRASQSVSSAVAWYQQKPGKAPKLLIYSASSL
YSGVPSRFSGSRSGTDFTLTISSLQPEDFATYYCQQWSYYPITFGQGTKVEIKR
TVAAPSVFIFPPSDSQLKSGTASVVCLLNNFYPREAKVQWKVDNALQSGNSQE
SVTEQDSKDSTYSLSSTLTLSKADYEKHKVYACEVTHQGLSSPVTKSFNRGEC
GGSDYKDDDDK Fab DL06 AM Clone 10 Heavy chain nucleic acid sequence (SEQ ID
NO: 37)
GAGGTTCAGCTGGTGGAGTCTGGCGGTGGCCTGGTGCAGCCAGGGGGCT
CACTCCGTTTGTCCTGTGCAGCTTCTGGCTTCAACATCTCTTCTTCTTCTATC
CACTGGGTGCGTCAGGCCCCGGGTAAGGGCCTGGAATGGGTTGCATATAT
TTCTTCTTATTATAGCTCTACTTATTATGCCGATAGCGTCAAGGGCCGTTTCA
CTATAAGCGCAGACACATCCAAAAACACAGCCTACCTACAAATGAACAGCCT
GAGAGCTGAGGACACTGCCGTCTATTATTGTGCTCGCACTTTCTGCCCACC
ACTCATGCTCTACAACCCAACCACCTACCAACTGGAAATTAACCCAGAAGCT
AAGTACTCCTTCGCTTCTACCTGCGGTTGGGCTATGGACTACTGGGGTCAA
GGAACCCTGGTCACCGTCTCCTCGGCCTCCACCAAGGGCCCATCGGTCTTC
CCCCTGGCACCCTCCTCCAAGAGCACCTCTGGGGGCACAGCGGCCCTGGG
CTGCCTGGTCAAGGACTACTTCCCGGAACCGGTGACGGTGTCGTGGAACTC
AGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTG
GGCACCCAGACCTACATCTGCAACGTGAATCACAAGCCCAGCAACACCAAG
GTCGACAAGAAAGTTGAGCCCAAATCTTGTGACAAAACTCACACATAA Fab DL06 AM Clone 10 Heavy chain amino acid sequence (SEQ ID
NO: 38)
EVQLVESGGGLVQPGGSLRLSCAASGFNISSSSIHWVRQAPGKGLEWVAYISS
YYSSTYYADSVKGRFTISADTSKNTAYLQMNSLRAEDTAVYYCARTFCPPLMLY
NPTTYQLEINPEAKYSFASTCGWAMDYWGQGTLVTVSSASTKGPSVFPLAPSS
KSTSGGTAALGCLVKDYFPEPVTVSWNSGALTSGVHTFPAVLQSSGLYSLSSV
VTVPSSSLGTQTYICNVNHKPSNTKVDKKVEPKSCDKTHT Fab DL06 AM Clone 10 Light chain nucleic acid sequence (SEQ ID
NO: 39)
GATATCCAGATGACCCAGTCCCCGAGCTCCCTGTCCGCCTCTGTGGGCGAT
AGGGTCACCATCACCTGCCGTGCCAGTCAGTCCGTGTCCAGCGCTGTAGC
CTGGTATCAACAGAAACCAGGAAAAGCTCCGAAGCTTCTGATTTACTCGGCA
TCCAGCCTCTACTCTGGAGTCCCTTCTCGCTTCTCTGGTAGCCGTTCCGGG
ACGGATTTCACTCTGACCATCAGCAGTCTGCAGCCGGAAGACTTCGCAACT
TATTACTGTCAGCAATGGTCTTACTACCCGATCACGTTCGGACAGGGTACCA
AGGTGGAGATCAAACGAACTGTGGCTGCACCATCTGTCTTCATCTTCCCGC
CATCTGATTCACAGCTTAAGTCTGGAACTGCCTCTGTTGTGTGCCTGCTGAA
TAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACA
GCACCTACAGCCTCAGCAGCACCCTGACGCTGAGCAAAGCAGACTACGAAA
AACATAAAGTCTACGCCTGCGAAGTCACCCATCAGGGCCTGAGCTCGCCCG
TCACAAAGAGCTTCAACAGGGGAGAGTGTGGTGGTTCTGATTACAAAGATG
ACGATGACAAATAA

TABLE OF SEQUENCES

Fab DL06 AM Clone 10 Light chain amino acid sequence (SEQ ID NO: 40)
DIQMTQSPSSLSASVGDRVTITCRASQSVSSAVAWYQQKPGKAPKLLIYSASSL
YSGVPSRFSGSRSGTDFTLTISSLQPEDFATYYCQQWSYYPITFGQGTKVEIKR
TVAAPSVFIFPPSDSQLKSGTASVVCLLNNFYPREAKVQWKVDNALQSGNSQE
SVTEQDSKDSTYSLSSTLTLSKADYEKHKVYACEVTHQGLSSPVTKSFNRGEC
GGSDYKDDDDK Fab DL06 AM Clone 23 Heavy chain nucleic acid sequence (SEQ ID NO: 41)
GAGGTTCAGCTGGTGGAGTCTGGCGGTGGCCTGGTGCAGCCAGGGGGCT
CACTCCGTTTGTCCTGTGCAGCTTCTGGCTTCAACATCTCTTCTTCTTCTATC
CACTGGGTGCGTCAGGCCCCGGGTAAGGGCCTGGAATGGGTTGCATATAT
TTCTTCTTATTATAGCTCTACTTATTATGCCGATAGCGTCAAGGGCCGTTTCA
CTATAAGCGCAGACACATCCAAAAACACAGCCTACCTACAAATGAACAGCCT
GAGAGCTGAGGACACTGCCGTCTATTATTGTGCTCGCACTTTCTGCCCACC
AATCATGCTCTTCAACGCAACCAGCTTCGAACTGGACATTGACGCAGAAGCT
AAGTTCTCCTTCGCTTCTACCTGCGGTTGGGCTATGGACTACTGGGGTCAA
GGAACCCTGGTCACCGTCTCCTCGGCCTCCACCAAGGGCCCATCGGTCTTC
CCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACTC
AGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTG
GGCACCCAGACCTACATCTGCAACGTGAATCACAAGCCCAGCAACACCAAG
GTCGACAAGAAAGTTGAGCCCAAATCTTGTGACAAAACTCACACATAA Fab DL06 AM Clone 23 Heavy chain amino acid sequence (SEQ ID NO: 42)
EVQLVESGGGLVQPGGSLRLSCAASGFNISSSSIHWVRQAPGKGLEWVAYISS
YYSSTYYADSVKGRFTISADTSKNTAYLQMNSLRAEDTAVYYCARTFCPPIMLF
NATSFELDIDAEAKFSFASTCGWAMDYWGQGTLVTVSSASTKGPSVFPLAPSS
KSTSGGTAALGCLVKDYFPEPVTVSWNSGALTSGVHTFPAVLQSSGLYSLSSV
VTVPSSSLGTQTYICNVNHKPSNTKVDKKVEPKSCDKTHT Fab DL06 AM Clone 23 Light chain nucleic acid sequence (SEQ ID NO: 43)
GATATCCAGATGACCCAGTCCCCGAGCTCCCTGTCCGCCTCTGTGGGCGAT
AGGGTCACCATCACCTGCCGTGCCAGTCAGTCCGTGTCCAGCGCTGTAGC
CTGGTATCAACAGAAACCAGGAAAAGCTCCGAAGCTTCTGATTTACTCGGCA
TCCAGCCTCTACTCTGGAGTCCCTTCTCGCTTCTCTGGTAGCCGTTCCGGG
ACGGATTTCACTCTGACCATCAGCAGTCTGCAGCCGGAAGACTTCGCAACT
TATTACTGTCAGCAATGGTCTTACTACCCGATCACGTTCGGACAGGGTACCA
AGGTGGAGATCAAACGAACTGTGGCTGCACCATCTGTCTTCATCTTCCCGC
CATCTGATTCACAGCTTAAGTCTGGAACTGCCTCTGTTGTGTGCCTGCTGAA
TAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACA
GCACCTACAGCCTCAGCAGCACCCTGACGCTGAGCAAAGCAGACTACGAAA
AACATAAAGTCTACGCCTGCGAAGTCACCCATCAGGGCCTGAGCTCGCCCG
TCACAAAGAGCTTCAACAGGGGAGAGTGTGGTGGTTCTGATTACAAAGATG
ACGATGACAAATAA Fab DL06 AM Clone 23 Light chain amino acid sequence (SEQ ID NO: 44)
DIQMTQSPSSLSASVGDRVTITCRASQSVSSAVAWYQQKPGKAPKLLIYSASSL
YSGVPSRFSGSRSGTDFTLTISSLQPEDFATYYCQQWSYYPITFGQGTKVEIKR
TVAAPSVFIFPPSDSQLKSGTASVVCLLNNFYPREAKVQWKVDNALQSGNSQE
SVTEQDSKDSTYSLSSTLTLSKADYEKHKVYACEVTHQGLSSPVTKSFNRGEC
GGSDYKDDDDK Fab DL06 AM Clone 24 Heavy chain nucleic acid sequence (SEQ ID NO: 45)
GAGGTTCAGCTGGTGGAGTCTGGCGGTGGCCTGGTGCAGCCAGGGGGCT
CACTCCGTTTGTCCTGTGCAGCTTCTGGCTTCAACATCTCTTCTTCTTCTATC
CACTGGGTGCGTCAGGCCCCGGGTAAGGGCCTGGAATGGGTTGCATATAT
TTCTTCTTATTATAGCTCTACTTATTATGCCGATAGCGTCAAGGGCCGTTTCA
CTATAAGCGCAGACACATCCAAAAACACAGCCTACCTACAAATGAACAGCCT
GAGAGCTGAGGACACTGCCGTCTATTATTGTGCTCGCACTTTCTGCCCACC
ACTCATGCTCTTCAACCCAACCACCTTCCAACTGGAAATTAACGCAGAAGCT
AAGTACTCCTTCGCTTCTACCTGCGGTTGGGCTATGGACTACTGGGGTCAA
GGAACCCTGGTCACCGTCTCCTCGGCCTCCACCAAGGGCCCATCGGTCTTC
CCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACTC
AGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTG
GGCACCCAGACCTACATCTGCAACGTGAATCACAAGCCCAGCAACACCAAG
GTCGACAAGAAAGTTGAGCCCAAATCTTGTGACAAAACTCACACATAA

TABLE OF SEQUENCES

Fab DL06 AM Clone 24 Heavy chain amino acid sequence (SEQ ID NO: 46)
EVQLVESGGGLVQPGGSLRLSCAASGFNISSSSIHWVRQAPGKGLEWVAYISS
YYSSTYYADSVKGRFTISADTSKNTAYLQMNSLRAEDTAVYYCARTFCPPLMLF
NPTTFQLEINAEAKYSFASTCGWAMDYWGQGTLVTVSSASTKGPSVFPLAPSS
KSTSGGTAALGCLVKDYFPEPVTVSWNSGALTSGVHTFPAVLQSSGLYSLSSV
VTVPSSSLGTQTYICNVNHKPSNTKVDKKVEPKSCDKTHT Fab DL06 AM Clone 24 Light chain nucleic acid sequence (SEQ ID NO: 47)
GATATCCAGATGACCCAGTCCCCGAGCTCCCTGTCCGCCTCTGTGGGCGAT
AGGGTCACCATCACCTGCCGTGCCAGTCAGTCCGTGTCCAGCGCTGTAGC
CTGGTATCAACAGAAACCAGGAAAAGCTCCGAAGCTTCTGATTTACTCGGCA
TCCAGCCTCTACTCTGGAGTCCCTTCTCGCTTCTCTGGTAGCCGTTCCGGG
ACGGATTTCACTCTGACCATCAGCAGTCTGCAGCCGGAAGACTTCGCAACT
TATTACTGTCAGCAATGGTCTTACTACCCGATCACGTTCGGACAGGGTACCA
AGGTGGAGATCAAACGAACTGTGGCTGCACCATCTGTCTTCATCTTCCCGC
CATCTGATTCACAGTTGAAATCTGGAACTGCCTCTGTTGTGTGCCTGCTGAA
TAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACA
GCACCTACAGCCTCAGCAGCACCCTGACGCTGAGCAAAGCAGACTACGAAA
AACATAAAGTCTACGCCTGCGAAGTCACCCATCAGGGCCTGAGCTCGCCCG
TCACAAAGAGCTTCAACAGGGGAGAGTGTGGTGGTTCTGATTACAAAGATG
ACGATGACAAATAA Fab DL06 AM Clone 24 Light chain amino acid sequence (SEQ ID NO: 48)
DIQMTQSPSSLSASVGDRVTITCRASQSVSSAVAWYQQKPGKAPKLLIYSASSL
YSGVPSRFSGSRSGTDFTLTISSLQPEDFATYYCQQWSYYPITFGQGTKVEIKR
TVAAPSVFIFPPSDSQLKSGTASVVCLLNNFYPREAKVQWKVDNALQSGNSQE
SVTEQDSKDSTYSLSSTLTLSKADYEKHKVYACEVTHQGLSSPVTKSFNRGEC
GGSDYKDDDDK Fab 8708 (Fab DL06 AM SR02) Heavy chain amino acid sequence (SEQ ID NO: 49)
GAGGTTCAGCTGGTGGAGTCTGGCGGTGGCCTGGTGCAGCCAGGGGCT
CACTCCGTTTGTCCTGTGCAGCTTCTGGCTTCAACATCTCTTCTTCTTCTATC
CACTGGGTGCGTCAGGCCCCGGGTAAGGGCCTGGAATGGGTTGCATATAT
TTCTTCTTATTATAGCTCTACTTATTATGCCGATAGCGTCAAGGGCCGTTTCA
CTATAAGCGCAGACACATCCAAAAACACAGCCTACCTACAAATGAACAGCCT
GAGAGCTGAGGACACTGCCGTCTATTATTGTGCTCGCACTTACTGTCCCCC
CCTGATGCGGTACAACCCCACTACTTACCAAATGGACGTCAACCCCGAGGC
TCAATACTCTTTTGGGGCTACTTGTGGCTGGGCTATGGACTACTGGGGTCA
AGGAACCCTGGTCACCGTCTCTCGGCCTCCACCAAGGGCCCATCGGTCTT
CCCCCTGGCACCCTCCTCCAAGAGCACCTCTGGGGGCACAGCGGCCCTGG
GCTGCCTGGTCAAGGACTACTTCCCGGAACCGGTGACGGTGTCGTGGAAC
TCAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGCTT
GGGCACCCAGACCTACATCTGCAACGTGAATCACAAGCCCAGCAACACCAA
GGTCGACAAGAAAGTTGAGCCCAAATCTTGTGACAAAACTCACACATAA Fab 8708 (Fab DL06 AM SR02) Heavy chain amino acid sequence (SEQ ID NO: 50)
EVQLVESGGGLVQPGGSLRLSCAASGFNISSSSIHWVRQAPGKGLEWVAYISS
YYSSTYYADSVKGRFTISADTSKNTAYLQMNSLRAEDTAVYYCARTYCPPLMR
YNPTTYQMDVNPEAQYSFGATCGWAMDYWGQGTLVTVSSASTKGPSVFPLA
PSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHT Fab 8708 (Fab DL06 AM SR02) Light chain nucleic acid sequence (SEQ ID NO: 51)
GATATCCAGATGACCCAGTCCCCGAGCTCCCTGTCCGCCTCTGTGGGCGAT
AGGGTCACCATCACCTGCCGTGCCAGTCAGTCCGTGTCCAGCGCTGTAGC
CTGGTATCAACAGAAACCAGGAAAAGCTCCGAAGCTTCTGATTTACTCGGCA
TCCAGCCTCTACTCTGGAGTCCCTTCTCGCTTCTCTGGTAGCCGTTCCGGG
ACGGATTTCACTCTGACCATCAGCAGTCTGCAGCCGGAAGACTTCGCAACT
TATTACTGTCAGCAATGGTCTTACTACCCGATCACGTTCGGACAGGGTACCA
AGGTGGAGATCAAACGAACTGTGGCTGCACCATCTGTCTTCATCTTCCCGC
CATCTGATTCACAGTTGAAATCTGGAACTGCCTCTGTTGTGTGCCTGCTGAA
TAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACA
GCACCTACAGCCTCAGCAGCACCCTGACGCTGAGCAAAGCAGACTACGAAA
AACATAAAGTCTACGCCTGCGAAGTCACCCATCAGGGCCTGAGCTCGCCCG
TCACAAAGAGCTTCAACAGGGGAGAGTGTGGTGGTTCTGATTACAAAGATG
ACGATGACAAATAA -continued

TABLE OF SEQUENCES

Fab 8708 (Fab DL06 AM SR02) Light chain amino acid sequence (SEQ ID NO: 52)
DIQMTQSPSSLSASVGDRVTITCRASQSVSSAVAWYQQKPGKAPKLLIYSASSL
YSGVPSRFSGSRSGTDFTLTISSLQPEDFATYYCQQWSYYPITFGQGTKVEIKR
TVAAPSVFIFPPSDSQLKSGTASVVCLLNNFYPREAKVQWKVDNALQSGNSQE
SVTEQDSKDSTYSLSSTLTLSKADYEKHKVYACEVTHQGLSSPVTKSFNRGEC
GGSDYKDDDDK Fab 8709 (Fab H) Heavy chain nucleic acid sequence (SEQ ID NO: 53)
GAGGTTCAGCTGGTGGAGTCTGGCGGTGGCCTGGTGCAGCCAGGGGGCT
CACTCCGTTTGTCCTGTGCAGCTTCTGGCTTCAACCTCTATTCTTCTTCTATG
CACTGGGTGCGTCAGGCCCCGGGTAAGGGCCTGGAATGGGTTGCATCTAT
TTATCCTTATTCTGGCTATACTTATTATGCCGATAGCGTCAAGGGCCGTTTCA
CTATAAGCGCAGACACATCCAAAAACACAGCCTACCTACAAATGAACAGCTT
AAGAGCTGAGGACACTGCCGTCTATTATTGTGCTCGCTACCCGTTCGGTGT
TTCTGCTTACTACGCTATGGACTACTGGGGTCAAGGAACCCTGGTCACCGT
CTCCTCGGCCTCCACCAAGGGTCCATCGGTCTTCCCCCTGGCACCCTCCTC
CAAGAGCACCTCTGGGGGCACAGCGGCCCTGGGCTGCCTGGTCAAGGACT
ACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACAT
CTGCAACGTGAATCACAAGCCCAGCAACACCAAGGTCGACAAGAAAGTTGA
GCCCAAATCTTGTGACAAAACTCACACATAA Fab 8709 (Fab H) Heavy chain amino acid sequence (SEQ ID NO: 54)
EVQLVESGGGLVQPGGSLRLSCAASGFNLYSSSMHWVRQAPGKGLEWVASIY
PYSGYTYYADSVKGRFTISADTSKNTAYLQMNSLRAEDTAVYYCARYPFGVSA
YYAMDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPS
NTKVDKKVEPKSCDKTHT Fab 8709 (Fab H) Light chain nucleic acid sequence (SEQ ID NO: 55)
GATATCCAGATGACCCAGTCCCCGAGCTCCCTGTCCGCCTCTGTGGGCGAT
AGGGTCACCATCACCTGCCGTGCCAGTCAGTCCGTGTCCAGCGCTGTAGC
CTGGTATCAACAGAAACCAGGAAAAGCTCCGAAGCTTCTGATTTACTCGGCA
TCCAGCCTCTACTCTGGAGTCCCTTCTCGCTTCTCTGGTAGCCGTTCCGGG
ACGGATTTCACTCTGACCATCAGCAGTCTGCAGCCGGAAGACTTCGCAACT
TATTACTGTCAGCAATCTTACTGGCTGATCACGTTCGGACAGGGTACCAAGG
TGGAGATCAAACGAACTGTGGCTGCACCATCTGTCTTCATCTTCCCGCCATC
TGATTCACAGTTGAAATCTGGAACTGCCTCTGTTGTGTGCCTGCTGAATAAC
TTCTATCCCAGAGAGGCCAAAGTACAGTGGAAGGTGGATAACGCCCTCCAA
TCGGGTAACTCCCAGGAGAGTGTCACAGAGCAGGACAGCAAGGACGCAC
CTACAGCCTCAGCAGCACCCTGACGCTGAGCAAAGCAGACTACGAAAAACA
TAAAGTCTACGCCTGCGAAGTCACCCATCAGGGCCTGAGCTCGCCCGTCAC
AAAGAGCTTCAACAGGGGAGAGTGTGGTGGTTCTGATTACAAAGATGACGA
TGACAAATAA Fab 8709 (Fab H) Light chain amino acid sequence (SEQ ID NO: 56)
DIQMTQSPSSLSASVGDRVTITCRASQSVSSAVAWYQQKPGKAPKLLIYSASSL
YSGVPSRFSGSRSGTDFTLTISSLQPEDFATYYCQQSYWLITFGQGTKVEIKRT
VAAPSVFIFPPSDSQLKSGTASVVCLLNNFYPREAKVQWKVDNALQSGNSQES
VTEQDSKDSTYSLSSTLTLSKADYEKHKVYACEVTHQGLSSPVTKSFNRGECG
GSDYKDDDDK

SEQ ID NO: 57
CPPLMLYNPTTYQMDVNPEGKYSFGATC

SEQ ID NO: 58
TVRGSKKPYFSGWAM

REFERENCES (1) Aboud-Pirak, E., Hurwitz, E., Pirak, M. E., Bellot, F., Schlessinger, J., and Sela, M. (1988) Efficacy of Antibodies to Epidermal Growth Factor Receptor Against KB Carcinoma In Vitro and in Nude Mice. *JNCI J. Natl. Cancer Inst.* 80, 1605-1611.

(2) Knight, D. M., Trinh, H., Le, J., Siegel, S., Shealy, D., McDonough, M., Scallon, B., Moore, M. A., Vilcek, J., and Daddona, P. (1993) Construction and initial characterization of a mouse-human chimeric anti-TNF antibody. *Mol. Immunol.* 30, 1443-53.

(3) Presta, L. G., Chen, H., O'Connor, S. J., Chisholm, V., Meng, Y. G., Krummen, L., Winkler, M., and Ferrara, N. (1997) Humanization of an anti-vascular endothelial growth factor monoclonal antibody for the therapy of solid tumors and other disorders. *Cancer Res.* 57, 4593-9.

(4) Schaefer, G., Haber, L., Crocker, L. M., Shia, S., Shao, L., Dowbenko, D., Totpal, K., Wong, A., Lee, C. V, Stawicki, S., Clark, R., Fields, C., Lewis Phillips, G. D., Prell, R. A., Danilenko, D. M., Franke, Y., Stephan, J.-P., Hwang, J., Wu, Y., Bostrom, J., Sliwkowski, M. X., Fuh, G., and Eigenbrot, C. (2011) A two-in-one antibody against HER3 and EGFR has superior inhibitory activity compared with monospecific antibodies. *Cancer Cell* 20, 472-86.

(5) Wu, Y., Cain-Hom, C., Choy, L., Hagenbeek, T. J., de Leon, G. P., Chen, Y., Finkle, D., Venook, R., Wu, X., Ridgway, J., Schahin-Reed, D., Dow, G. J., Shelton, A., Stawicki, S., Watts, R. J., Zhang, J., Choy, R., Howard, P., Kadyk, L., Yan, M., Zha, J., Callahan, C. A., Hymowitz, S. G., and Siebel, C. W. (2010) Therapeutic antibody targeting of individual Notch receptors. *Nature* 464, 1052-7.

(6) Pierschbacher, M. D., and Ruoslahti, E. (1984) Cell attachment activity of fibronectin can be duplicated by small synthetic fragments of the molecule. *Nature* 309, 30-33.

(7) Pawson, T., and Nash, P. (2003) Assembly of cell regulatory systems through protein interaction domains. *Science* 300, 445-52.

(8) Garrett, T. P. J., McKern, N. M., Lou, M., Elleman, T. C., Adams, T. E., Lovrecz, G. O., Zhu, H.-J., Walker, F., Frenkel, M. J., Hoyne, P. A., Jorissen, R. N., Nice, E. C., Burgess, A. W., and Ward, C. W. (2002) Crystal structure of a truncated epidermal growth factor receptor extracellular domain bound to transforming growth factor alpha. *Cell* 110, 763-73.

(9) Syed, R. S., Reid, S. W., Li, C., Cheetham, J. C., Aoki, K. H., Liu, B., Zhan, H., Osslund, T. D., Chirino, A. J., Zhang, J., Finer-Moore, J., Elliott, S., Sitney, K., Katz, B. A., Matthews, D. J., Wendoloski, J. J., Egrie, J., and Stroud, R. M. (1998) Efficiency of signalling through cytokine receptors depends critically on receptor orientation. *Nature* 395, 511-6.

(10) Aragues, R., Sali, A., Bonet, J., Marti-Renom, M. A., and Oliva, B. (2007) Characterization of protein hubs by inferring interacting motifs from protein interactions. *PLoS Comput. Biol.* 3, 1761-71.

(11) Perchiacca, J. M., Ladiwala, A. R. A., Bhattacharya, M., and Tessier, P. M. (2012) Structure-based design of conformation- and sequence-specific antibodies against amyloid β. *Proc. Natl. Acad. Sci. U.S.A.* 109, 84-9.

(12) Barbas, C. F., Languino, L. R., and Smith, J. W. (1993) High-affinity self-reactive human antibodies by design and selection: targeting the integrin ligand binding site. *Proc. Natl. Acad. Sci. U.S.A.* 90, 10003-10007.

(13) Lee, J.-C., Park, S.-Y., Choi, C.-Y., Chung, J., and Lee, M.-S. (2007) Generation of a naïve/synthetic antibody specific to botulinum neurotoxin via motif-grafting. *Biotechnol. Bioprocess Eng.* 12, 282-288.

(14) Mattoon, D., Klein, P., Lemmon, M. A., Lax, I., and Schlessinger, J. (2004) The tethered configuration of the EGF receptor extracellular domain exerts only a limited control of receptor function. *Proc. Natl. Acad. Sci. U.S.A.* 101, 923-8.

(15) Ogiso, H. (2002) Crystal structure of the complex of human epidermal growth factor and receptor extracellular domains. *Cell* 110, 775-787.

(16) Lemmon, M. A., Schlessinger, J., and Ferguson, K. M. (2014) The EGFR family: Not so prototypical receptor tyrosine kinases. *Cold Spring Harb. Perspect. Biol.* 6.

(17) Huang, M., Anand, S., Murphy, E. a, Desgrosellier, J. S., Stupack, D. G., Shattil, S. J., Schlaepfer, D. D., and Cheresh, D. a. (2012) EGFR-dependent pancreatic carcinoma cell metastasis through Rap1 activation. *Oncogene* 31, 2783-2793.

(18) Wang, Z., Longo, P. A., Tarrant, M. K., Kim, K., Head, S., Leahy, D. J., and Cole, P. A. (2011) Mechanistic insights into the activation of oncogenic forms of EGF receptor. *Nat. Struct. Mol. Biol.* 18, 1388-93.

(19) Bonner, J. A., Harari, P. M., Giralt, J., Azarnia, N., Shin, D. M., Cohen, R. B., Jones, C. U., Sur, R., Raben, D., Jassem, J., Ove, R., Kies, M. S., Baselga, J., Youssoufian, H., Amellal, N., Rowinsky, E. K., and Ang, K. K. (2006) Radiotherapy plus Cetuximab for Squamous-Cell Carcinoma of the Head and Neck. *N. Engl. J. Med.* 354, 567-578.

(20) Moroni, M., Veronese, S., Benvenuti, S., Marrapese, G., Sartore-Bianchi, A., Di Nicolantonio, F., Gambacorta, M., Siena, S., and Bardelli, A. (2005) Gene copy number for epidermal growth factor receptor (EGFR) and clinical response to antiEGFR treatment in colorectal cancer: a cohort study. *Lancet. Oncol.* 6, 279-86.

(21) Brand, T. M., lida, M., Stein, A. P., Corrigan, K. L., Braverman, C. M., Luthar, N., Toulany, M., Gill, P. S., Salgia, R., Kimple, R. J., and Wheeler, D. L. (2014) AXL mediates resistance to cetuximab therapy. *Cancer Res.* 74, 5152-64.

(22) Konieczkowski, D. J., and Garraway, L. A. (2013) Resistance to EGFR blockade in colorectal cancer: liquid biopsies and latent subclones. *Cell Res.* 23, 13-4.

(23) Ferguson, K. M., Berger, M. B., Mendrola, J. M., Cho, H. S., Leahy, D. J., and Lemmon, M. A. (2003) EGF activates its receptor by removing interactions that autoinhibit ectodomain dimerization. *Mol. Cell* 11, 507-517.

(24) Dawson, J. P., Berger, M. B., Lin, C., Schlessinger, J., Lemmon, M. A., Kathryn, M., and Ferguson, K. M. (2005) Epidermal Growth Factor Receptor Dimerization and Activation Require Ligand-Induced Conformational Changes in the Dimer Interface Epidermal Growth Factor Receptor Dimerization and Activation Require Ligand-Induced Conformational Changes in the Dimer Inter. *Mol. Cell. Biol.* 25, 7734-7742.

(25) Cho, H.-S., Mason, K., Ramyar, K. X., Stanley, A. M., Gabelli, S. B., Denney, D. W., and Leahy, D. J. (2003) Structure of the extracellular region of HER2 alone and in complex with the Herceptin Fab. *Nature* 421, 756-60.

(26) Persson, H., Ye, W., Wernimont, A., Adams, J. J., Koide, A., Koide, S., Lam, R., and Sidhu, S. S. (2013) CDR-H3 diversity is not required for antigen recognition by synthetic antibodies. *J. Mol. Biol.* 425, 803-811.

(27) Sidhu, S., and Fellouse, F. (2006) Making Antibodies in Bacteria, in *Making and Using Antibodies*, pp 157-180. CRC Press.

(28) Voigt, M., Braig, F., Göthel, M., Schulte, A., Lamszus, K., Bokemeyer, C., and Binder, M. (2012) Functional dissection of the epidermal growth factor receptor epitopes targeted by panitumumab and cetuximab. *Neoplasia* 14, 1023-31.

(29) Libermann, T. A., Nusbaum, H. R., Razon, N., Kris, R., Lax, I., Soreq, H., Whittle, N., Waterfield, M. D., Ullrich, A., and Schlessinger, J. Amplification, enhanced expression and possible rearrangement of EGF receptor gene in primary human brain tumours of glial origin. *Nature* 313, 144-7.

(30) Machiels, J.-P., Subramanian, S., Ruzsa, A., Repassy, G., Lifirenko, I., Flygare, A., Sørensen, P., Nielsen, T., Lisby, S., and Clement, P. M. J. (2011) Zalutumumab plus best supportive care versus best supportive care alone in patients with recurrent or metastatic squamous-cell carcinoma of the head and neck after failure of platinum-based chemotherapy: an open-label, randomised phase 3 trial. *Lancet. Oncol.* 12, 333-43.

(31) Bleeker, W. K., Lammerts van Bueren, J. J., van Ojik, H. H., Gerritsen, A. F., Pluyter, M., Houtkamp, M., Halk, E., Goldstein, J., Schuurman, J., van Dijk, M. A., van de Winkel, J. G. J., and Parren, P. W. H. I. (2004) Dual Mode of Action of a Human Anti-Epidermal Growth Factor Receptor Monoclonal Antibody for Cancer Therapy. *J. Immunol.* 173, 4699-4707.

(32) Crombet, T., Torres, L., Neninger, E., Catalá, M., Solano, M. E., Perera, A., Torres, O., Iznaga, N., Torres, F., Pérez, R., and Lage, A. (2003) Pharmacological evaluation of humanized anti-epidermal growth factor receptor, monoclonal antibody h-R3, in patients with advanced epithelial-derived cancer. *J. Immunother.* 26, 139-48.

(33) Fernandez, A., Spitzer, E., Perez, R., Boehmer, F. D., Eckert, K., Zschiesche, W., and Grosse, R. (1992) A new monoclonal antibody for detection of EGF-receptors in western blots and paraffin-embedded tissue sections. *J. Cell. Biochem.* 49, 157-65.

(34) Graeven, U., Kremer, B., Süadhoff, T., Killing, B., Rojo, F., Weber, D., Tillner, J., Unal, C., and Schmiegel, W. (2006) Phase I study of the humanised anti-EGFR monoclonal antibody matuzumab (EMD 72000) combined with gemcitabine in advanced pancreatic cancer. *Br. J. Cancer* 94, 1293-9.

(35) Murthy, U., Basu, A., Rodeck, U., Herlyn, M., Ross, A. H., and Das, M. (1987) Binding of an antagonistic monoclonal antibody to an intact and fragmented EGF-receptor polypeptide. *Arch. Biochem. Biophys.* 252, 549-60.

(36) Montagut, C., Dalmases, A., Bellosillo, B., Crespo, M., Pairet, S., Iglesias, M., Salido, M., Gallen, M., Marsters, S., Tsai, S. P., Minoche, A., Seshagiri, S., Somasekar, S., Serrano, S., Himmelbauer, H., Bellmunt, J., Rovira, A., Settleman, J., Bosch, F., and Albanell, J. (2012) Identification of a mutation in the extracellular domain of the Epidermal Growth Factor Receptor conferring cetuximab resistance in colorectal cancer. *Nat. Med.* 18, 221-3.

(37) Friedman, L. M., Rinon, A., Schechter, B., Lyass, L., Lavi, S., Bacus, S. S., Sela, M., and Yarden, Y. (2005) Synergistic down-regulation of receptor tyrosine kinases by combinations of mAbs: implications for cancer immunotherapy. *Proc. Natl. Acad. Sci. U.S.A.* 102, 1915-20.

(38) Klapper, L. N., Vaisman, N., Hurwitz, E., Pinkas-Kramarski, R., Yarden, Y., and Sela, M. (1997) A subclass of tumor-inhibitory monoclonal antibodies to ErbB-2/HER2 blocks crosstalk with growth factor receptors. *Oncogene* 14, 2099-109.

(39) Ko, B.-K., Lee, S.-Y., Lee, Y.-H., Hwang, I.-S., Persson, H., Rockberg, J., Borrebaeck, C., Park, D., Kim, K.-T., Uhlen, M., and Lee, J.-S. (2015) Combination of novel HER2-targeting antibody 1E11 with trastuzumab shows synergistic antitumor activity in HER2-positive gastric cancer. *Mol. Oncol.* 9, 398-408.

(40) Yamashita-Kashima, Y., Iijima, S., Yorozu, K., Furugaki, K., Kurasawa, M., Ohta, M., and Fujimoto-Ouchi, K. (2011) Pertuzumab in combination with trastuzumab shows significantly enhanced antitumor activity in HER2-positive human gastric cancer xenograft models. *Clin. Cancer Res.* 17, 5060-70.

(41) Zhou, Y., Zhang, J., Jin, H., Chen, Z., Wu, Q., Li, W., Yue, M., Luo, C., and Wang, M. (2013) Prokaryotic expression and refolding of EGFR extracellular domain and generation of phage display human scFv against EGFR. *Biomed. Pharmacother.* 67, 737-743.

(42) Moon, S. A., Ki, M. K., Lee, S., Hong, M.-L., Kim, M., Kim, S., Chung, J., Rhee, S. G., and Shim, H. (2011) Antibodies against non-immunizing antigens derived from a large immune scFv library. *Mol. Cells* 31, 509-13.

(43) Birtalan, S., Zhang, Y., Fellouse, F. A., Shao, L., Schaefer, G., and Sidhu, S. S. (2008) The Intrinsic Contributions of Tyrosine, Serine, Glycine and Arginine to the Affinity and Specificity of Antibodies. *J. Mol. Biol.* 377, 1518-1528.

(44) Hornsby, M., Paduch, M., Miersch, S., Sääf, A., Matsuguchi, T., Lee, B., Wypisniak, K., Doak, A., King, D., Usatyuk, S., Perry, K., Lu, V., Thomas, W., Luke, J., Goodman, J., Hoey, R. J., Lai, D., Griffin, C., Li, Z., Vizeacoumar, F. J., Dong, D., Campbell, E., Anderson, S., Zhong, N., Gräslund, S., Koide, S., Moffat, J., Sidhu, S., Kossiakoff, A., and Wells, J. (2015) A High Through-put Platform for Recombinant Antibodies to Folded Proteins. *Mol. Cell. Proteomics* 14, 2833-47.

(45) Sidhu, S. S., Li, B., Chen, Y., Fellouse, F. A., Eigenbrot, C., and Fuh, G. (2004) Phage-displayed antibody libraries of synthetic heavy chain complementarity determining regions. *J. Mol. Biol.* 338, 299-310.

(46) Kay, B. K., Thai, S., and Volgina, V. V. (2009) High-throughput biotinylation of proteins. *Methods Mol. Biol.* 498, 185-96.

(47) Carter, R. E., and Sorkin, A. (1998) Endocytosis of functional epidermal growth factor receptor-green fluorescent protein chimera. *J. Biol. Chem.* 273, 35000-7.

(48) Longo, P. A., Kavran, J. M., Kim, M.-S., and Leahy, D. J. (2013) Transient mammalian cell transfection with polyethylenimine (PEI). *Methods Enzymol.* 529, 227-40.

(49) Albitar, L., Laidler, L. L., Abdallah, R., and Leslie, K. K. (2005) Regulation of signaling phosphoproteins by epidermal growth factor and Iressa (ZD1839) in human endometrial cancer cells that model type I and II tumors. *Mol. Cancer Ther.* 4, 1891-9.

(50) Lefranc, M.-P., Pommié, C., Ruiz, M., Giudicelli, V., Foulquier, E., Truong, L., Thouvenin-Contet, V., and Lefranc, G. (2003) IMGT unique numbering for immunoglobulin and T cell receptor variable domains and Ig superfamily V-like domains. *Dev. Comp. Immunol.* 27, 55-77.

Green and Sambrook. Molecular Cloning: A Laboratory Manual (4th ed., Cold Spring Harbor Laboratory Press, Cold Spring Harbor, N.Y., (2012))

Kabat et al. 1991. Sequences of Proteins of Immunological Interest, 5th Ed. Public Health Service, National Institutes of Health, Bethesda, Md.

Lefranc et al., 2003. Development and Comparative Immunology 27:55-77

Lipi et al. 2015 RNA Biology 12: 1232-1245

Parashar 2016 International Journal of Bioassays Vol 5, No 02

McEnaney et al, 2015 J. Am. Chem. Soc., 2014, 136 (52), pp 18034-18043

Fauchere J. 1986. Adv. Drug Res. 15:29

Veber and Freidinger TINS p. 392 (1985)

Evans et al. 1987. J. Med. Chem. 30:1229

Rizo and Gierasch Ann. Rev. Biochem. 61:387 (1992)

Kostelny S A et al, J Immunol. 1992 Mar. 1; 148(5):1547-53

Hollinger et al, 1993. Proc Natl Acad Sci USA. 1993 Jul. 15; 90(14):6444-8

Gruber, M et al. 1994. J. Immunol., 152, 5368-5374.

Tutt et al. 1991 Eur. J. Immunol., 21, 1351-1358

Shopes, B. 1992. A genetically engineered human IgG mutant with enhanced cytolytic activity. J. Immunol. 148:2918.

Caron et al (1992), Cancer Res. 52, 6761-6767

Karlin and Altschul, 1990, Proc. Natl. Acad. Sci. U.S.A. 87:2264-2268

Karlin and Altschul, 1993, Proc. Natl. Acad. Sci. U.S.A. 90:5873-5877
Altschul et al. 1997. Nucleic Acids Res. 25:3389-3402
Myers and Miller, 1988, CABIOS 4:11-17
Greenfield, Antibodies: A Laboratory Manual, Cold Spring Harbor Laboratory Press, 2013
Kohler and Milstein, Nature, 256:495 (1975)
Malmqvist, Nature 361:186-87 (1993)
Davies et al. 1990. Annual Rev Biochem 59:439-473
Cruse and Lewis (Editors), Conjugate Vaccines (Contributions to Microbiology and Immunology Vol. 10). 1989

The invention claimed is:

1. An EGFR-binding agent, comprising an antibody variable region that specifically binds domain I and/or domain II of EGFR, the antibody variable region comprising:
   (i) a light chain complementarity determining region (CDR)1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 11,
   (ii) a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 5 and a heavy chain CDR1 comprising the amino acid sequence of amino acids 1-8 of SEQ ID NO: 8, a heavy chain CDR2 comprising the amino acid sequence of amino acids 2-9 of SEQ ID NO: 10, and a heavy chain CDR3 comprising the amino acid sequence of SEQ ID NO: 16,
   (iii) a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 4 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 12,
   (iv) a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 13,
   (v) a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 6, a heavy chain CDR2 comprising the amino acid sequence of amino acids 2-9 of SEQ ID NO: 9, and a heavy chain CDR3 comprising the amino acid sequence of SEQ ID NO: 14, or
   (vi) a light chain CDR1 comprising the amino acid sequence of SEQ ID NO: 1, a light chain CDR2 comprising the amino acid sequence of SEQ ID NO: 2, and a light chain CDR3 comprising the amino acid sequence of SEQ ID NO: 3 and a heavy chain CDR1 comprising the amino acid sequence of amino acids 1-8 of SEQ ID NO: 7, a heavy chain CDR2 comprising the amino acid sequence of amino acids 2-9 of SEQ ID NO: 9, and a heavy chain CDR3 comprising the amino acid sequence of SEQ ID NO: 15.

2. The EGFR-binding agent of claim 1, wherein the binding agent does not bind domain III of EGFR.

3. The EGFR-binding agent of claim 1, wherein the antibody variable region specifically binds human EGFR.

4. The EGFR-binding agent of claim 1, wherein the binding agent is selected from the group consisting of an antibody, an antibody fragment, a single-chain Fv (scFv), a bispecific antibody, a phage-Fab and a phage-scFv.

5. The EGFR-binding agent of claim 1, wherein the binding agent is a fragment antigen-binding (Fab).

6. The EGFR-binding agent of claim 1, wherein the EGFR-binding agent comprises human antibody constant regions.

7. The EGFR-binding agent of claim 1, wherein the EGFR-binding agent is an IgG molecule.

8. The EGFR-binding agent of claim 1, wherein the binding agent is labelled with a detection agent.

9. A conjugate comprising (1) the binding agent of claim 1 attached to (2) an effector agent.

10. The conjugate of claim 9, wherein the effector agent is an anti-neoplastic agent.

11. The conjugate of claim 10, wherein the effector agent is a toxin.

12. A pharmaceutical composition comprising the EGFR-binding agent of claim 1 and a carrier.

13. A method of binding EGFR-expressing cells comprising exposing the EGFR-binding agent of claim 1 to the EGFR-expressing cells.

14. A method of targeting EGFR-expressing cells comprising exposing the EGFR-binding agent of claim 1 to the EGFR-expressing cells.

15. The method claim 14, wherein the EGFR-expressing cells are cancer cells.

16. The method of claim 15, wherein the cancer cells are breast cancer cells or colon cancer cells.

* * * * *